United States Patent
Wu et al.

(10) Patent No.: US 10,682,044 B2
(45) Date of Patent: Jun. 16, 2020

(54) SPECTRALLY ENCODED FORWARD VIEW AND SPECTRALLY ENCODED MULTI-VIEW ENDOSCOPE USING BACK-REFLECTED LIGHT BETWEEN REFLECTIVE SURFACES

(71) Applicant: Canon U.S.A., Inc., Melville, NY (US)

(72) Inventors: Tzu-Yu Wu, Malden, MA (US); Mitsuhiro Ikuta, Cambridge, MA (US); Seiji Takeuchi, Newton, MA (US); Naoki Kohara, Kawasaki (JP); Osamu Koyama, Tokyo (JP)

(73) Assignee: Canon U.S.A., Inc., Melville, NY (US)

( * ) Notice: Subject to any disclaimer, the term of this patent is extended or adjusted under 35 U.S.C. 154(b) by 0 days.

(21) Appl. No.: 16/476,826

(22) PCT Filed: Jan. 10, 2018

(86) PCT No.: PCT/US2018/013192
§ 371 (c)(1),
(2) Date: Jul. 9, 2019

(87) PCT Pub. No.: WO2018/132490
PCT Pub. Date: Jul. 19, 2018

(65) Prior Publication Data
US 2019/0374092 A1    Dec. 12, 2019

Related U.S. Application Data

(60) Provisional application No. 62/445,465, filed on Jan. 12, 2017.

(51) Int. Cl.
*A61B 1/00* (2006.01)
*A61B 1/07* (2006.01)
(Continued)

(52) U.S. Cl.
CPC ...... *A61B 1/00181* (2013.01); *A61B 1/00096* (2013.01); *A61B 1/07* (2013.01);
(Continued)

(58) Field of Classification Search
CPC ... A61B 1/00181; A61B 1/00096; A61B 1/07; A61B 1/00165; A61B 1/0623;
(Continued)

(56) References Cited

U.S. PATENT DOCUMENTS

| 4,140,364 A | 2/1979 | Yamashita et al. |
| 4,744,618 A * | 5/1988 | Mahlein ............... G01J 3/0259 |
| | | 385/33 |

(Continued)

FOREIGN PATENT DOCUMENTS

| JP | 2017-505667 A | 2/2017 |
| WO | 2015/116939 A1 | 8/2015 |

(Continued)

OTHER PUBLICATIONS

Pitris, et al., "A GRISM-Based Probe for Spectrally Encoded Confocal Microscopy", Optics Express, The Optical Society, Washington DC, vol. 11, No. 2, Jan. 2003, pp. 120-124.

(Continued)

*Primary Examiner* — Andrew Jordan
(74) *Attorney, Agent, or Firm* — Canon U.S.A., Inc. IP Division

(57) ABSTRACT

A Spectrally Encoded Forward View or Multi-View Endoscope, Probe, and Imaging Apparatus and system, and methods and storage mediums for use therewith, are provided herein. At least one apparatus or system may comprise a first waveguide; an optical system; and a diffraction grating. The first waveguide may be for guiding light from a light source to an output port of the first waveguide. The optical system may comprise at least a first reflecting surface (Continued)

and a second reflecting surface. The first reflecting surface may be arranged to reflect light from the output port of the first waveguide to the second reflecting surface. The second reflecting surface may be arranged to reflect light from the first reflecting surface back through the first reflecting surface to the diffraction grating. The diffraction grating may diffract light from the second reflecting surface in several lights/colors of non-zero diffraction orders in a first direction.

26 Claims, 35 Drawing Sheets

(51) Int. Cl.
*G01J 3/02* (2006.01)
*G01J 3/18* (2006.01)
*G02B 5/18* (2006.01)
*G02B 3/00* (2006.01)

(52) U.S. Cl.
CPC ........... *G01J 3/0208* (2013.01); *G01J 3/0218* (2013.01); *G01J 3/18* (2013.01); *G02B 5/1814* (2013.01); *G02B 3/0087* (2013.01)

(58) Field of Classification Search
CPC .... A61B 1/0638; G01J 3/0208; G01J 3/0218; G01J 3/18; G01J 3/0205; G01J 3/0256; G01J 3/0289; G01J 3/0224; G02B 5/1814; G02B 3/0087; G02B 23/26; G02B 23/2469; G02B 26/10; G02B 27/4244

See application file for complete search history.

(56) References Cited

U.S. PATENT DOCUMENTS

| | | | |
|---|---|---|---|
| 5,208,882 A | 5/1993 | Strasser et al. | |
| 5,428,699 A | 6/1995 | Pon | |
| 5,596,433 A | 1/1997 | Konuma | |
| 6,275,630 B1* | 8/2001 | Yang | G02B 6/29311 385/24 |
| 6,341,036 B1 | 1/2002 | Tearney et al. | |
| 6,343,170 B1* | 1/2002 | Sela | G01J 3/0259 385/37 |
| 6,364,167 B1 | 4/2002 | Safian et al. | |
| 6,381,008 B1* | 4/2002 | Branagh | G01J 3/18 356/328 |
| 6,635,010 B1 | 10/2003 | Lederer | |
| 6,792,181 B2* | 9/2004 | Sasaki | G02B 6/4246 385/24 |
| 6,810,177 B2* | 10/2004 | Kaneko | G02B 6/12014 385/14 |
| 6,856,732 B2* | 2/2005 | Liu | G02B 6/124 385/15 |
| 6,900,919 B1* | 5/2005 | Islam | G02B 26/0808 359/224.1 |
| 6,970,242 B2* | 11/2005 | Puppels | G01J 3/18 356/327 |
| 6,972,886 B2* | 12/2005 | Islam | G02B 6/12009 359/204.1 |
| 7,088,877 B2* | 8/2006 | Liu | G02B 6/124 385/10 |
| 7,221,452 B2* | 5/2007 | Berger | G01J 3/12 356/327 |
| 7,447,408 B2 | 11/2008 | Bouma et al. | |
| 7,551,293 B2 | 6/2009 | Yelin et al. | |
| 7,566,131 B2 | 7/2009 | Mihashi | |
| 7,796,270 B2 | 9/2010 | Yelin et al. | |
| 7,847,949 B2 | 12/2010 | Tearney et al. | |
| 7,859,679 B2 | 12/2010 | Bouma et al. | |
| 7,889,348 B2 | 2/2011 | Tearney et al. | |
| 8,045,177 B2 | 10/2011 | Tearney et al. | |
| 8,145,018 B2 | 3/2012 | Shishkov et al. | |
| 8,184,375 B2 | 5/2012 | Towndrow et al. | |
| 8,773,500 B2 | 7/2014 | Wilson et al. | |
| 8,780,176 B2 | 7/2014 | Yelin | |
| 8,812,087 B2 | 8/2014 | Yelin et al. | |
| 8,838,213 B2 | 9/2014 | Tearney et al. | |
| 9,057,594 B2 | 6/2015 | Kang et al. | |
| 9,122,067 B2 | 9/2015 | Honda et al. | |
| 9,254,089 B2 | 2/2016 | Tearney et al. | |
| 9,295,391 B1 | 3/2016 | Tearney et al. | |
| 9,415,550 B2 | 8/2016 | Tearney et al. | |
| 9,439,570 B2 | 9/2016 | Vertikov | |
| 9,557,154 B2 | 1/2017 | Tearney et al. | |
| 10,288,868 B2 | 5/2019 | Tearney et al. | |
| 2002/0057875 A1* | 5/2002 | Kaneko | G02B 6/12014 385/37 |
| 2002/0197011 A1* | 12/2002 | Liu | G02B 6/124 385/37 |
| 2003/0133658 A1* | 7/2003 | Liu | G02B 6/124 385/37 |
| 2005/0078374 A1 | 4/2005 | Taira et al. | |
| 2005/0179895 A1* | 8/2005 | Puppels | G01J 3/18 356/328 |
| 2007/0188855 A1 | 8/2007 | Shishkov et al. | |
| 2009/0310912 A1* | 12/2009 | Bidnyk | G02B 6/12007 385/27 |
| 2012/0101374 A1 | 4/2012 | Tearney et al. | |
| 2014/0071400 A1 | 3/2014 | Gao | |
| 2014/0132804 A1 | 5/2014 | Guissin et al. | |
| 2014/0160482 A1 | 6/2014 | Tearney et al. | |
| 2014/0254006 A1 | 9/2014 | Weiger | |
| 2014/0276108 A1 | 9/2014 | Vertikov | |
| 2014/0378845 A1 | 12/2014 | Nadkarni | |
| 2016/0341951 A1 | 11/2016 | Tearney et al. | |
| 2016/0349417 A1 | 12/2016 | Tearney et al. | |
| 2016/0374562 A1 | 12/2016 | Vertikov | |
| 2017/0035281 A1 | 2/2017 | Takeuchi et al. | |
| 2017/0167861 A1 | 6/2017 | Chen et al. | |
| 2017/0168232 A1 | 6/2017 | Tearney et al. | |
| 2017/0176736 A1 | 6/2017 | Yamamoto et al. | |
| 2017/0290492 A1 | 10/2017 | Hamm et al. | |
| 2017/0322079 A1 | 11/2017 | Do et al. | |
| 2018/0017778 A1 | 1/2018 | Ikuta et al. | |
| 2018/0214008 A1 | 8/2018 | Yamazoe et al. | |
| 2019/0162977 A1* | 5/2019 | Koyama | G01J 3/024 |
| 2019/0174038 A1* | 6/2019 | Takeuchi | G02B 23/2461 |
| 2019/0339507 A1* | 11/2019 | Ikuta | A61B 1/00096 |
| 2019/0374092 A1* | 12/2019 | Wu | G01J 3/0224 |
| 2020/0018701 A1* | 1/2020 | Meyer | H01S 5/2063 |

FOREIGN PATENT DOCUMENTS

| | | |
|---|---|---|
| WO | 2015/116951 A2 | 8/2015 |
| WO | 2017/024145 A1 | 2/2017 |
| WO | 2017/117203 A1 | 7/2017 |
| WO | 2017/139657 A1 | 8/2017 |
| WO | 2017/165511 A1 | 9/2017 |

OTHER PUBLICATIONS

Chen, et al., "Endoscope Lens with Dual Fields of View and Resolutions for Multiphoton Imaging", Optics Letters, The Optical Society, Washington DC, vol. 35, No. 16, Aug. 2010, pp. 2735-2737.

Zeidan, et al., "Miniature Forward-Viewing Spectrally Encoded Endoscopic Probe", Optics Letters, The Optical Society, Washington DC, vol. 39, No. 16, Aug. 2014, pp. 4871-4874.

Notification of Transmittal of the International Search Report and the Written Opinion of the ISA, and International Search Report and Written Opinion, for PCT/US2018/013192, dated Mar. 23, 2018.

* cited by examiner

SPECTRALLY ENCODED FORWARD VIEW AND SPECTRALLY ENCODED MULTI-VIEW ENDOSCOPE USING BACK-REFLECTED LIGHT BETWEEN REFLECTIVE SURFACES

CROSS-REFERENCE TO RELATED APPLICATION(S)

This application is the National Phase application of PCT Application No. PCT/US2018/013192, filed on Jan. 10, 2018, and relates, and claims priority, to U.S. Patent Application Ser. No. 62/445,465, filed Jan. 12, 2017, the entire disclosures of which applications are incorporated by reference herein in their entireties.

BACKGROUND OF THE INVENTION

Field of the Disclosure

The present disclosure relates to one or more embodiments of spectrally encoded endoscopy (SEE) endoscopes, apparatuses and systems, and methods and storage mediums for use with same. Examples of SEE applications include imaging, evaluating and characterizing/identifying biological objects or tissue, such as, but not limited to, for gastrointestinal, cardio and/or ophthalmic applications.

Description of the Related Art

It is often useful and necessary for medical or research reasons to obtain images from within a subject. An endoscope or some other medical probe has the ability to provide images from inside the subject. The subject may be a human patient. Considering the risk to the subject caused by insertion of a foreign object, it is preferable that the probe be as small as possible. Additionally, the ability to image within small pathways such as vessels, ducts, needles, cuts, cracks etc., provides additional advantages to smaller probe sizes. The ideal medical probe provides as much information with the least amount of disturbance.

One method of speeding up the gathering of information is to encode a component of the spatial information with spectral information. In the context of endoscopy, this is referred to as spectrally encoded endoscopy (SEE), which uses the wavelength of the illumination light to encode spatial information from a sample. Thereby, increasing the speed with which images may be obtained through smaller diameter endoscopic probes.

SEE is a technology that may utilize optical fibers, miniature optics, and a diffraction grating (or prism) for high-speed imaging through small diameter and flexible endoscopic probes. Polychromatic light emanating from the SEE probe is spectrally dispersed and projected in such a way that that each color (wavelength) illuminates a different location on the sample in one line (the dispersive line, spectral line, or illumination line). Reflected (or scattered) light from the sample may be collected and decoded by a spectrometer and/or a detector to form an image line. Each position of the line corresponds with a specific wavelength of the illumination light. Spatial information in another dimension substantially perpendicular to the dispersive line may be obtained by moving the probe. SEE has been used to produce high quality images in two and three dimensions as well as in color. SEE may be accomplished by using a broad bandwidth light input into a single optical fiber. By rotating or swinging the grating back and forth to scan an illumination line along which the light is spectrally dispersed, a two-dimensional image of the sample is obtained.

The geometry of an endoscope requires that the dispersive line be projected in a specific direction relative to the axis of the waveguides in the endoscope. Examples of such directions include forward, side, and backwards. Different directions have different advantages and disadvantages. A diagnostician may use one or more of these views to gather diagnostic information. However, there are a number of challenges associated with a forward-view SEE imaging, including miniaturizing the components, fabrication complexity, and robustness of the SEE probe.

One method of implementing a forward view SEE was described in Costas PITRIS, Brett E. BOUMA, Milen SHISKOV, Guillermo J. TEARNEY, A GRISM-Based Probe for Spectrally Encoded Confocal Microscopy, Optics Express, Jan. 27, 2003, 11(2):120-124, The Optical Society, Washington D.C., 2003. At least one problem with the Pitris design is that the SEE probe is on the order of 10 mm in diameter.

A variation on the Pitris design was disclosed in Adel ZEIDAN, Dvir YELIN, Miniature Forward-Viewing Spectrally Encoded Endoscopic Probe, Optics Letters, Aug. 13, 2014, 39(16):4871-4874, The Optical Society, Washington D.C., 2014 (hereinafter Zeidan). Zeidan is similar to Pitris except that the optics have been reduced down to 1 mm in a diameter. While Zeidan is an improvement on Pitris, the diameter is still at least 1 mm and still requires the use of two prisms and a grating sandwiched between the two prisms. The fabrication and assembly process of at least one endoscope based on the Pitris design is complicated.

A typical SEE utilizes a diffraction grating that deflects incident polychromatic light into different diffraction angles depending upon the wavelength of the light. As the grating diffracts the light, the incident light is typically bent relative to the optical axis. Therefore, light does not typically propagate along the optical axis which can then be used for forward view imaging. In order to direct the light toward the forward view, additional reflective and/or refractive surfaces in the optical system are normally needed to bend the light path before or after being diffracted by the grating. The requirement for additional optics increases the complexity, and cost of the probe while reducing the reliability. A few approaches in probe design have demonstrated forward viewing including the combination of prism and grating, usage of a grating surface facing toward the focusing optics followed by an angled refractive surface. Each of these approaches involves a number of challenges including the complexity in optics and the associated cost, robustness in the assembly, miniaturization, and difficulty in fabrication.

SUMMARY

What is needed is a forward view SEE that is small in size, less complex, has fewer components and is thus more reliable. What is also needed is an SEE that is not limited to just the forward view, but can be used for multiple views including two or more of forward view, side view, and back view. An endoscope that allows for multiple views can enlarge the total field of view and also increase the potential uses in different clinical applications.

There is a need for reducing the size of an endoscopic probe so as to be usable for various subjects and treatment areas in, for example, medical inspection applications and medical applications. Further, in order to confirm the structures of subjects and the structures of treatment areas by using color images, there is a need for acquiring three-color information about the subjects, the three colors being blue, green, and red. In order to acquire a color image by using SEE, a method of illuminating locations on an object to be observed with lights of three colors, blue, green, and red, by superimposing diffracted lights of different diffraction orders on the object to be observed is available. In one or more embodiments, the angle of light incident on a dispersive element and the angles of exiting diffracted lights may differ considerably from each other, as a result of which the size of an optical apparatus and/or system at an end of the probe is increased.

At least one broad feature(s) of the present disclosure is to provide an endoscope, a probe, and an image acquisition apparatus in SEE for acquiring color images with a miniaturized probe. At least a further broad feature(s) of the present disclosure to provide SEE apparatuses, systems, methods, and storage mediums for use with same. At least one example may be an endoscope. The endoscope may include a first waveguide for guiding light from a light source to an output port of the first waveguide. The endoscope may include an optical apparatus and/or system. The optical apparatus and/or system may comprise at least a first reflecting surface and a second reflecting surface. The endoscope may include a diffraction grating. The first reflecting surface may be arranged to reflect light from the output port of the first waveguide to the second reflecting surface. The second reflecting surface may be arranged to reflect light from the first reflecting surface back through the first reflecting surface to the diffraction grating. The diffraction grating may diffract light from the second reflecting surface in a non-zero diffraction order in a first direction. In one or more embodiments, the diffraction grating may diffract light from the second reflecting surface in blue, green and red wavelength lights of non-zero diffraction orders, which are mutually different in the diffraction order, in a first direction. The apparatus and/or system may be used to obtain a two or three dimensional image in black and white or in color.

In at least one embodiment of the present disclosure, the first reflecting surface may be a total internal reflecting surface for at least a portion of light that the first reflecting surface receives from the output port of the first waveguide.

In at least one embodiment of the present disclosure, the first reflecting surface and a portion of the diffraction grating component may be on the same plane and both may be on a single support structure.

In at least one embodiment of the present disclosure, the second reflecting surface may be a curved surface.

In at least one embodiment of the present disclosure, the optical apparatus and/or system may further comprise a spacer located between the output port of the first waveguide and the first reflecting surface.

In at least one embodiment of the present disclosure, the spacer may be a GRIN lens.

In at least one embodiment of the present disclosure, an optical axis of the first waveguide may be co-linear with an optical axis of the GRIN lens.

In at least one embodiment of the present disclosure, an end portion of the endoscope may be between the output port of the first waveguide and an illumination surface; the illumination surface may be a final surface of the endoscope out of which illumination light exits the endoscope; and a diameter of an end portion of the endoscope may be less than 350 µm.

In at least one embodiment of the present disclosure, the endoscope may have a plurality of propagation modes. In a first propagation mode among the plurality of propagation modes, light from the output port of the first waveguide may be reflected by the first reflecting surface, then reflected by the second reflecting surface, and may then diffracted by the diffraction grating. In a second propagation mode among the plurality of propagation modes, light from the output port of the first waveguide may be diffracted by the diffraction grating and may not be reflected by the first reflecting surface or the second reflecting surface.

At least one embodiment of the present disclosure may further comprise a detector and a switch.

In at least one embodiment of the present disclosure, the first reflecting surface may be configured to receive light from the output port at a first angle with respect to a normal of the first reflecting surface. The first angle may be greater than a critical angle for total internal reflection.

In at least one embodiment of the present disclosure, the first reflecting surface and the diffraction grating component may be on substantially parallel planes.

In at least one embodiment of the present disclosure, the first reflecting surface may be an interface between a single support structure and a thin film or layer and the diffraction grating may be on the thin film or layer.

In at least one embodiment of the present disclosure, the second reflecting surface may be a surface of a ball lens.

At least a second example may be an imaging apparatus. The imaging apparatus may comprise: a light source; a detector; a first waveguide for guiding light from the light source to an output port of the first waveguide; an optical apparatus and/or system; a diffraction grating; and a second waveguide for gathering light and sending the gathered light to the detector. The optical apparatus and/or system may comprise at least a first reflecting surface and a second reflecting surface. The first reflecting surface may be arranged to reflect light from the output port of the first waveguide to the second reflecting surface. The second reflecting surface may be arranged to reflect light from the first reflecting surface back through the first reflecting surface to the diffraction grating. The diffraction grating may diffract light from the second reflecting surface in a non-zero diffraction order in a first direction.

In at least the second embodiment of the present disclosure, the first reflecting surface may be a total internal reflecting surface for at least a portion of light that the first reflecting surface receives from the output port of the first waveguide.

In at least the second embodiment of the present disclosure, the first reflecting surface and a portion of the diffraction grating component may be on the same plane and both may be on a single support structure.

In at least the second embodiment of the present disclosure, the second reflecting surface may be a curved surface.

In at least the second embodiment of the present disclosure, the imaging apparatus and/or system may have a plurality of propagation modes. In a first propagation mode among the plurality of propagation modes, light from the output port of the first waveguide may be reflected by the first reflecting surface, may then reflected by the second reflecting surface, and may then diffracted by the diffraction grating. In a second propagation mode among the plurality of propagation modes, light from the output port of the first waveguide may be diffracted by the diffraction grating and may not be reflected by the first reflecting surface or the second reflecting surface.

At least the second embodiment of the present disclosure may further comprise a switch.

In at least the second embodiment of the present disclosure, the first reflecting surface may be configured to receive light from the output port at a first angle with respect to a normal of the first reflecting surface. The first angle may be greater than a critical angle for total internal reflection.

In at least the second embodiment of the present disclosure, the first reflecting surface and the diffraction grating component may be on substantially parallel planes.

In at least the second embodiment of the present disclosure, the first reflecting surface may be an interface between a single support structure and a thin film and the diffraction grating may be on the thin film.

In at least the second embodiment of the present disclosure, the second reflecting surface may be a surface of a ball lens.

At least a third embodiment example may be a probe. One or more embodiments of a probe may comprise: a first waveguide for guiding light from a light source to an output port of the first waveguide; an optical apparatus and/or system; and a diffraction grating. The optical apparatus and/or system may comprise at least a first reflecting surface and a second reflecting surface. The first reflecting surface may be arranged to reflect light from the output port of the first waveguide to the second reflecting surface. The second reflecting surface may be arranged to reflect light from the first reflecting surface back through the first reflecting surface to the diffraction grating. The diffraction grating may diffract light from the second reflecting surface in a non-zero diffraction order in a first direction. In one or more embodiments, as aforementioned, the diffraction grating may diffract light from the second reflecting surface in blue, green and red wavelength lights of non-zero diffraction orders, which are mutually different in the diffraction order, in a first direction.

In at least the third embodiment of the present disclosure, the first reflecting surface may be a total internal reflecting surface for at least a portion of light that the first reflecting surface receives from the output port of the first waveguide.

In at least the third embodiment of the present disclosure, the first reflecting surface and a portion of the diffraction grating component may be on the same plane and may be both on a single support structure.

In at least the third embodiment of the present disclosure, the second reflecting surface may be a curved surface.

In at least the third embodiment of the present disclosure, the probe may have a plurality of propagation modes. In a first propagation mode among the plurality of propagation modes, light from the output port of the first waveguide may be: reflected by the first reflecting surface, then reflected by the second reflecting surface, and then diffracted by the diffraction grating. In a second propagation mode among the plurality of propagation modes, in one or more embodiments, light from the output port of the first waveguide may be diffracted by the diffraction grating and may not be reflected by the first reflecting surface or the second reflecting surface.

At least the third embodiment may further comprise a detector and a switch.

In at least the third embodiment of the present disclosure, the first reflecting surface may be configured to receive light from the output port at a first angle with respect to a normal of the first reflecting surface. The first angle may be greater than a critical angle for total internal reflection.

In at least the third embodiment of the present disclosure, the first reflecting surface and the diffraction grating component may be on substantially parallel planes.

In at least the third embodiment of the present disclosure, the first reflecting surface may be an interface between a single support structure and a thin film and the diffraction grating may be on the thin film.

In at least the third embodiment of the present disclosure, the second reflecting surface may be a surface of a ball lens.

A fourth embodiment of the present disclosure may be a spectral encoding probe. At least one spectral encoding probe may comprise: a first waveguide for guiding light from a light source to an output port of the first waveguide; an optical apparatus and/or system; and a diffraction grating. The optical apparatus and/or system may comprise at least a first reflecting surface and a second reflecting surface. The first reflecting surface may be arranged to reflect light from the output port of the first waveguide to the second reflecting surface. The second reflecting surface may be arranged to reflect light from the first reflecting surface to the diffraction grating. The diffraction grating may diffract light from the second reflecting surface in a non-zero diffraction order in a first direction. In one or more embodiments, as aforementioned, the diffraction grating may diffract light from the second reflecting surface in blue, green and red wavelength lights of non-zero diffraction orders, which are mutually different in the diffraction order, in a first direction.

In at least the fourth embodiment of the present disclosure, the first reflecting surface may be a total internal reflecting surface for at least a portion of light that the first reflecting surface receives from the output port of the first waveguide.

In at least the fourth embodiment of the present disclosure, the second reflecting surface may be a total internal reflecting surface for at least a portion of light that the second reflecting surface receives from the first reflecting surface.

In at least the fourth embodiment of the present disclosure, the first reflecting surface may be a curved surface.

In at least the fourth embodiment of the present disclosure, the second reflecting surface may be a curved surface.

At least the fourth embodiment may further comprise a spacer located between the output port of the first waveguide and the first reflecting surface.

In at least the fourth embodiment of the present disclosure, the spacer may be a GRIN lens.

In at least the fourth embodiment of the present disclosure, an optical axis of the first waveguide may not be co-linear with an optical axis of the GRIN lens.

In at least the fourth embodiment of the present disclosure, an end portion of the spectral encoding probe may be between the output port of the first waveguide and an illumination surface. The illumination surface may be a final surface of the spectral encoding probe out of which illumination light exits the spectral encoding probe. A diameter of an end portion of the spectral encoding probe may be less than 350 µm.

In at least the fourth embodiment of the present disclosure, the first reflecting surface may be a surface of a ball lens.

In at least the fourth embodiment of the present disclosure, the second reflecting surface may be a surface of a ball lens.

A fifth embodiment example of the present disclosure may be a probe. At least one probe may comprise a first waveguide and an optical apparatus and/or system. The optical apparatus and/or system may comprise at least: a first reflecting surface; a second reflecting surface; and a diffraction grating. The diffraction grating may receive light and may be arranged to diffract the received light through the first reflecting surface. The second reflecting surface may be arranged to receive diffracted light which passed through the first reflecting surface that was diffracted by the diffraction grating and may reflect the diffracted light back towards the first reflecting surface. The first reflected surface may be arranged to reflect the diffracted light from the second reflecting surface towards the first waveguide. The first waveguide may be arranged to receive the diffracted light that the first reflecting surface reflects from the second reflecting surface.

In at least the fifth embodiment of the present disclosure, the second reflecting surface may be a curved surface.

At least the fifth embodiment may further comprise a spacer located between the output port of the first waveguide and the first reflecting surface.

In at least the fifth embodiment of the present disclosure, the spacer may be a GRIN lens.

In at least the fifth embodiment of the present disclosure, an optical axis of the first waveguide may be co-linear with an optical axis of the GRIN lens.

In at least the fifth embodiment of the present disclosure, the first reflecting surface may be configured to receive light from the second reflecting surface at a first angle with respect to a normal of the first reflecting surface. The first angle may be greater than a critical angle for total internal reflection.

In at least the fifth embodiment of the present disclosure, the first reflecting surface and the diffraction grating component may be on substantially parallel planes.

In at least the fifth embodiment of the present disclosure, the first reflecting surface may be an interface between a single support structure and a thin film and the diffraction grating may be on the thin film.

In at least the fifth embodiment of the present disclosure, the second reflecting surface may be a surface of a ball lens.

At least a sixth embodiment example may be a probe. At least one probe may comprise: a first waveguide for guiding light from a light source to an output port of the first waveguide; and an optical apparatus and/or system. The optical apparatus and/or system may comprise at least: a first reflecting surface; a second reflecting surface; a first diffraction grating; and a second diffraction grating. The first reflecting surface may be arranged to reflect light from the output port of the first waveguide to the second reflecting surface. The second reflecting surface may be arranged to reflect a first portion of light from the first reflecting surface towards a first diffraction grating. The second reflecting surface may be arranged to transmit a second portion of the light from the first reflecting surface through a second diffraction grating. The first diffraction grating may diffract light reflected from the second reflecting surface in a non-zero diffraction order in a first direction. The second diffraction grating may diffract light transmitted through the second reflecting surface in a non-zero diffraction order in a second direction different from the first direction. In one or more embodiments, the first diffraction grating and/or the second diffraction grating may diffract light from the second reflecting surface and/or through the second reflecting surface, respectively, in blue, green and red wavelength lights of non-zero diffraction orders, which are mutually different in the diffraction order, in a first direction and in a second direction different from the first direction, respectively.

In at least the sixth embodiment of the present disclosure, the first reflecting surface may be a total internal reflecting surface for at least a portion of light that the first reflecting surface receives from the output port of the first waveguide.

In at least the sixth embodiment of the present disclosure, the first reflecting surface may be a curved surface.

At least the sixth embodiment may further comprise a spacer located between the output port of the first waveguide and the first reflecting surface.

In at least the sixth embodiment of the present disclosure, the spacer may be a GRIN lens.

In at least the sixth embodiment of the present disclosure, an optical axis of the first waveguide may not be co-linear with an optical axis of the GRIN lens.

In at least the sixth embodiment of the present disclosure, the second reflecting surface and the second diffraction grating component may be on substantially parallel planes.

In at least the sixth embodiment of the present disclosure, the second reflecting surface may be an interface between a single support structure and a thin film and the second diffraction grating may be on the thin film.

In at least the sixth embodiment of the present disclosure, the first reflecting surface may be a surface of a ball lens.

In one or more embodiments of the present disclosure, it is possible to, in Spectrally encoded endoscopy (SEE), reduce the size of the optical apparatus and/or system at the end of the probe and acquire black and white and/or color images.

According to other aspects of the present disclosure, one or more additional apparatuses, one or more systems, one or more methods, and one or more storage mediums using SEE technique(s) are discussed herein. Further features of the present disclosure will become apparent from the following description of exemplary embodiments with reference to the attached drawings.

BRIEF DESCRIPTION OF THE DRAWINGS

For the purposes of illustrating various aspects of the disclosure, wherein like numerals indicate like elements, there are shown in the drawings simplified forms that may be employed, it being understood, however, that the disclosure is not limited by or to the precise arrangements and instrumentalities shown. To assist those of ordinary skill in the relevant art in making and using the subject matter hereof, reference is made to the appended drawings and figures, wherein.

DETAILED DESCRIPTION OF THE EMBODIMENTS

Embodiments will be described below with reference to the attached drawings. Like numbers refer to like elements throughout. It shall be noted that the following description is merely illustrative and exemplary in nature, and is in no way intended to limit the disclosure and its applications or uses. The relative arrangement of components and steps, numerical expressions and numerical values set forth in the embodiments do not limit the scope of the disclosure unless it is otherwise specifically stated. Techniques, methods, and devices which are well known by individuals skilled in the art may not have been discussed in detail since an individual skilled in the art would not need to know these details to enable the embodiments discussed below. Further, an endoscope as disclosed in the following which is used to inspect an inside a human body may also be used to inspect other objects. Examples of specialized endoscopes which are examples of endoscope in which an embodiment may be implemented including: angioscope; anoscope; arthroscope; arterioscope; arthroscope, bronchoscope; capsule endoscope; choledochoscope; colonoscope; colposcope; cystoscope; encephaloscope; esophagogastroduodenoscope; esophagoscope; gastroscope; hysteroscope; laparoscope; laryngoscope; mediastinoscope; nephroscope; neuroendoscope; proctoscope; resectoscope; rhinoscope; sigmoidoscope; sinusoscope; thoracoscope; ureteroscope; uteroscope; borescope; fiberscope; inspection camera; and any specialized endoscope which may be adapted to include an embodiment. The endoscope may be flexible or rigid. An embodiment may also be a probe or an imaging apparatus.

One or more devices, optical systems, methods, and storage mediums for improving resolution of an image of a subject, such as tissue, using a SEE technique and/or for obtaining a black and white image and/or a color image using a SEE technique are disclosed herein. In accordance with at least one aspect of the present disclosure, one or more devices, optical systems, methods, and storage mediums discussed herein use a SEE technique to improve image resolution and/or to obtain images in black and white and/or color while improving the resolution.

Figure 1A:
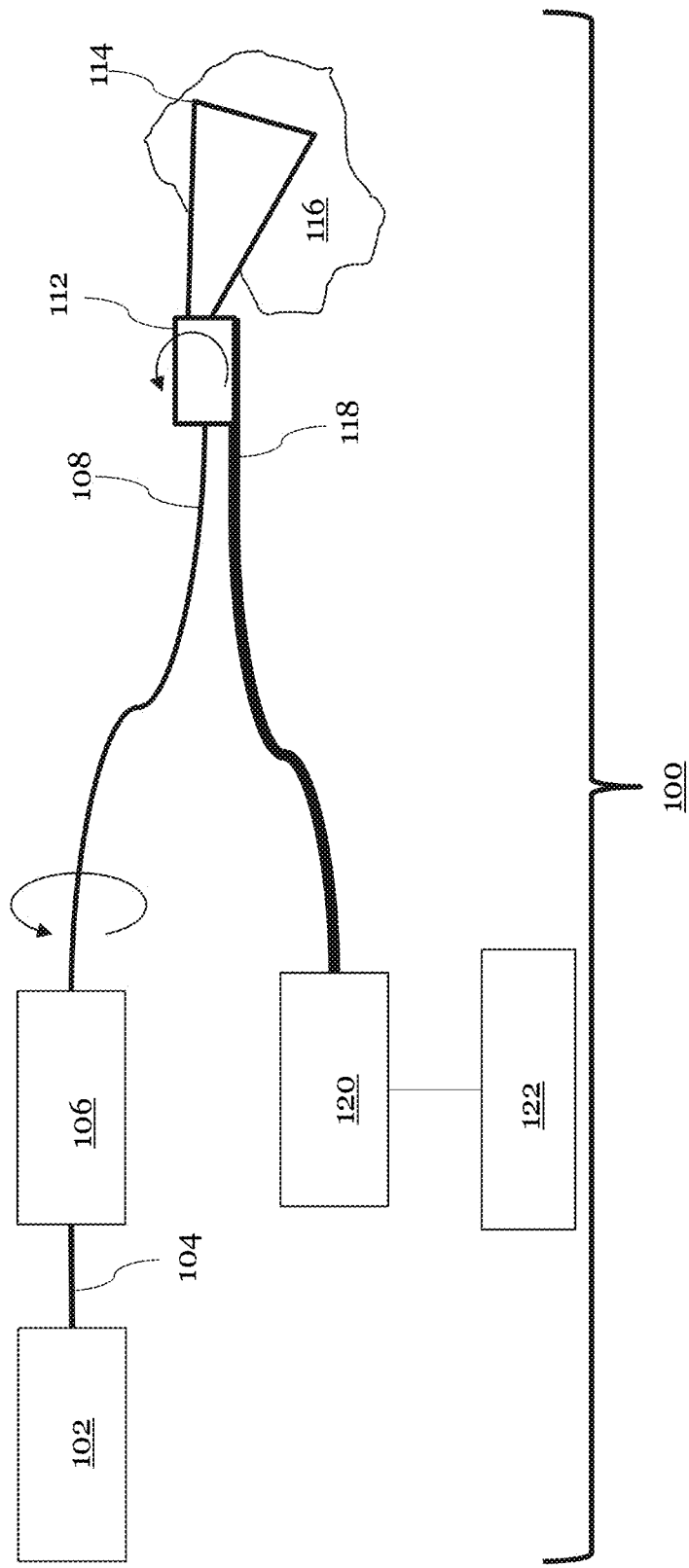
FIG. 1A is an illustration of at least one embodiment of a SEE system.

FIG. 1A is an illustration of at least a first embodiment (with a further or alternative embodiment being shown in FIG. 1B and an even further or other alternative embodiment being shown in FIG. 1C as discussed below), such as an endoscope 100 in which one or more of the features of the subject embodiment may be implemented. The endoscope 100 may include or be connected to a broadband light source 102. The broadband light source 102 may include a plurality of light sources or may be a single light source. The broadband light source 102 may include one or more of a laser, an organic light emitting diode (OLED), a light emitting diode (LED), a halogen lamp, an incandescent lamp, supercontinuum light source pumped by a laser, and/or a fluorescent lamp. The broadband light source 102 may be any light source that provides light which may then be dispersed to provide light which is then used to for spectral encoding of spatial information. The broadband light source 102 may be fiber coupled or may be free space coupled to the other components of the endoscope 100 or any other embodiment (including, but not limited to, systems 100' (see FIG. 1B), 100" (see FIG. 1C), etc.) discussed herein.

The endoscope 100 may include a rotary junction 106. The connection between the light source 102 and the rotary junction 106 may be a free space coupling or a fiber coupling via fiber 104. The rotary junction 106 may supply just illumination light via the rotary coupling or may supply one or more of illumination light, power, and/or sensory signal lines.

The rotary junction 106 couples the light to a first waveguide 108. In one embodiment, the first waveguide 108 is a single mode fiber, a multimode fiber, or a polarization maintaining fiber.

The first waveguide 108 is coupled to an optical apparatus and/or system 112. The optical apparatus and/or system 112 may include one or more optical components, that refract, reflect, and disperse the light from the first waveguide 108 to form a line of illumination light 114 on a sample 116. In an embodiment, the line of illumination light 114 is a line connecting focal points for a wavelength range as the illumination light exits the optical apparatus and/or system 112, the wavelength range being determined by the light source 102. In another embodiment, the spectrometer 120 may further limit the wavelength range by only using information from specified wavelengths of interest. In another embodiment, the line of illumination light 114 is a line formed by the illumination light as the illumination light intersects a surface of the sample 116 for the range of wavelengths that are detected by the spectrometer 120. In another embodiment, the line of illumination light 114 is a line of illumination light in a wavelength range formed on a specific image plane which is determined by the detection optics. In one or more embodiments, only some of the points on the image line may be in focus while other points on the image line may not be in focus. The line of illumination light 114 may be straight or curved.

In an alternative embodiment, the optical apparatus and/or system 112 may partially collimate the light from the waveguide 108 such that the light is focused onto the sample 116 but the light is substantially collimated at a dispersive optical element such as a grating.

The apparatus 100 may include a detection waveguide 118. The detection waveguide 118 may be a multimode fiber, a plurality of multimode fibers, a fiber bundle, a fiber taper, or some other waveguide. The detection waveguide 118 gathers light from the sample 116 which has been illuminated by light from the optical apparatus and/or system 112. The light gathered by the detection waveguide 118 may be reflected light, scattered light, and/or fluorescent light. In one embodiment, the detection waveguide 118 may be placed before or after a dispersive element of the optical apparatus and/or system 112. In one embodiment, the detection waveguide 118 may be covered by the dispersive element of the optical apparatus and/or system 112, in which case the dispersive element may act as wavelength-angular filter. In another embodiment, the detection waveguide 118 is not covered by the dispersive element of the optical apparatus and/or system 112. The detection waveguide 118 guides detection light from the sample 116 to a spectrometer 120.

The spectrometer 120 may include one or more optical components that disperse light and guide the detection light from the detection waveguide 118 to one or more detectors. The one or more detectors may be a linear array, a charge-coupled device (CCD), a plurality of photodiodes or some other method of converting the light into an electrical signal. The spectrometer 120 may include one or more dispersive components such as a prisms, gratings, or grisms. The spectrometer 120 may include optics and opto-electronic components which allow the spectrometer 120 to measure the intensity and wavelength of the detection light from the sample 116. The spectrometer 120 may include an analog to digital converter (ADC).

The spectrometer 120 may transmit the digital or analog signals to a processor or a computer such as, but not limited to, an image processor 122, or a processor or computer 1300, 1300' (see e.g., FIGS. 1B-1C), a combination thereof, etc. The image processor 122 may be a dedicated image processor or a general purpose processor that is configured to process images. In at least one embodiment, the computer 1300, 1300' may be used in place of the image processor 122. In an alternative embodiment, the image processor 122 may include an ADC and receive analog signals from the spectrometer 120. The image processor 122 may include one or more of a CPU, DSP, FPGA, ASIC, or some other processing circuitry. The image processor 122 may include memory for storing image, data, and instructions. The image processor 122 may generate one or more images based on the information provided by the spectrometer 120. A computer or processor discussed herein, such as, but not limited to, the computer 1300, the computer 1300', the image processor 122, may also include one or more components further discussed herein below (see e.g., FIGS. 31-32).

One or more components of the endoscope 100 may be rotated via the rotary junction 106, or oscillated so as to scan a line of illumination light 114 so as to create a 2D array of illumination light. A 2D image may be formed by scanning a spectrally encoded line from the optical apparatus and/or system 112 across the sample 116. The endoscope 100 may include an additional rotary junction that couples the light from the detection fiber 118 to the spectrometer 120. Alternatively, the spectrometer 120 or a portion of the spectrometer 120 may rotate with the fiber 118. In an alternative embodiment, there is no rotary junction 106 and the light source rotates with the fiber 108. An alternative embodiment may include an optical component (mirror) after a dispersive element in the optical system 112 which rotates or scans the spectrally encoded line of illumination light across the sample 116 substantially perpendicular to the spectrally encoded line of illumination light 114 in a linear line to produce a 2D image or circumferentially in a circle so as to produce a toroidal image. Substantially, in the context of one or more embodiments of the present disclosure, means within the alignment and/or detection tolerances of the endoscope 100, the system 100', the system 100" and/or any other system being discussed herein. In an alternative embodiment, there is no rotary junction 106 and an illumination end of the optical apparatus and/or system 112 is scanned or oscillated in a direction perpendicular to the illumination line.

Figure 2:
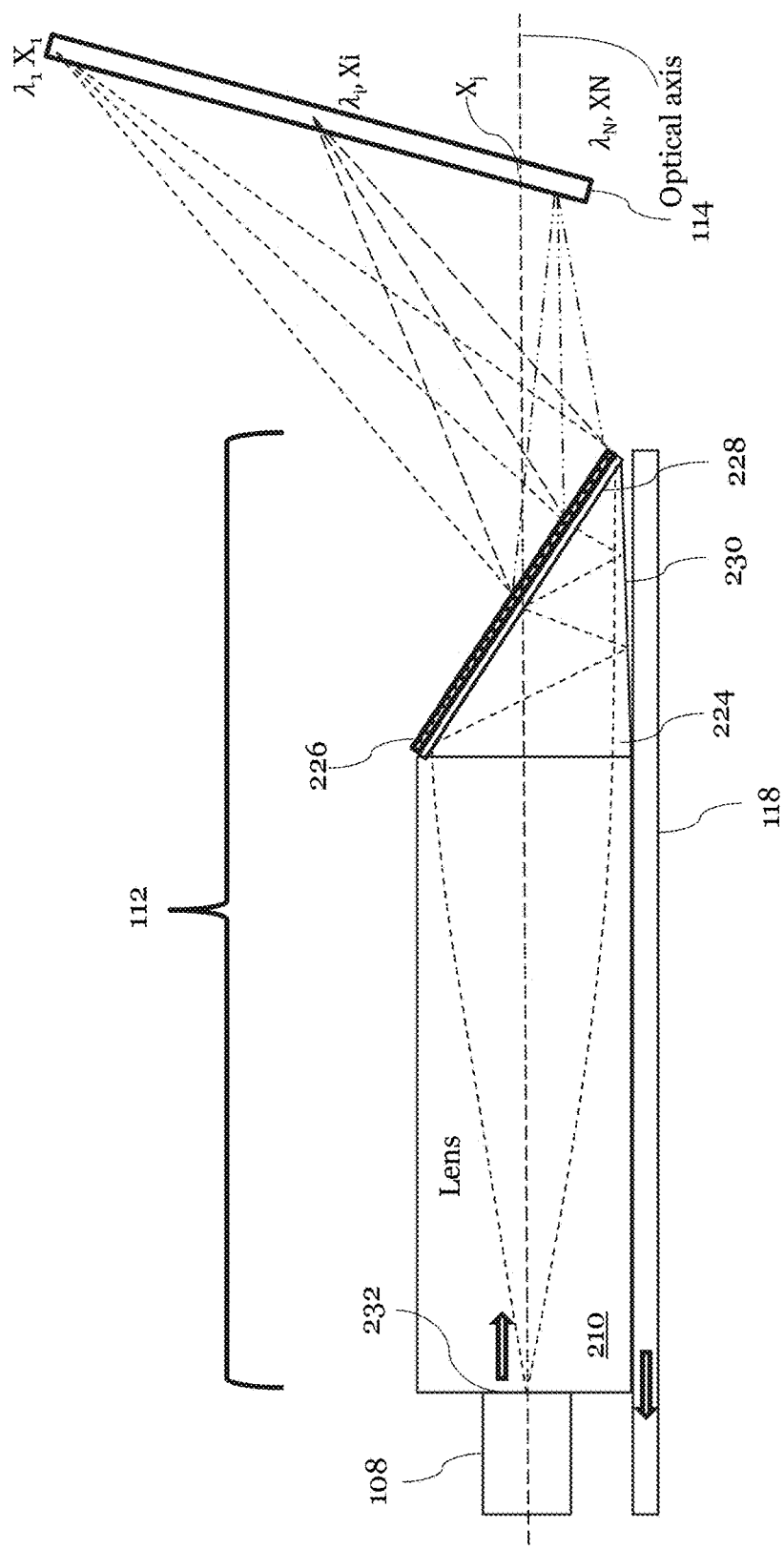
FIG. 2 is an illustration of a portion of an embodiment

FIG. 2 is an illustration of an end portion of a front view SEE that includes: the first waveguide 108 for guiding illumination light from the light source 102; the second waveguide 118 for gathering the detection light, and an optical system 112. The optical system 112 may include a lens 210 which may be GRIN lens. The optical system 112 may also include a first reflecting surface 228, a second reflecting surface 230, and a dispersive element 226 (i.e., a diffraction grating).

Figure 1B:
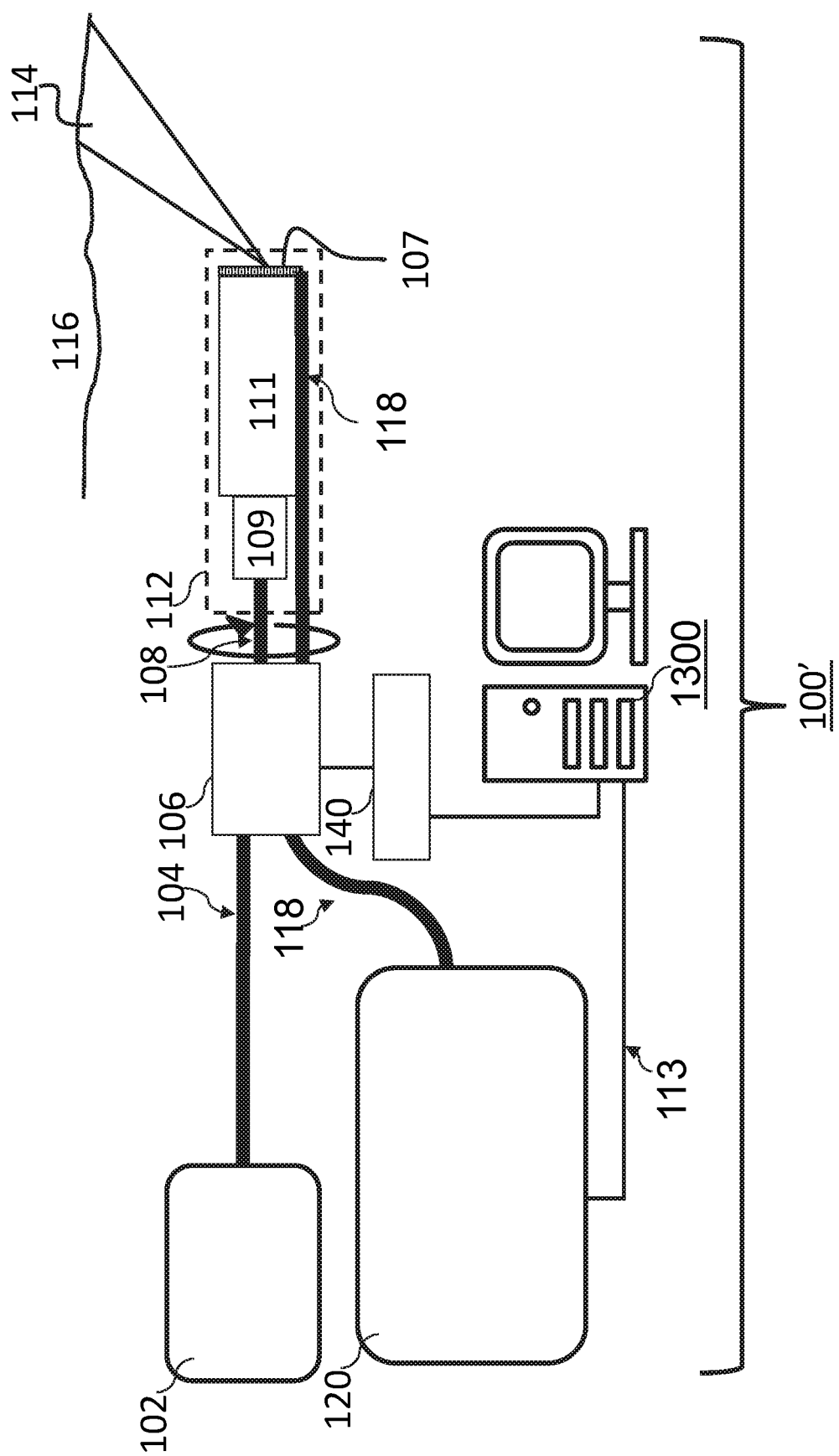
FIG. 1B is a schematic diagram of at least one another embodiment of a SEE system.
Figure 1C:
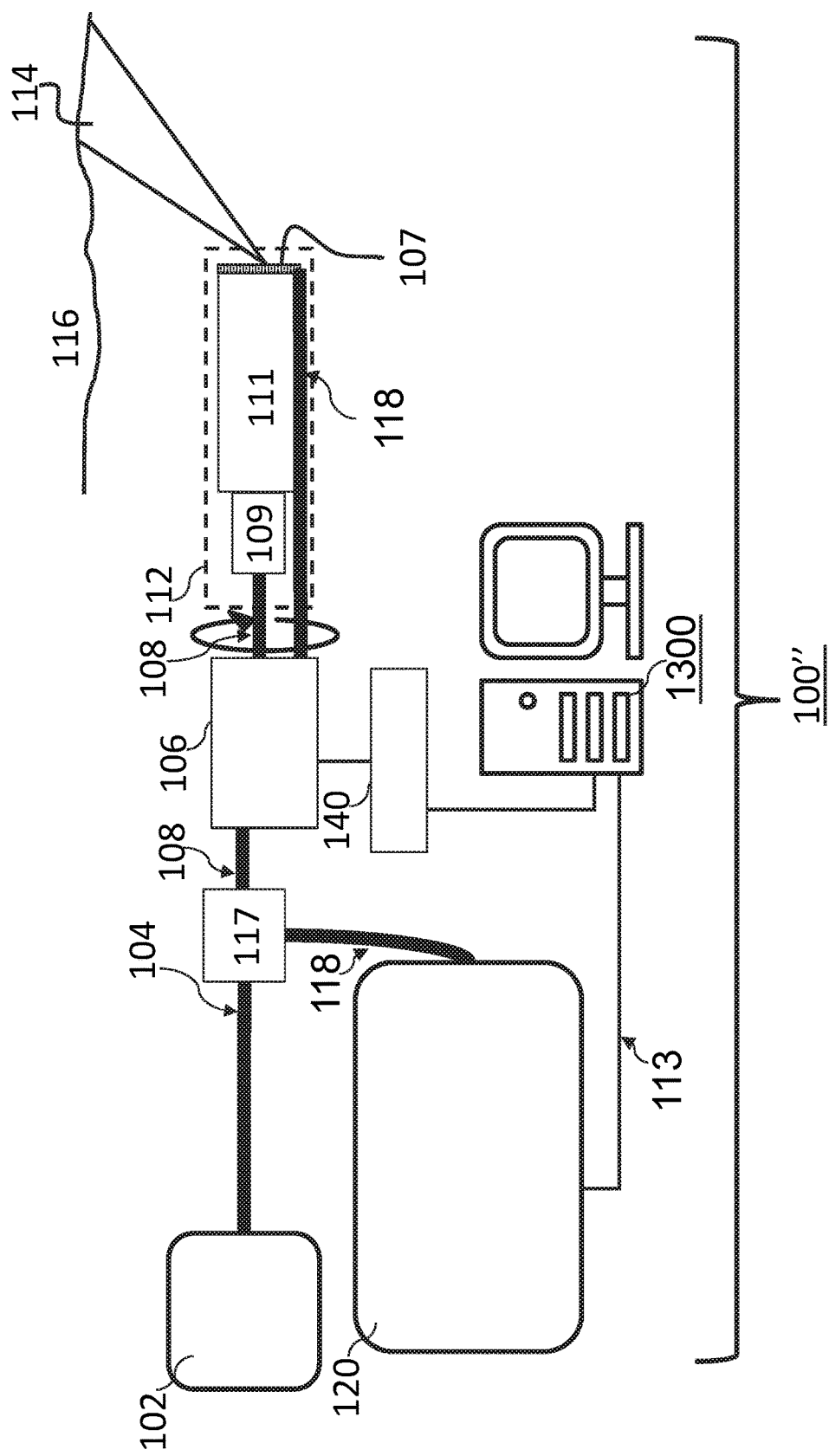
FIG. 1C is a schematic diagram of at least a further embodiment of a SEE system.

In one or more alternative embodiments, a dispersive element 107 (i.e., a diffraction grating) may be used in the optical apparatus and/or system 112 as shown, respectively, in FIGS. 1B and 1C. In one or more embodiments (best seen in FIGS. 1B and 1C), light that has been emitted from the core of the end portion of the illumination optical fiber or the first waveguide 108 may enter a spacer 111 via a refractive-index distribution lens (hereinafter referred to as "gradient index (GRIN) lens") 109 (alternatively, in one or more embodiments, the lens 210 of FIG. 2 may be used as the GRIN lens). The diffraction grating 107 is formed at the tip portion of the spacer 111 as shown in FIGS. 1B and 1C, and a spectral sequence 114 is formed on the subject or sample 116 by a light flux of white light entering the diffraction grating 107. FIG. 1C illustrates an alternative embodiment of a SEE system 100" including a spectrometer as shown in FIG. 1B (see e.g., system 100'), with the exception being that a deflecting or deflected section 117 is incorporated into the system 100' of FIG. 1B such that the cable or fiber 104 and/or the cable or fiber 108 connecting the light source 102 to the rotary junction 106 and/or the optical apparatus and/or system 112 and the cable or fiber 118 connecting the spectrometer 120 to the rotary junction 106 and/or the optical apparatus and/or system 112 pass through, and are connected via, the deflected section 117 (discussed further below).

In at least one embodiment, a console or computer 1300, 1300' operates to control motions of the RJ 106 via a Motion Control Unit (MCU) 140, acquires intensity data from the detector(s) in the spectrometer 120, and displays the scanned image (e.g., on a monitor or screen such as a display, screen or monitor 1309 as shown in the console 1300 of FIG. 31 and/or the console 1300' of FIG. 32 as further discussed below). In one or more embodiments, the MCU 14o operates to change a speed of a motor of the RJ 106 and/or of the RJ 106. The motor may be a stepping or a DC servo motor to control the speed and increase position accuracy. In one or more embodiments, the deflection or deflected section 117 may be at least one of: a component that operates to deflect the light from the light source to the interference optical system, and then send light received from the interference optical system towards the at least one detector; a deflection or deflected section that includes at least one of: one or more interferometers, a circulator, a beam splitter, an isolator, a coupler, a fusion fiber coupler, a partially severed mirror with holes therein, and a partially severed mirror with a tap; etc. In one or more other embodiments, the rotary junction 106 may be at least one of: a contact rotary junction, a lenseless rotary junction, a lens-based rotary junction, or other rotary junction known to those skilled in the art.

In an embodiment, the first waveguide 108 may be single mode fiber. In an alternative embodiment, the first waveguide 108 may be a multimode fiber or a double clad fiber. In an embodiment, the second waveguide 118 may be a multi-mode fiber a single mode fiber, or a fiber bundle.

In an alternative embodiment, the first waveguide 108 may be an inner core of a double-clad fiber, while the second waveguide 118 may be between the inner core and the outer cladding of the double clad fiber. If a double clad fiber is used, an alternative embodiment may include an optical coupler for guiding illumination light to the inner core, and the optical coupler may also receive detection light from the outer waveguide which is then guided to the spectrometer 120.

The lens 210 may be attached to an end of an optical component that includes the first reflecting surface 228 and the second reflecting surface 230. The first reflecting surface 228 may be a total internal reflecting (TIR) surface. The first reflecting surface 228 may be a surface that reflects light from an output port 232 of the first waveguide 108. Light that exits the output port 232 of the first waveguide 10o8 may pass through the lens 210 before being reflected by the first reflecting surface 228. The first reflecting surface 228 and the dispersive element 226 may be on substantially the same plane and may both be on a single support structure 224. The first reflecting surface 228 is an interface between the single support structure 224 and a second optical structure with one or more optical properties which are different the optical properties of the single support structure 224. The dispersive element 226 may be coupled to the second optical structure. A plane of the dispersive element 226 may be substantially parallel to a plane of the first reflecting surface 228. The plane of the dispersive element 226 may be separated from the plane of the first reflecting surface by a narrow sub-micron gap. The second optical structure may be a thin film or layer.

The first reflecting surface 228 may be an interface between a low refractive index material (thin film or layer) or an air-gap that exists between the grating and the single support structure 224 creating an interface for the TIR. The thickness of the low index thin film or layer needs to be larger than a thickness d as defined in the following formula (1) below.

$$d = \frac{\lambda}{4\pi n_1(\lambda)\sqrt{\sin^2\theta_1 - \left(\frac{n_2(\lambda)}{n_1(\lambda)}\right)^2}} \quad (1)$$

For equation (1): $\lambda$ is the longest wavelength of the illumination light which may be 800 nm in an embodiment; $\theta_1$ is the incidence angle of the illumination light relative to a normal of the first reflecting surface 228; $n_1(\lambda)$ is the refractive index of the single support structure 224 at the wavelength A; $n_2(\lambda)$ is the refractive index on the other side of the first reflecting surface 228 at the wavelength A; d is a lower bound for the thickness of the thin film or layer 334 that forms the first reflecting surface 228 interface with the single support structure 224. In an embodiment, $n_1(\lambda) > n_2(\lambda)$. The normal range for the thickness d is 30 nm to 500 nm. For example at least an embodiment may have the following conditions: $n_1(\lambda)$ is 1.65; $n_2(\lambda)$ is 1.4; and $\theta_1$ is 60°. When the wavelength $\lambda$ is 400 nm then d is 111 nm, and when the wavelength $\lambda$ is 800 nm then d is 222 nm. In one or more embodiments, for the TIR to occur, $$\theta_i > \sin^{-1}\left(\frac{n_2(\lambda)}{n_1(\lambda)}\right);$$

$\theta_i$ is the incidence angle of the illumination light relative to a normal of the first reflecting surface 228; $n_1(\lambda)$ is the refractive index of the single support structure 224 at the wavelength $\lambda$, $n_2(\lambda)$ is the refractive index on the other side of the first reflecting surface 228 at the wavelength $\lambda$. The thin layer 334 forms the first reflecting surface 228 interface with the single support structure 224. For example at least an embodiment may have the following conditions: $n_1(\lambda_d)$ is 2.0509; $n_2(\lambda_d)$ is 1.5037; and $\theta_i$ is 49.5°, wherein $\lambda_d$ is wavelength of d-line. In an embodiment, $n_1(\lambda) > n_2(\lambda)$. Taking into consideration the ease of fabrication of the grating 226 on the single support structure 224, the preferred range for the thickness d of the thin layer 334 is 3 um to 30 um. In an embodiment, the thin film or layer 334 and the grating 226 are combined together into a single structure, in which the thickness d is in reference to a base of the grating 226 below the grooves.

The second reflecting surface 230 may be a TIR surface or a mirror coated surface of the single support structure 224. Light from the broadband light source 102 comes through the first waveguide 108 and into the lens 210. Light is mostly collimated when it is incident on the first reflecting surface 228. The lens 210 may be a quarter pitch, a 0.22 pitch, or other pitch GRIN lens. The first reflecting surface 228 and the second reflecting surface 230 reflect the illumination light twice before it is dispersed (diffracted) by the dispersive element 226 (grating).

The broadband light source 102 has light with different wavelengths $(\lambda_{B1}, \lambda_{Bi}, \ldots, \lambda_{BN}, \lambda_{G1}, \lambda_{Gi}, \ldots, \lambda_{GN}, \lambda_{R1}, \lambda_{Ri}, \ldots, \lambda_{RN})$ and $(\lambda_{B1} < \lambda_{Bi} < \lambda_{BN} < \lambda_{G1} < \lambda_{Gi} < \lambda_{GN} < \lambda_{R1} < \lambda_{Ri} < \lambda_{RN})$ are diffracted onto different locations $(X_1, X_i, \ldots, X_N)$ on the sample 116 in a line 114 as illustrated in FIG. 2. Here, B, G, and R denote a wavelength band for blue, a wavelength band for green, and a wavelength band for red, respectively. By superimposing diffracted lights of a plurality of diffraction orders, an illumination light column 114 shown in FIG. 2 can be formed. For example, for the wavelength band for blue, a −6th order light is used; for the wavelength band for green, a −5th order light is used; and for the wavelength band for red, a −4th order light is used. At least one of the wavelengths $\lambda_j$ propagates parallel to a point $X_j$ that is an intersection of the line 114 and the optical axis of the lens 210. In an embodiment, $X_j=X_1$.

Light reflected, scattered, or fluoresced from the sample 116 may be gathered by the second waveguide 118 and may be delivered to the spectrometer 120.

One or more components of the SEE may be moved or rotated to acquire a two dimensional image of the sample 116. In an embodiment, the first waveguide 108, the second waveguide 118, and the optical system 112 are rotated or scanned. In an embodiment, the first waveguide 108 and the optical system 112 are rotated or scanned. In an embodiment, the optical system 112 is rotated or scanned. In an embodiment, the lens 210, the second waveguide 118, and the single support structure 224 are rotated or scanned. In an embodiment, the lens 210 and the single support structure 224 are rotated or scanned. In an embodiment, the single support structure 224 is rotated or scanned. In an embodiment, the second waveguide 118 and the single support structure 224 are rotated or scanned.

One or more of the various components of the endoscope 100 may be rotated about the optical axis of the lens 210. In an embodiment, when the single support structure 224 is rotated or scanned, then the dispersive element 226, the first reflecting surface 228, and the second reflecting surface 230 are rotated along with the single support structure 224. Rotating a portion of the optical system around the optical axis allows the endoscope 100 to acquire a two dimensional image of the sample. Likewise, scanning a portion of the optical system allows the endoscope 100 to acquire a two dimensional image. This allows an SEE to obtain an image in which one dimension (x, r) is encoded by wavelength, while a second dimension (y,θ) is encoded with time. This optical design allows for a small diameter forward view SEE probe.

Figure 3:
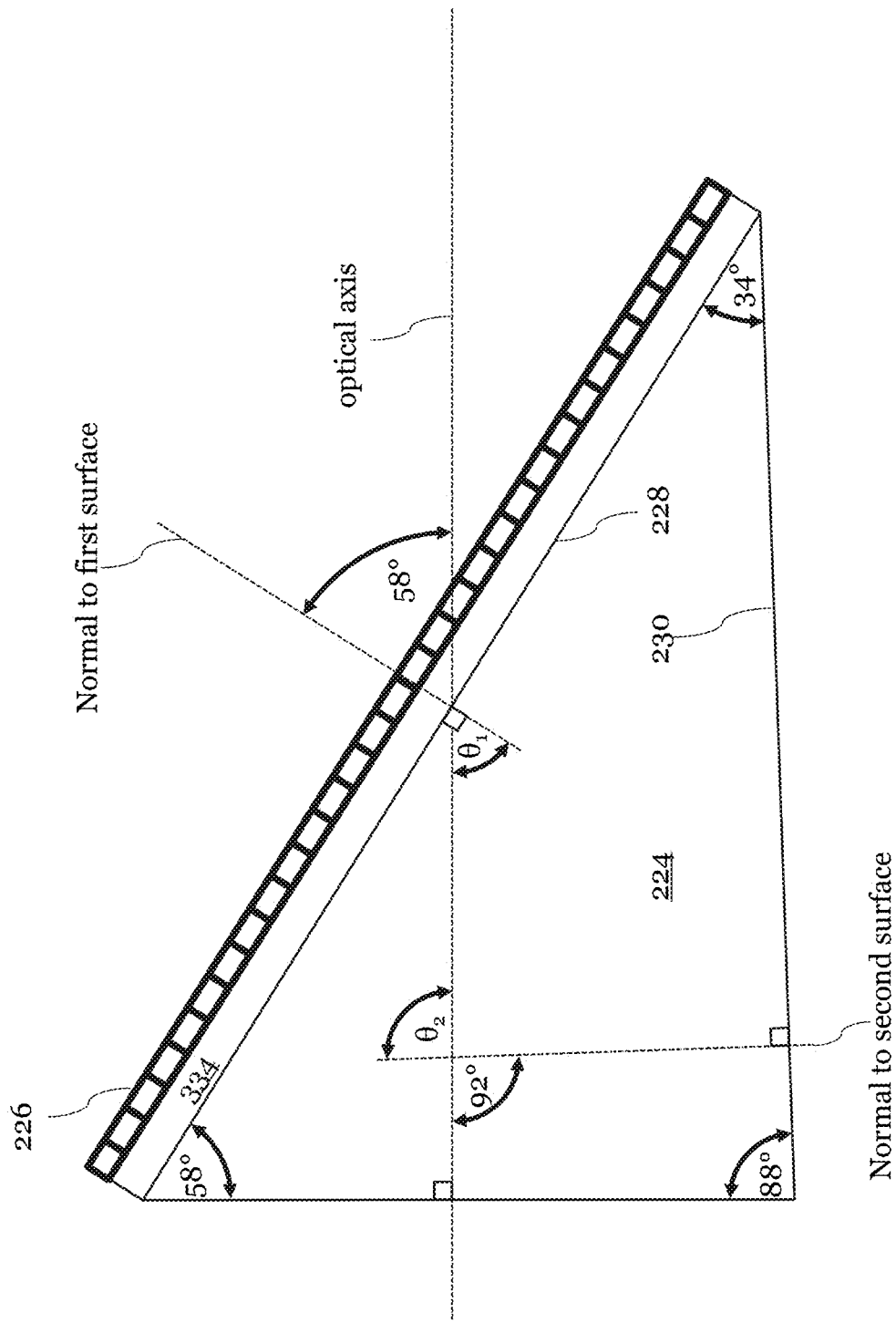
FIG. 3 is an illustration of a portion of an embodiment.

An example of at least the first embodiment of the present disclosure may include a first waveguide 108 that includes a single mode fiber with an NA of 0.1. The first waveguide 108 may also include a coreless fiber made of fused silica with a length of 500 um. The coreless fiber may be coupled to a GRIN lens 210 with a length 3.2 mm. The single support structure 224 may have a refractive index $n_1$ of 1.65 and may be attached to an end of the GRIN lens 210. FIG. 3 is an illustration of a portion of the first example of an embodiment, which includes a thin film or layer 334 on the single support structure 224 and forms the first reflecting surface 228. The thin film or layer 334 may have a refractive index $n_2$ of 1.34. Equation (2) below is an equation for calculating the critical angle $\theta_{critical}$ for TIR which for this example is 54.3°.

$$\theta_{critical} = \sin^{-1}\left(\frac{n_2}{n_1}\right) \quad (2)$$

As illustrated in FIG. 3 an angle $\theta_1$ between a normal of the first reflecting surface 228 of a reflecting component 334 and the optical axis is −58° in an embodiment (in which the angle rotates from the optical axis to the surface normal in the counter-clockwise direction then the sign is negative; otherwise the sign is positive). While the angle $\theta_2$ between a normal of the second reflecting surface 230 and the optical axis of the GRIN lens 210 is 92° in an embodiment. In an embodiment, the single support structure 224 is a 58-34-88 prism which is oriented such that one of the surfaces of the single support structure 224 is perpendicular to optical axis of the GRIN lens 210. In another embodiment, the GRIN lens 210 may be angle polished at 2° relative to the optical axis, and the single support structure 224 may be a 60-30-90 prism that is oriented at a 2° relative to the optical axis such that the angle $\theta_1$ causes the first surface to be a TIR surface for the illumination light. In an embodiment, the single support structure 224 is oriented such that the angle $\theta_2$ causes illumination light that is reflected from the first reflecting surface 228 due to TIR to be reflected back through the second reflecting surface 230. In another embodiment, the angles of the single support structure 224 are designed such that $\theta_2$ causes illumination light that is reflected from the first reflecting surface 228 due to TIR to be reflected back through the second reflecting surface 230.

In another embodiment, the refractive index of the single support structure 224 and the refractive index of the thin film 334 may be adjusted such that the single support structure 224 is a 60-30-90 prism and the angle $\theta_1$ causes the first surface to be a TIR surface for the illumination light. In addition, the single support structure 224 is oriented such that the angle $\theta_2$ causes illumination light that is reflected from the first reflecting surface 228 due to TIR to be reflected back through the second reflecting surface 230. In another embodiment, the angles of the single support structure 224 are designed such that $\theta_2$ causes illumination light that is reflected from the first reflecting surface 228 due to TIR to be reflected back through the second reflecting surface 230.

In an embodiment, the dispersive element 226 is a grating with a groove density of 1379 lines per mm. In an embodiment, the second reflecting surface 230 is a mirror coated surface. A working distance of an embodiment is about 20 mm. In at least one embodiment, the working distance is the distance between the dispersive element 226 and the subject or sample 116 when the spectrally encoded line 114 is focused on the subject or sample 116.

One advantage of this embodiment is that the optical components are located on the optical axis which allows for easier alignment and assembly.

Figure 4:
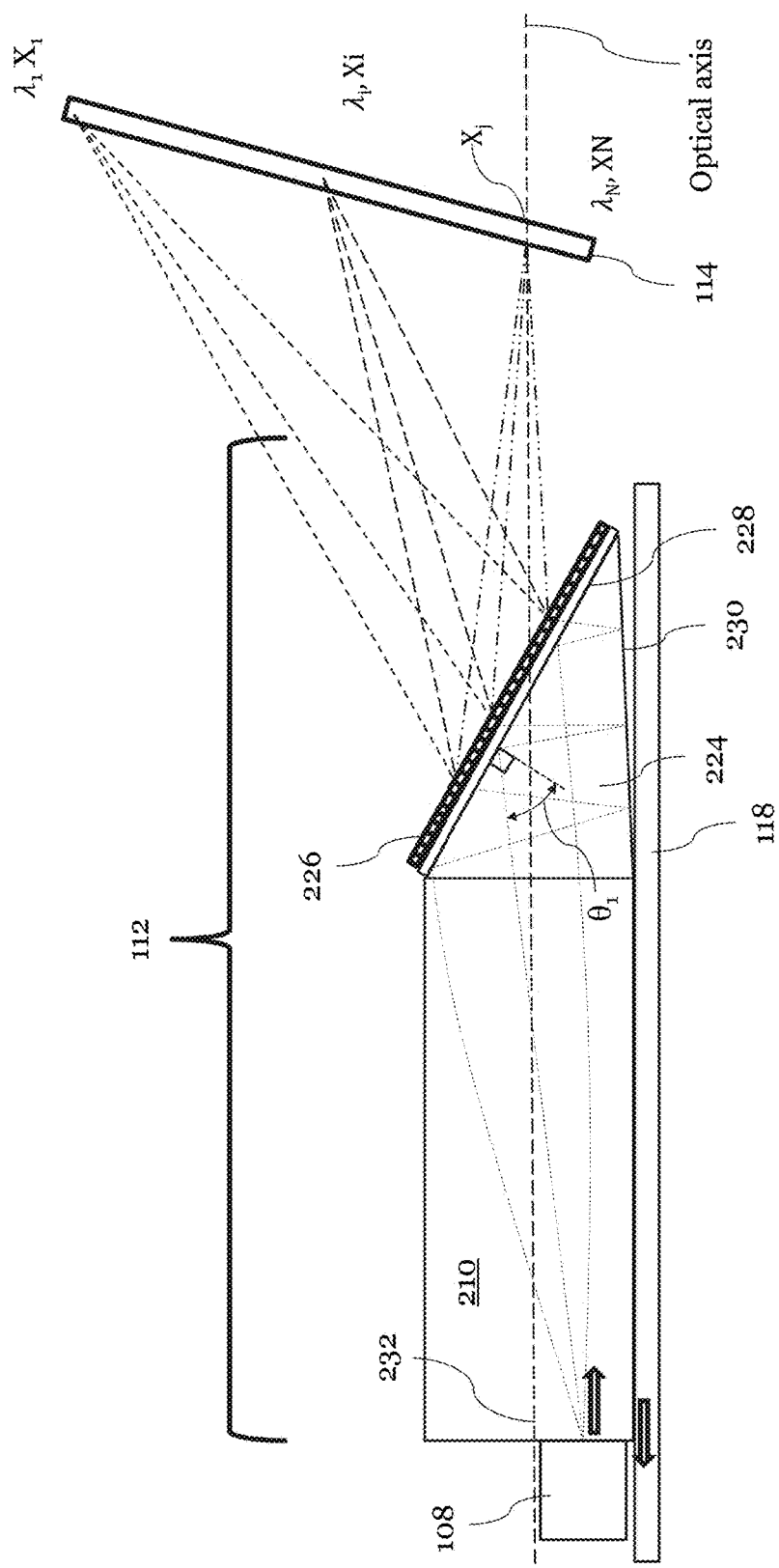
FIG. 4 is an illustration of a portion of at least a second embodiment of the present disclosure.

FIG. 4 is an illustration of a portion of an alternative (second) embodiment which is substantially similar to the first embodiment illustrated in FIG. 2. In the second embodiment, the first waveguide 108 may be attached to or spliced to the lens 210 off-axis relative to the optical axis of the lens 210. As illustrated in FIG. 4 when the first waveguide 108 is positioned away from the optical axis of the lens 210 then the illumination light exits the lens 210 and enters the single support structure 224 at an angle relative to the optical axis of the lens 210. The rest of the components are substantially similar to the first embodiment.

As illustrated in FIG. 4 the off axis position of the first waveguide 108 changes the angle at which a central (chief) ray of light from the waveguide is incident on the first reflecting surface 228. This has an impact on the determination of the angle for total internal reflection which is determined relative to the central ray. The angle for total internal reflection is calculated relative to the angle of incidence $\theta_1$ of the chief ray from the first waveguide 108 relative to a normal of the first reflecting surface 228.

An advantage of the second embodiment is that light is directed to be incident closer to the center of the clear aperture (central area of the optics) of the first reflecting surface 228 and the dispersive element 226. Another advantage of the second embodiment is it allows more freedom in the choice for the angle of the second reflecting surface 230 relative to the central axis of the lens 210. Another advantage of the second embodiment is that shifting the position of the first waveguide 108 also shifts the position of the line of illumination light 114 relative to the optical axis of the lens 210.

Figure 5:
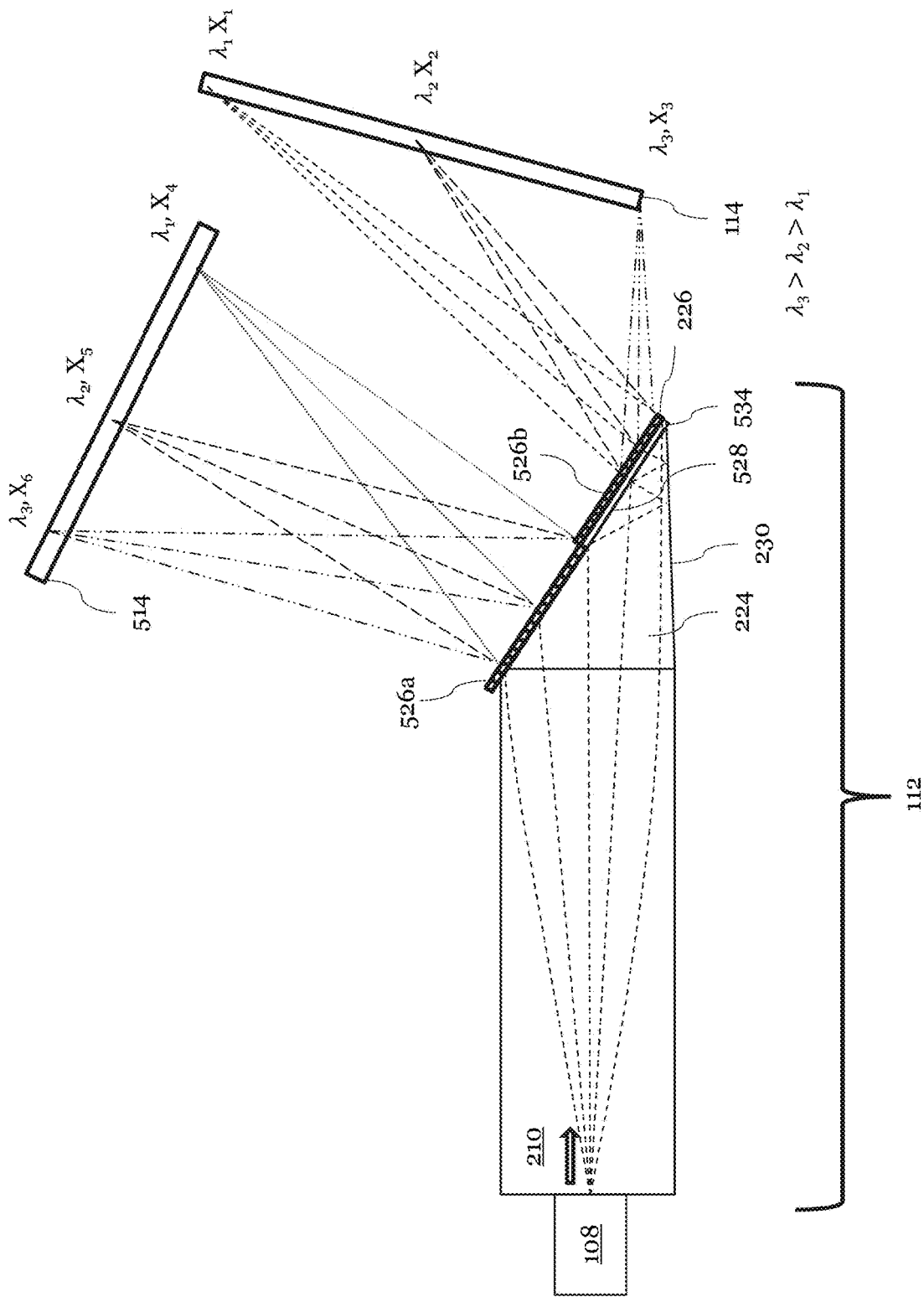
FIG. 5 is an illustration of a portion of at least a third embodiment of the present disclosure.

FIG. 5 is an illustration of a portion of an alternative embodiment which is substantially similar to the first embodiment illustrated in FIG. 2. A third embodiment, may have a dual view or an extended view as illustrated in FIG. 5. In this embodiment, the thin film or layer 534 (a low index material) is only applied to a portion of the (single support structure 224)/(dispersive element 226) interface. This allows a first portion of the illumination light from the first waveguide 108 to be directly diffracted by a first portion 526a of the grating 226 toward a side view direction to form a side view spectral illumination line 514. While a second portion of the illumination light from the first waveguide 108 is reflected by a first reflecting surface 528, then a second reflecting surface 230, passing through the first reflecting surface 528, and then being diffracted toward the forward view direction by a second portion 526b of the grating 226 (see e.g., illumination line 114).

In one embodiment, the thickness (10-500 nm) of the thin film or layer 534 is such that a single grating 226 may act as the first portion 526a of the dispersive element 226 and the second portion 526b of the grating/dispersive element 226 and any distortion due to variation in the thickness has minimal effect on the illumination capability of the optical apparatus and/or system 112 due to the mechanical conformability of the single grating. In an alternative embodiment, the first portion 526a and the second portion 526b are different gratings. An alternative embodiment may further comprise a thin film or layer under the first portion 526a of the dispersive element 226 that has the same thickness as the thin film or layer 534 and has a refractive index that is the same or similar to the refractive index of the single support structure 224. In an alternative embodiment, an area of the single support structure 224 underneath the thin film or layer 534 is shaved down. The area of the single support structure 224 may be shaved down by using etching, polishing, or other well-known methods of removing optical material.

The light diffracted toward the forward view ($\lambda_1,X_1$; $\lambda_2,X_2$; $\lambda_3,X_3$) is the −1 diffraction order of the second portion 526b of the grating 226. The light diffracted toward side view ($\lambda_1,X_4$; $\lambda_2,X_5$; $\lambda_3,X_6$) may be in the +1 diffraction order of the first portion 526a of the grating 226. In an embodiment, the diffraction grating 526b may be designed such that the zeroth order and the +1 orders of most of the wavelengths are not transmitted through the grating 526b. The wavelengths of the +1 orders that are transmitted through the grating 526b may be diffracted at a large angle such that the light is not within the acceptance angle of the detection fiber(s). In an embodiment, the grating 526a may be designed such that the −1 orders of the grating 526a are not transmitted through the grating 526a.

Transmission gratings both diffract and refract light. The diffracted light corresponds to the diffracted orders (+1, −1, etc.). The refracted light corresponds to the zeroth order. If the light incident on the grating has an incident angle that is larger than critical angle then it is possible that zeroth order is not transmitted through the grating but is instead reflected due to TIR. A design parameter of the gratings is their efficiency. Each order (including the zero order) has certain efficiency for each wavelength of light. This efficiency is a function of the illumination angle, wavelength of light, the polarization, etc. This efficiency may be controlled by adjusting the profile, incident angle, and material properties of the grating. For example, the profile may be adjusted to produce a blazed grating. The profile may also be adjusted by controlling the groove density, aspect ratio. One of the material properties that may be adjusted is the refractive index of the grating.

In an embodiment, the efficiency of both gratings 526a and 526b associated with zero order and other orders which are not used, in the embodiment illustrated in FIG. 5 should be less than 50%, or may be less than 40%, 30%, 20%, 10%, 5%, 1%, or 0.1%. Limiting the acceptance angle of the one or more detection fibers can reduce the amount of light associated with the zero order light. In an alternative embodiment, the wavelength ranges of the detected light may be limited to those ranges which are not spatially coincident with the zeroth order beams of light as they exit the gratings 526a and 526b.

Figure 6:
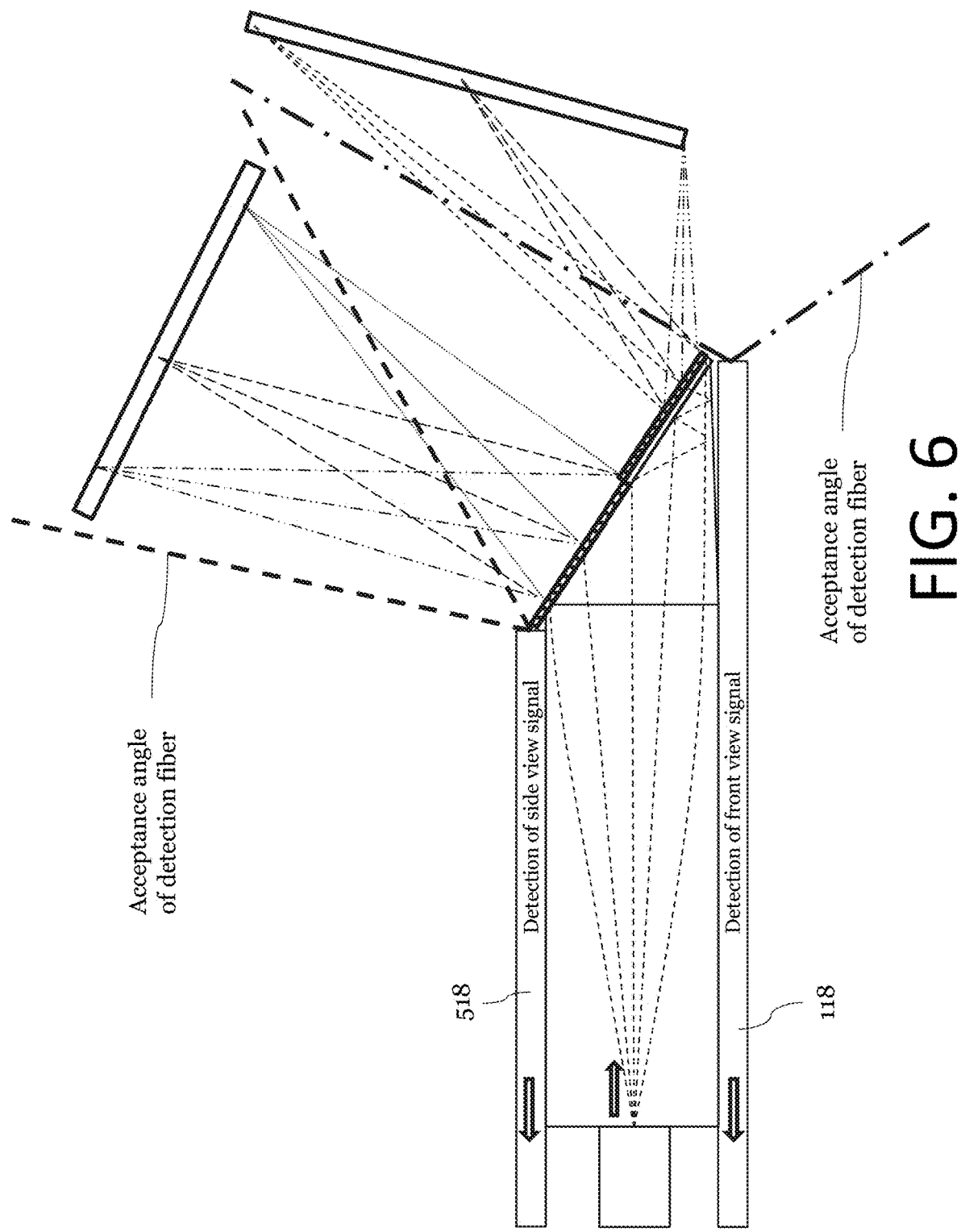
FIG. 6 is an illustration of a portion of an embodiment.

FIG. 6 is an illustration of how a first detection waveguide 118 and a second detection waveguide 518 may be configured in an embodiment. The side/forward view signals may be detected separately using at least two detection waveguides (118 and 518) and two spectrometers. In another embodiment, the side/forward view signals may be detected separately using at least two detection waveguides (118 and 518) with the same spectrometer 120. The spectrometer 120 may include a switch and/or a shutter so that light from only one of the detection waveguides (118 and 518) is detected by the spectrometer 120 at a time. In another embodiment, the spectrometer 120 may be a multiple input spectrometer in which some optical components are shared. For example, the spectrometer 120 may be designed to parallel process input from multiple fibers by for example using a shared CCD array instead of a linear array as the detection system. In one embodiment, different optical fibers from among the multiple fibers may be focused onto to different parts of a dispersive element such as a grating or a prism. The dispersed light may then be detected by a CCD array. For example, one of set of rows of the CCD array may be used for one fiber, while a second set of rows of the CCD array may be used for another fiber.

The side detection waveguide 518 may be angle polished at the input tip and covered by the second portion 526a of the grating 226 to collect the signal from side view while not collecting light from the front view. The front detection waveguide 118 may have a large Numerical Aperture (NA) (for example, NA=0.66) to collect the signal from the forward view. In an embodiment, front detection waveguide 118 is not angle polished, and there is no grating in the front of the waveguide. The input for the front detection waveguide 118 may be positioned relative to the first portion 526a of the grating 226 such that it does not receive light that has been dispersed by the first portion 526a of the grating 226.

One advantage of these embodiments is that substantially similar optical designs may be either a forward view probe (FIG. 4), a dual view probe (FIG. 6), or a side view probe depending on the grating selection and the coverage of the low refractive index thin film or layer. A side view probe may be substantially similar to the forward view probe except it does not include the thin film or layer 334. Another advantage of one or more embodiments of the present disclosure is that the field of view may be easily extended.

An example of a third embodiment of the present disclosure may include a first waveguide 108 that includes a single mode fiber with an NA of 0.1. The first waveguide 108 may also include a coreless fiber made of fused silica with a length of 500 um. The coreless fiber may be coupled to a GRIN lens 210 with a length of 3.3 mm. The single support structure 224 may have a refractive index $n_1$ of 1.65 and may be attached to an end of the GRIN lens 210. A thin film or layer 534 may be included on a portion of the single support structure 224 which forms the first reflecting surface 528. The thin film may have a refractive index $n_2$ of 1.34. Equation (2) above is an equation for calculating the critical angle $\theta_{critical}$ for TIR as 54.3°.

As illustrated in FIG. 5 an angle between a normal of the first reflecting surface 528 of a reflecting component 534 and the optical axis may be −60°. While the angle between a normal of the second reflecting surface 230 and optical axis may be 92° in an embodiment. In an embodiment, the single support structure 224 may be a 60-32-88 prism which is oriented such that one of the surfaces of the single support structure 224 is perpendicular to the optical axis. In another embodiment, the single support structure 224 is a 60-30-90 prism that is oriented at a 2° relative to the optical axis such that: $\theta_1$ is a TIR surface. The angle of the reflecting component relative to the optical axis may be adjusted depending on the grating design and the diffraction efficiency of the grating at different incident angles.

In an embodiment, the dispersive element 226 is a grating with a groove density of 1550 lines per mm. In an embodiment, the second reflecting surface 230 is a mirror coated surface. A working distance of an embodiment is about 20 mm. In at least one embodiment, the working distance is the distance between the dispersive element 226 and the subject or sample 116 when the spectrally encoded line 114 is focused on the subject or sample 116.

In another (fourth) embodiment, polarization may be used to distinguish the detected signals from side view/forward view. The polarized signals may be independently detected by the spectrometer 120 using one or more of a polarizer, an optical switch, a beam splitter, and/or a polarization beam splitter that allows separation of the signals in one of either space or time. The polarized signals may be detected by two spectrometers, and each of which only accepts one polarization. In this case, the signals from different views may be detected simultaneously.

In one embodiment, the front view waveguide 118 may include a polarizer such that only detection light with the first polarization is received by the front view waveguide 118, while the side view detection waveguide 518 may include a polarizer such that only detection light with the second polarization is received by the side view waveguide 518.

Figure 7:
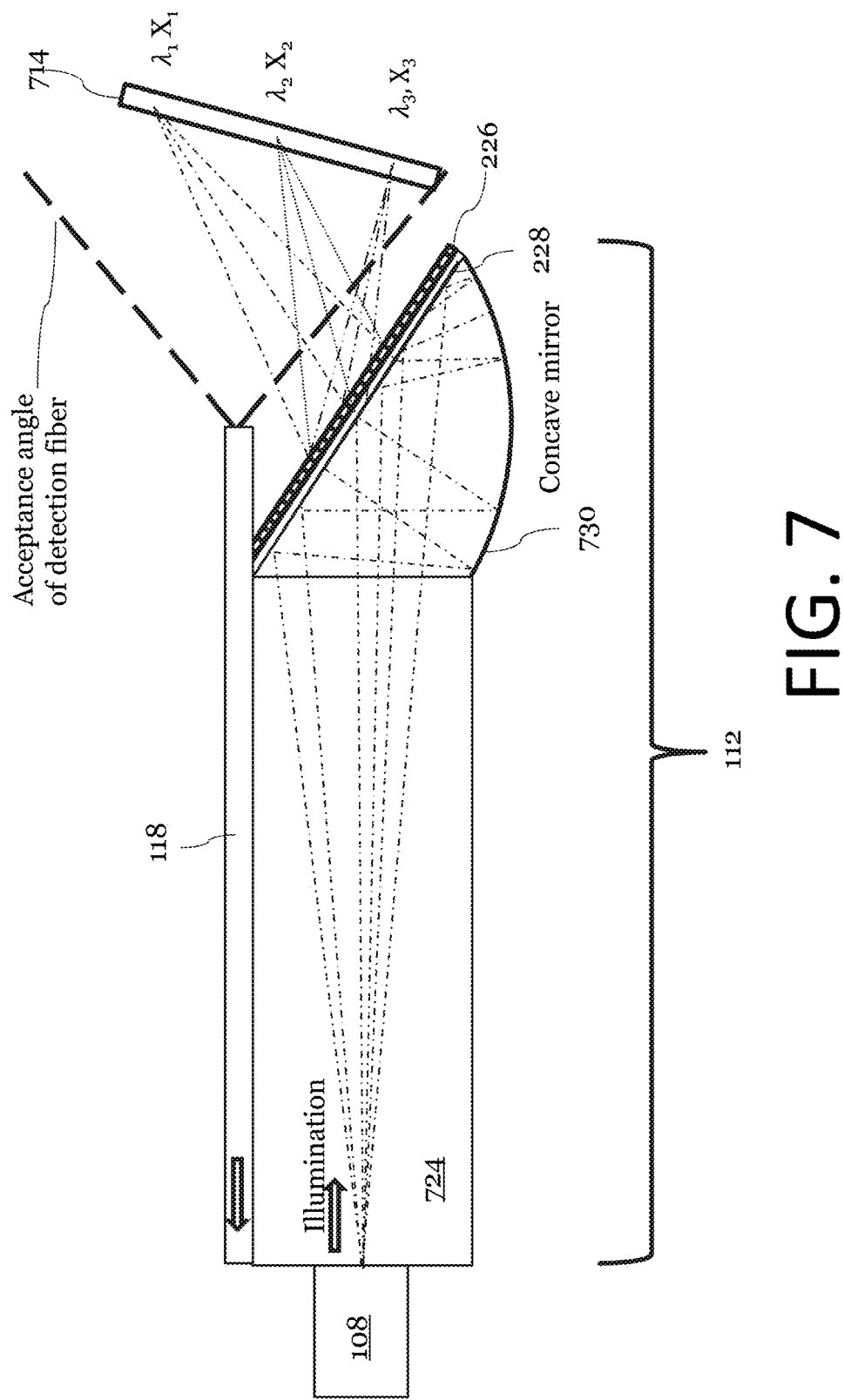
FIG. 7 is an illustration of a portion of at least a fifth embodiment of the present disclosure.

FIG. 7 is an illustration of a portion of at least a fifth embodiment of the present disclosure that is substantially similar to the first embodiment illustrated in FIG. 2. In this fifth embodiment, the second surface is a curved reflecting surface 730 instead of a tilted reflecting surface 230. In the fifth embodiment, instead of using a GRIN lens 210 as the focusing optics, a concave mirror 730 may be used instead. In an alternative embodiment, the concave mirror 730 may be used in addition to a GRIN lens 210. Light from the first waveguide 108 may propagate through a single support structure 724 that includes a column of glass which guides light from an output port of the first waveguide 108 to a first reflecting surface 228. As light passes through the single support structure 724 it may be divergent and incident on the first reflecting surface at a first set of angles relative to a normal of the first reflecting surface 228. The first set of angles may be greater than $\theta_{critical}$. The illumination light may then be reflected off the curved surface 730 which acts as a concave mirror. The illumination light from the concave mirror 730 may then pass through the dispersive element 226. A detection waveguide 118 may be placed next to the single support structure 724 and may have a large NA.

The concave mirror 730 may be made by forming a ball lens with a fusion splicer and then applying a mirror coating to the ball surface. The radius of the curved reflecting surface 730 may be such that the light incident on the grating is substantially collimated, thus compensating for the divergence of the light as it exits the first waveguide 108 while still focusing the light onto the spectral line 714.

Figure 8:
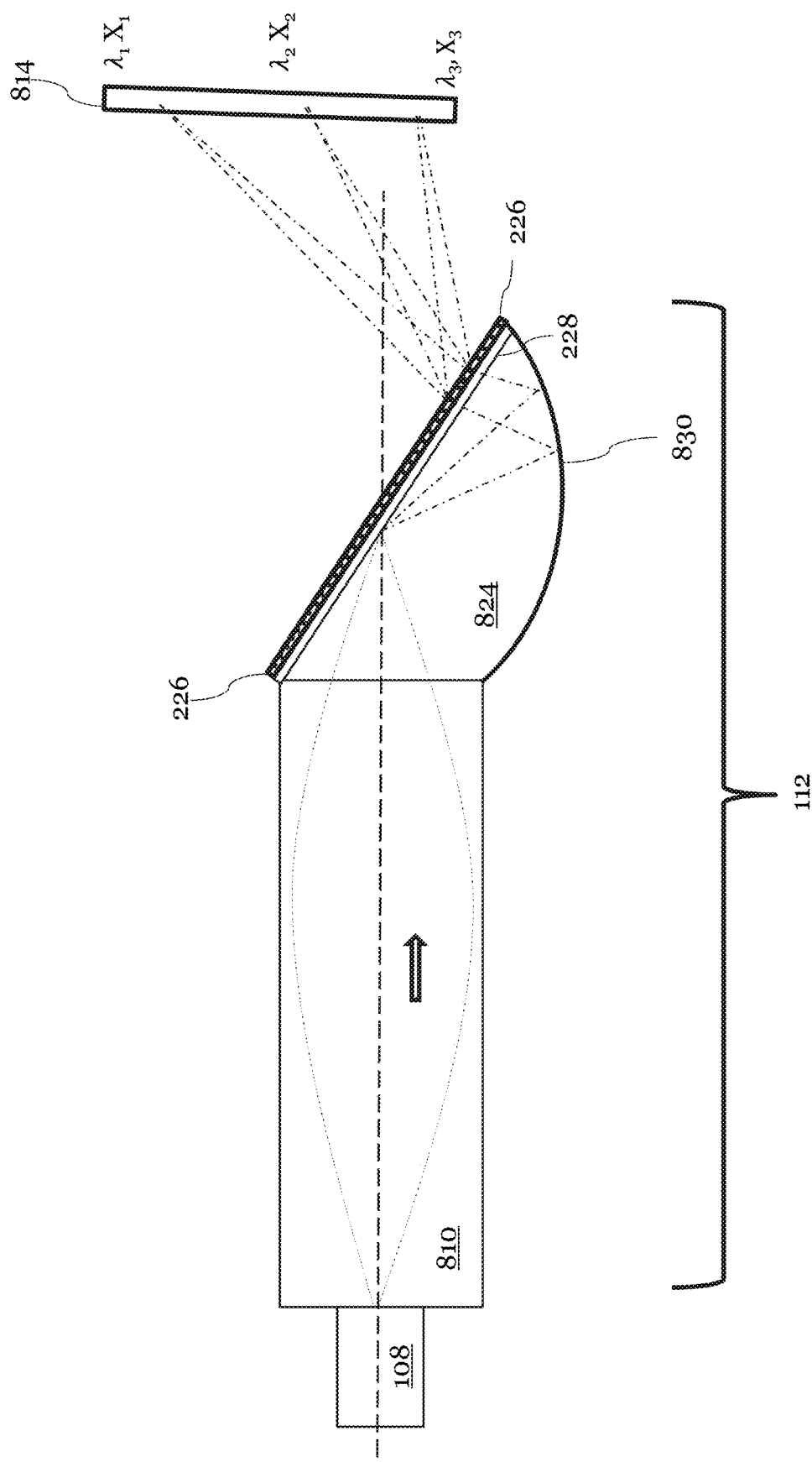
FIG. 8 is an illustration of a portion of at least a sixth embodiment of the present disclosure.

FIG. 8 is an illustration of a portion of an alternative (sixth) embodiment which is substantially similar to the first embodiment illustrated in FIG. 7. This sixth embodiment may be designed to have a longer working distance. The concave mirror 830 may be elliptical, having two foci. Light from the first waveguide 108 may propagate through a GRIN lens 810 having an intermediate focus close to a first focus of the elliptical reflecting surface 830 which may also be close to or intersecting with the first reflecting surface 228. The first waveguide 108 may also include a coreless fiber made of fused silica with a length of 500 um. The GRIN lens 810 may have a pitch of around 0.42 such that the illumination light is focused through the single support structure 824 and onto the first reflecting surface 228.

After the illumination light is reflected off the first reflecting surface 228 due to total internal reflection, the illumination light is directed toward a second reflecting surface 830. The second reflecting surface 830 is an elliptical mirror. The illumination light is reflected off the second reflecting surface 830 and may pass through first reflecting surface 228 to be dispersed by the dispersive element 226.

The dispersive element 226 may diffract the light along a spectral line 814 that coincides with second foci of the elliptical mirror of the second reflecting surface 830.

The GRIN lens 810 focuses the illumination light onto the first reflecting surface 228. The illumination light thus is incident onto the first reflecting surface 228 on a range of angles that are a function of the NA of the GRIN lens 810. The first reflecting surface 228 is oriented such that the smallest incidence angle of the illumination light is greater than the $\theta_{critical}$, so that the total internal reflection occurs at some or all wavelengths for the cone of the illumination light from the GRIN lens 810. In an alternative embodiment, the first waveguide 108 may be shifted away from the optical axis of the GRIN lens 810 so as to adjust the incident angle of the illumination light onto the first reflecting surface 228.

An example of the sixth embodiment may include a first waveguide 108 that includes a single mode fiber with an NA of 0.1. The first waveguide 108 may also include a coreless fiber made of fused silica with a length 500 um. The coreless fiber may be coupled to a GRIN lens 810 with a length 6.3 mm.

The GRIN lens 810 may be coupled to a single support structure 824 with a refractive index of 1.65. A portion of the single support structure 824 may take the shape of an elliptical ball. The single support structure 824 may be angle polished to create an interface for the first reflecting surface 228. A normal of a polished surface of the single support structure may form an angle $\theta_1$=−58° with the optical axis of the GRIN lens 810 or with a chief ray of the illumination light from the waveguide 108 if the chief ray is not aligned with the optical axis. The polished surface of the single support structure may also intersect with one of the foci of the elliptical ball of the single support structure 824. A thin film or layer 334 with a refractive index of 1.34 may be applied to the polished surface of the single support structure 824 thus forming the interface for the first reflecting surface 228. In an embodiment, the critical angle $\theta_{critical}$ for TIR is 54.3°. In an embodiment, a groove density of the grating 226 may be 1379 lines per mm.

A mirror coating may be applied to the elliptical ball portion of the single support structure 824, thus providing a second reflecting surface 830 that reflects light from the first reflecting surface 228 and through the grating 226. The grating 226 diffracts the illumination light toward the forward view ($\lambda_1,X_1; \lambda_2,X_2; \lambda_3,X_3$) in accordance with the −1 diffraction order of the grating 226.

In an example of the sixth embodiment, the elliptical ball portion of the single support structure 824 may have a curvature of 0.3 mm and a conic constant −0.4.

Figure 9:
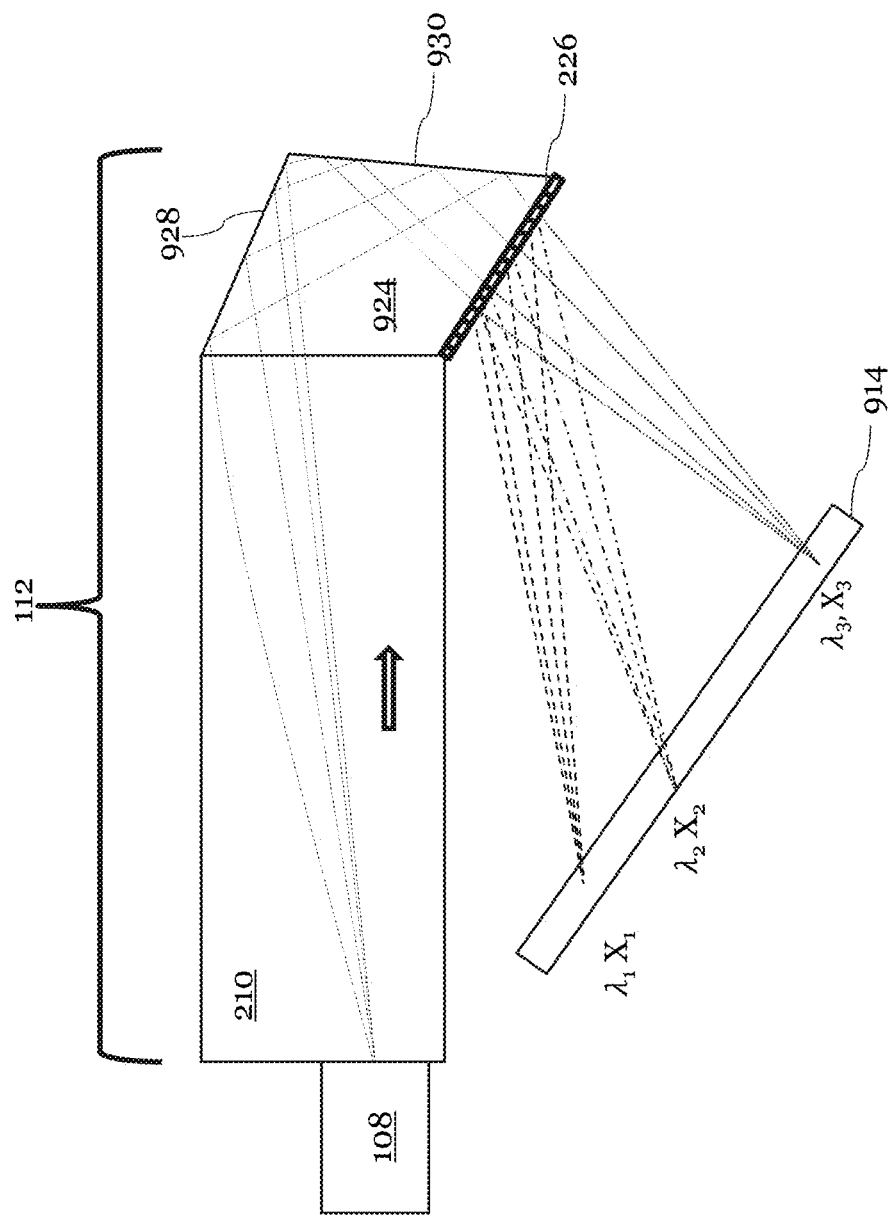
FIG. 9 is an illustration of a portion of at least a seventh embodiment of the present disclosure.

FIG. 9 is an illustration of a portion of an alternative (seventh) embodiment which is substantially similar to the second embodiment illustrated in FIG. 4, except that it is a backwards view design as opposed to a forward view design. In this seventh embodiment, the first waveguide 108 may be attached or spliced off-axis relative to the optical axis of the lens 210.

Illumination light from an off-axis first waveguide 108 propagates through a GRIN lens 210. The illumination light after propagating through the GRIN lens 210 enters a single support structure 924. The single support structure may include three surfaces, a first reflecting surface 928, a second reflecting surface 930, and a third surface on which a dispersive element 226 is attached.

The first reflecting surface 928 may reflect illumination light that has propagated through the GRIN lens 210 and the support structure 924. The first reflecting surface 928 may reflect the illumination light due to TIR or due to a reflective film or layer on the first reflecting surface 928. The second reflecting surface 930 may reflect illumination light from the first reflecting surface 928. The second reflecting surface 930 may reflect the illumination light due to TIR or due to a reflective film or layer on the second reflecting surface 93o. The second reflecting surface 930 may reflect the illumination light from the first reflecting surface 928 such that it propagates through the dispersive element 226.

The dispersive element 226 may be a transmission type diffractive grating that disperses light along a −1 diffractive order onto a spectral line 914. A backward view endoscope may be useful depending on the complexity of the surface of a subject being imaged such as in colonoscopy in which a surface being imaged may have many folds.

Figure 10A:
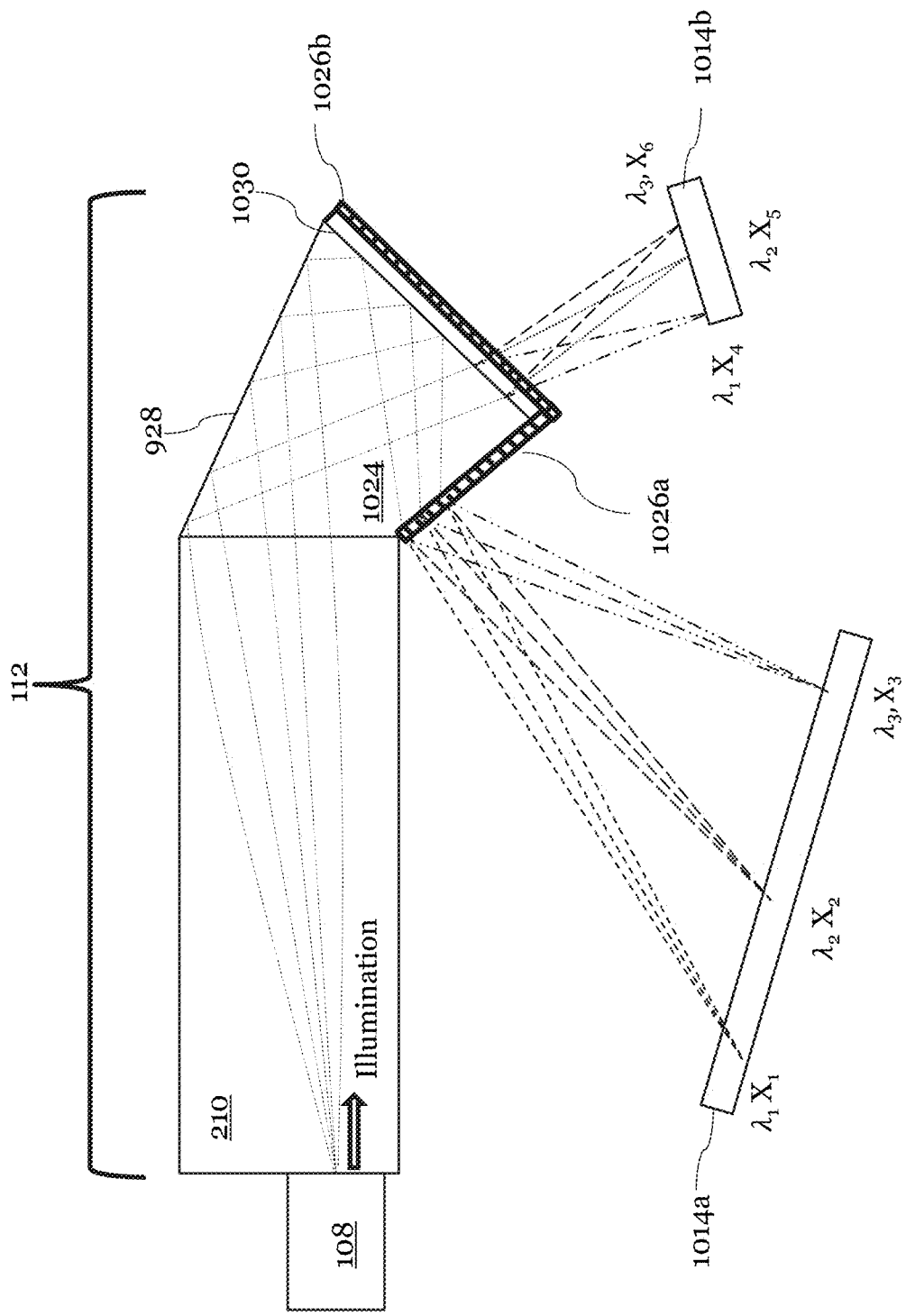
FIGS. 10A-B are illustrations of a portion of at least an eighth embodiment of the present disclosure.
Figure 10B:
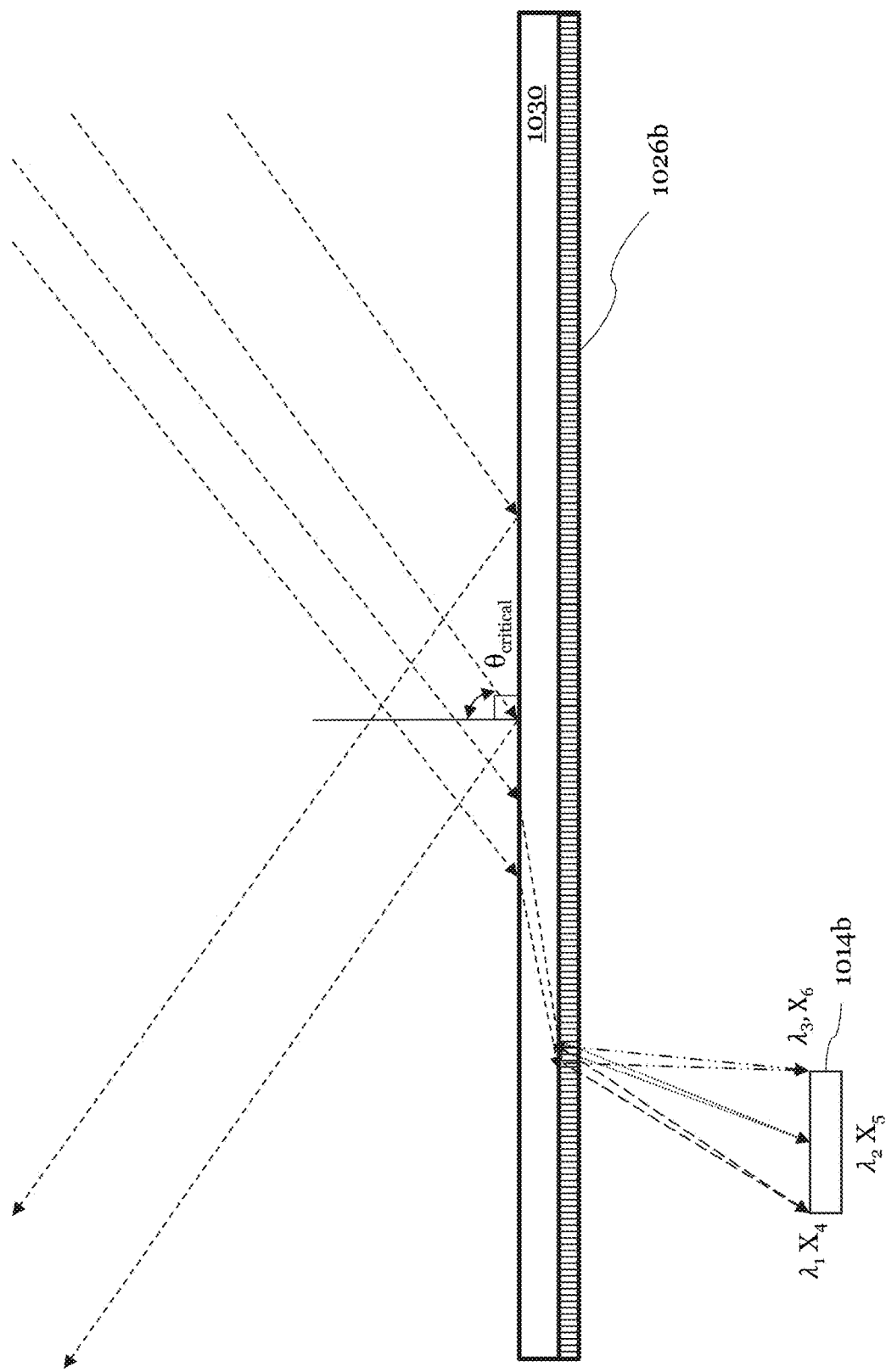

FIGS. 10A-B are illustrations of a portion of an alternative (eighth) embodiment which is substantially similar to a combination of the seventh embodiment and the third embodiment illustrated in FIGS. 9 and 5, respectively, except that it includes a backwards view and a side view. The eighth embodiment may include two gratings 1026a and 1026b. In an embodiment, light from a first waveguide 108 propagates through a GRIN lens 210. The first waveguide may be positioned off-axis from a central axis of the GRIN lens 210. The illumination light after propagating through the GRIN lens 210 enters a single support structure 1024. The illumination light may then be reflected off a first reflecting surface 928. In one embodiment, the reflection off the first reflecting surface 928 is due to TIR; in another embodiment, the reflection off the first reflecting surface is due to a mirror coating on the first reflecting surface 928.

In the back view propagation mode, illumination light that reflects off the first reflecting surface 928 may be reflected off a second reflecting surface 1030 and propagates through the first dispersive device 1026a which may be a grating to form an illumination line 1014a. Light that is reflected by the second reflecting surface 1030 may be reflected due to TIR. The second reflecting surface 1030 may be formed from a thin film or layer on the single structure 1024.

In the side view propagation mode, illumination light that reflects off the first reflecting surface 928 propagates through the second dispersive device 1026b which may be a grating. In the side view propagation mode, total internal reflection does not happen on surface 1030 because the incident angles of the illumination light relative to the second reflecting surface 1030 are smaller than a critical angle. As illustrated in FIG. 10B, light which is incident on the second reflecting surface 1030 at an angle that is greater than the critical angle is reflected off the second reflecting surface 1030 and towards the first dispersive device 1026a. While light that is incident on the second reflecting surface 1030 at an angle that is less than the critical angle passes through the second reflecting surface 1030 and is incident on the second dispersive device 1026b which is then diffracted to form a second illumination line 1014b.

The side/backward view signals may be detected separately using at least two detection waveguides and two spectrometers. In another embodiment, the side/backward view signals may be detected separately using at least two detection waveguides with the same spectrometer 120. The spectrometer 120 may include a switch and/or a shutter so that light from only one of the detection waveguides is detected by the spectrometer 120. In another embodiment, the spectrometer 120 may be a multiple input spectrometer in which some optical components are shared. For example, the spectrometer 120 may be designed to parallel process input from multiple fibers by for example using a shared CCD array instead of a linear array as the detection system.

Detection waveguides may be located next to illumination optics. The detection waveguides may be such that not all of the signal(s) to the fibers is/are blocked by the illumination optics. To detect the signals from back view, there may be reflective, diffractive, and/or scattering optics in front of detection fibers such that the back-view signal is directed within the acceptance NA of the detection waveguide associated with the back view.

To detect the signals from a side view, at least one of the detection waveguides may be angle-polished at the input and covered by a grating to collect the signal from the side view while not detecting light from the back view. The reflective optics and the NA of the detection fibers may be designed such that the cross-talk between the signals from the two different views may be reduced and eliminated.

Figure 11:
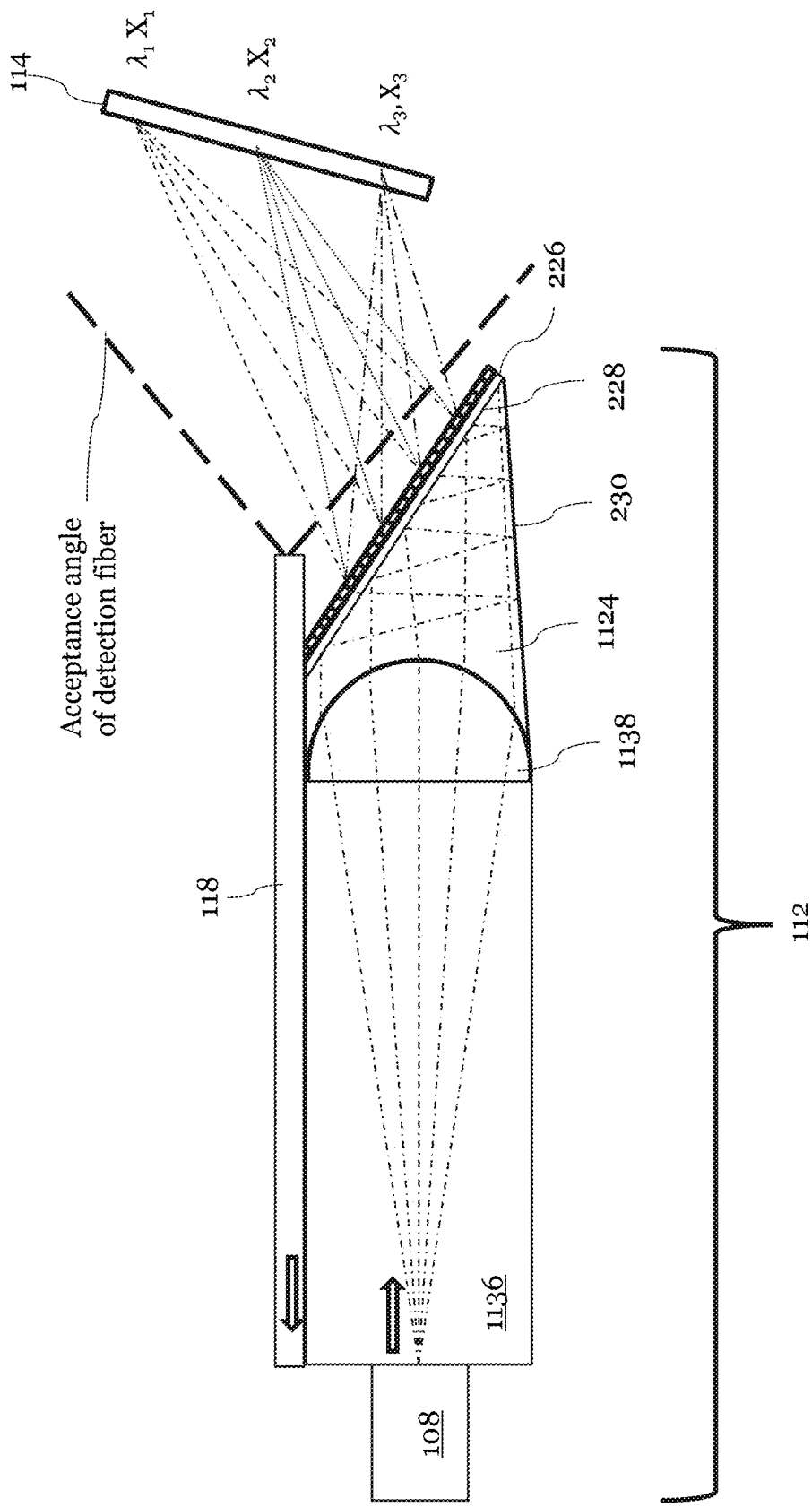
FIG. 11 is an illustration of a portion of at least a ninth embodiment of the present disclosure.

FIG. 11 is an illustration of a portion of an alternative (ninth) embodiment which is substantially similar to the second embodiment illustrated in FIG. 4, except that instead of using a GRIN lens as the focusing optical element a ball or a half ball lens may be used.

Illumination light from the first waveguide 108 may propagate through a spacer 1136. The refractive index of the spacer may substantially match the refractive index of a core of the first waveguide 108. After passing through the space 1136 the illumination light may be focused by a half ball lens 1138 that is attached to an end of the spacer 1136. After passing through the half ball lens 1138 the illumination light is collimated and slightly focused as it enters a single support structure 1124.

The illumination light after passing though the ball lens is reflected off the first reflecting surface 228 of the single support structure 1124. The single support structure 1124 may be made of UV cure resin or epoxy. The illumination light reflects off the first reflecting surface due to TIR. The illumination light then passes back through the single support structure 1124 and is then reflected again off of the second reflecting surface 230 of the single support structure 1124. The second reflecting surface 230 may be a polished flat surface and may have a mirror coating. In an alternative embodiment, the second reflecting surface 230 may not have a mirror coating and may reflect the illumination light due to TIR. After being reflected by the second reflecting surface 230, the illumination light passes back through the single support structure 1124, and this time passes through the first reflecting surface 228 and is dispersed by the dispersive element 226 which may be a grating.

In an embodiment the ball lens 1138 may be formed using a fusion splicer from the spacer 1136. In an embodiment, a detection waveguide 118 could be placed next to the spacer 1136 and may have large NA.

Figure 12:
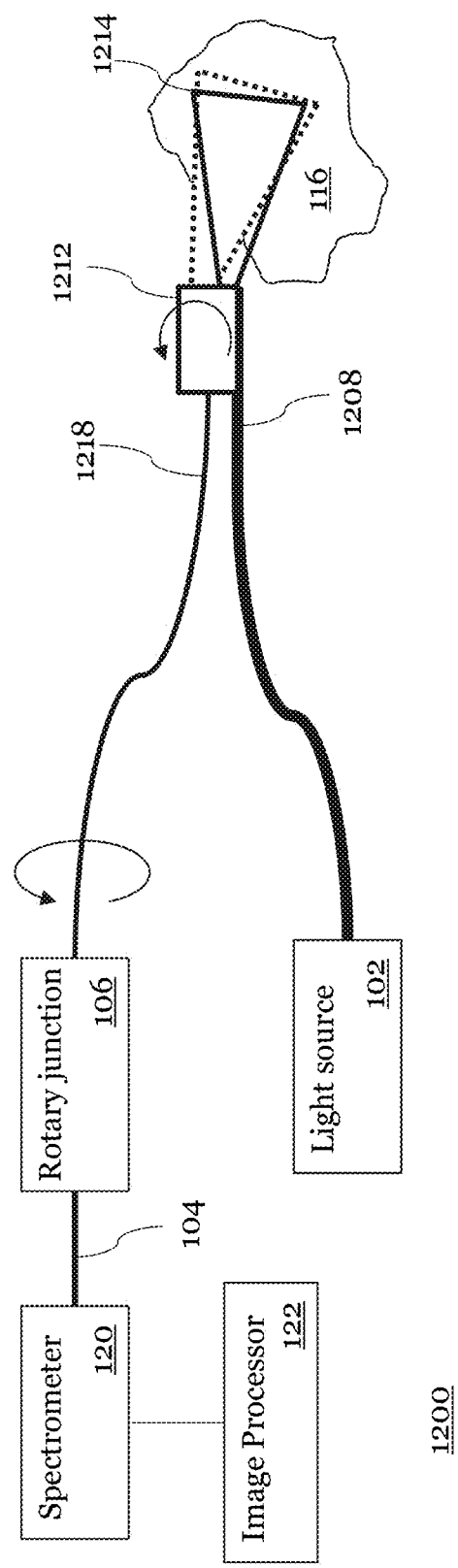
FIG. 12 is an illustration of at least a tenth embodiment of the present disclosure.

FIG. 12 is an illustration of a tenth embodiment 1200 which is substantially similar to the first embodiment illustrated in FIG. 1. The tenth embodiment 1200 may include or be connected to the broadband light source 102. The broadband light source 102 may be connected to a first waveguide 1208 that is substantially similar to the second waveguide 118. In the tenth embodiment, the first waveguide 1208 may be a multimode fiber. The first waveguide 1208 may have a core with a diameter of 100 µm, 200 µm, or 400 µm. The first waveguide 1208 may be used to illuminate the sample 116 with illumination light 1214.

An optical apparatus and/or system 1212 may be used to gather and spectrally encode light which is incident on the sample 116. The optical system 1212 (spectrally encoded channel) may be used as an imaging channel while the first waveguide 1208 may be used as a separate illumination channel for illuminating the sample 116 with broadband light. The broadband light may be incoherent. The optical system 1212 may be coupled to a detection waveguide 1218. The detection waveguide 1218 may be connected to a rotary junction 106. The rotary junction 106 may be connected to a fiber 104. The rotary junction 1o6 may allow the detection waveguide 1218 and the optical apparatus and/or system 1212 to rotate while the fiber 104 remains stationary. The fiber 104 may be connected to a spectrometer 120 as described above. The spectrometer 120 may be connected to an image processor 122 as described above (and/or to a computer 1300, 1300' as aforementioned or as further discussed below).

Figure 13:
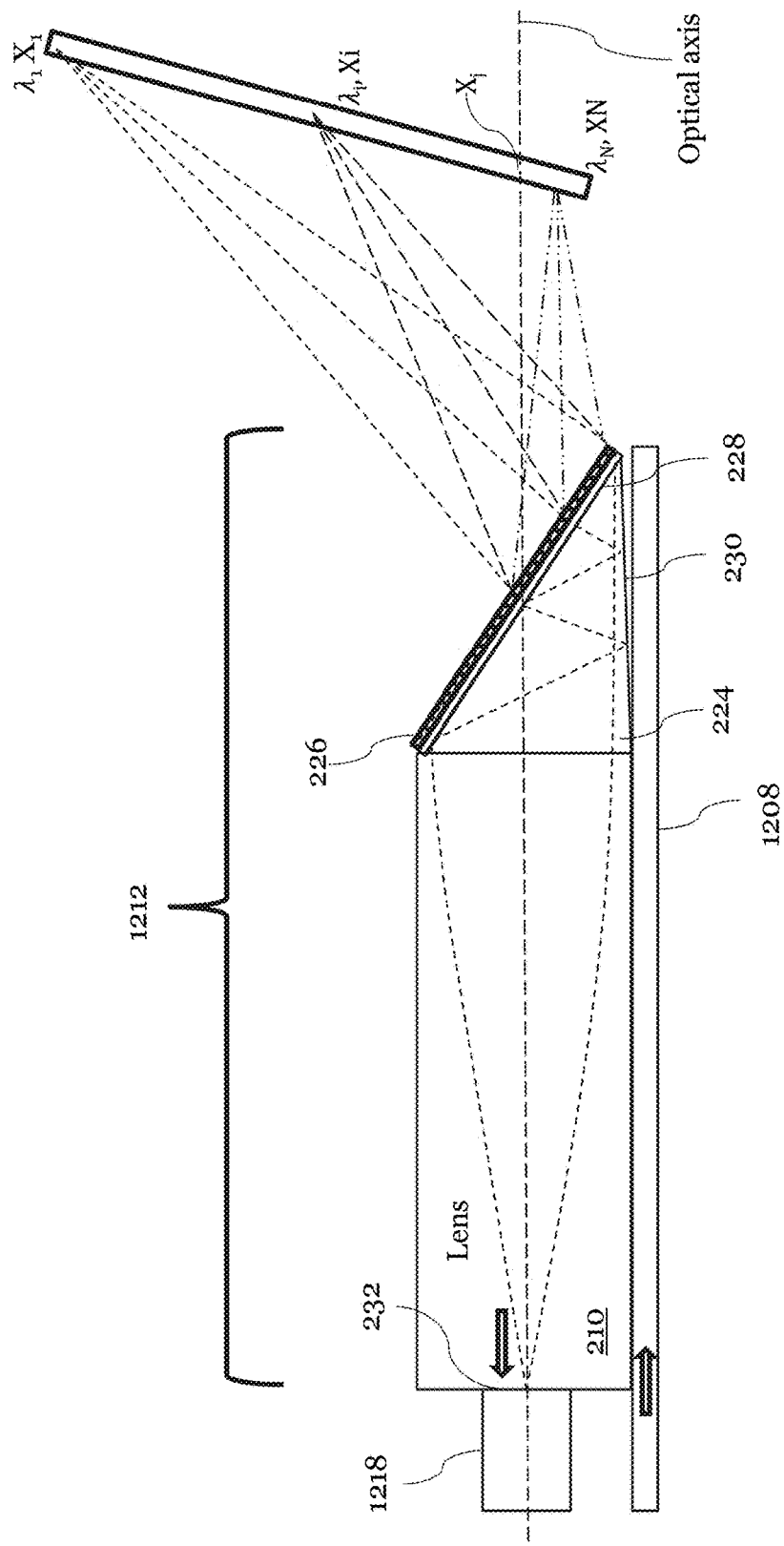
FIG. 13 is an illustration of a portion of an embodiment.

FIG. 13 is an illustration of the optical apparatus and/or system 1212 which is substantially similar to the optical apparatus and/or system 112. As described previously, the first waveguide 1208 illuminates the sample 116. The optical apparatus and/or system 1212 gathers light. The gathered light enters the optical apparatus and/or system 1212 via a dispersive element 226. The dispersive element 226 diffracts the light which passes through the first reflecting surface 228, passes through the single support structure 224, is reflected off the second reflecting surface 230, and is reflected off the first reflecting surface 228 via TIR towards the lens 210 which focuses the gathered light onto the detection waveguide 1218.

The detection waveguide 1218 acts as aperture and only accepts in a specific range of angles. The diffraction grating ensures that only light with specific wavelengths entering the optical system 1212 at specific angles will be accepted by the detection waveguide 1218 after passing through the optical system 1212, which causes specific locations ($X_1$, $X_i$, . . . , $X_N$) to be encoded with specific wavelengths ($\lambda_1$, $\lambda_i$, . . . , $\lambda_N$). Thus, a spectrally encoded signal which can be decoded by the spectrometer 120 is provided.

Figure 14:
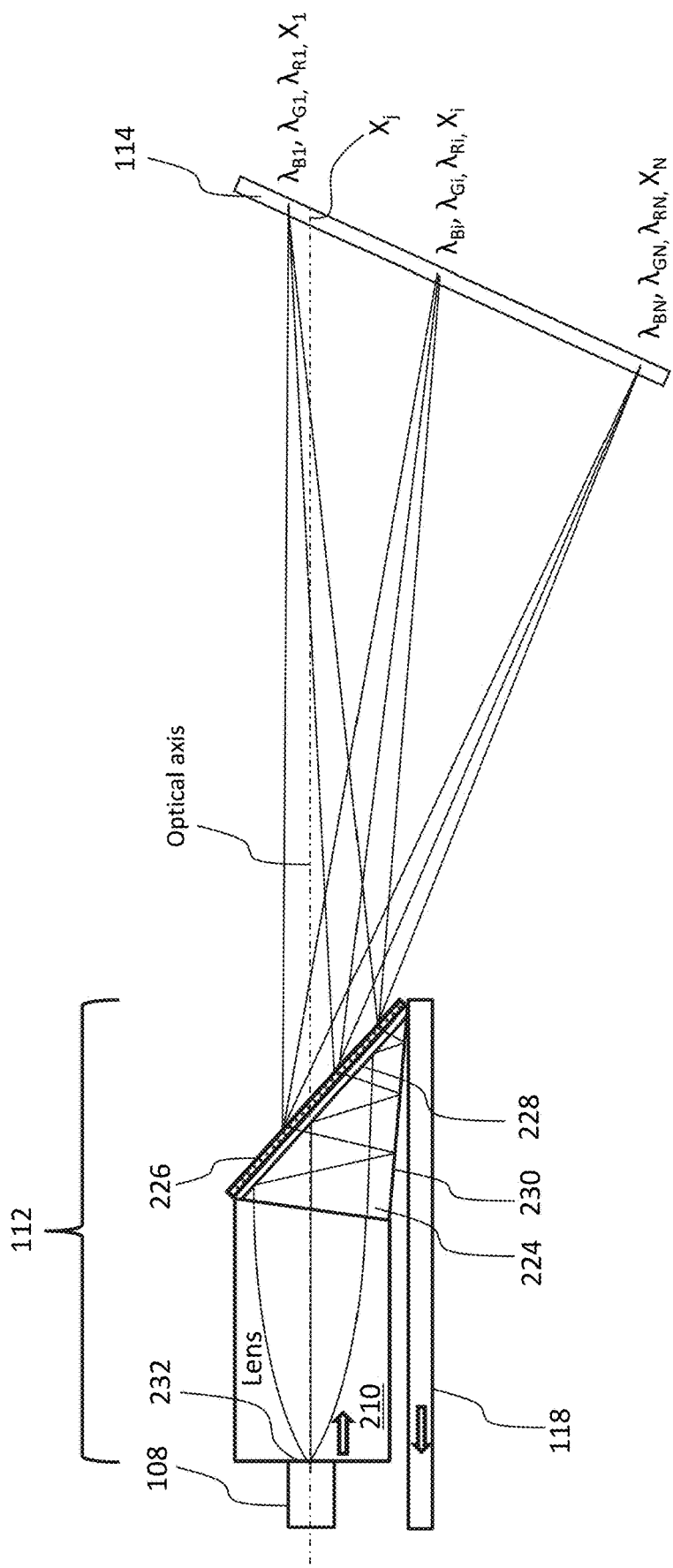
FIG. 14 is a schematic view for describing at least an eleventh embodiment.

The details of at least an eleventh embodiment of the present disclosure, including an optical system 112 having the lens 210, the support structure 224, and the dispersive element 226 are shown in FIG. 14 and Table 1. In the embodiment, as the support structure, an example of a design using a glass material having a high refractive index is given.

TABLE 1

| | Refractive Index (nd) | Remarks |
|---|---|---|
| $n_0$ | 1.48 | GRIN lens |
| $n_1$ | 2.0509 | TAFD65, HOYA |
| $n_2$ | 1.5037 | UV cure resin |

| | Reflection/Refraction Angle | Remarks |
|---|---|---|
| $\theta_1$ | 8.0° | |
| $\theta_2$ | 5.77° | |
| $\theta_3$ | 49.51° | critical angle $\theta_{critical}$ = 47.18° |
| $\theta_4$ | 11.99° | |
| $\theta_5$ | 25.54° | |
| $\theta_6$ | 36.0° | |
| $\theta_7$ | 47.28° | |

| Glass Vertex Angles, Etc. | |
|---|---|
| α | 37.53° |
| β | 87.19° |
| γ | 5.20° |

Grating: 650 line/mm

Figure 15:
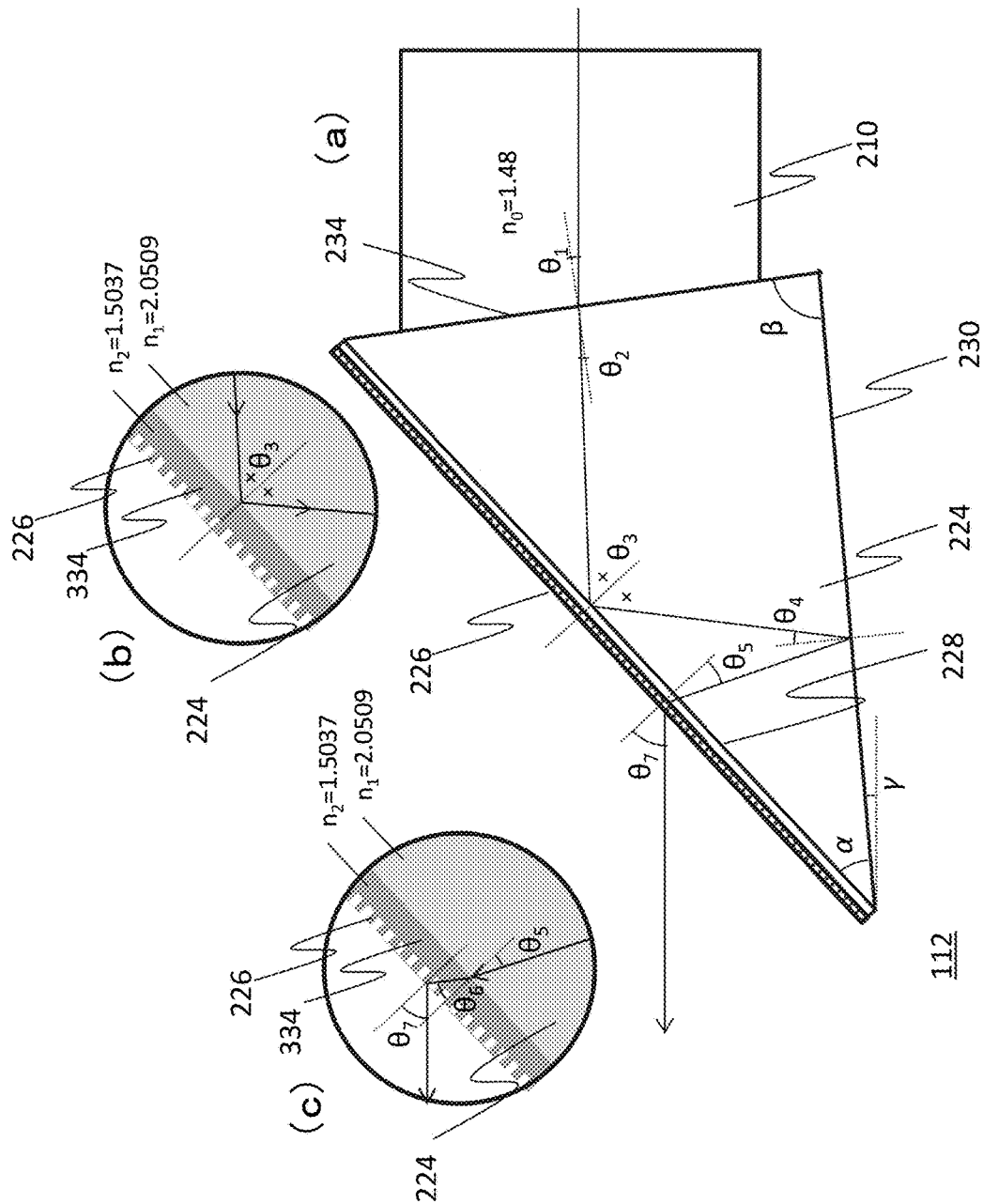
FIG. 15(a) shows an optical system in the eleventh embodiment.
FIG. 15(b) shows total internal reflection of light in the optical system of the eleventh embodiment.
FIG. 15(c) shows refraction and diffraction of light in the optical system of the eleventh embodiment.

In FIG. 15(a), a GRIN lens is used as the lens 210. An end surface of the GRIN lens is cut to an angle of 8 degrees. This angle of the end surface is effective in reducing the amount of returning light produced by reflection. Light that has become substantially parallel light by the GRIN lens (actually, the length of the GRIN lens is adjusted so as to be focused near a sample) is incident on a lens-support structure joint surface 234 at an angle $\theta_1$, and is refracted at an angle θ2. A refractive index no on the optical axis of the GRIN lens 210 is equal to 1.48, whereas the refractive index of the support structure 224 is approximately 2.05. Therefore, $\theta_1 > \theta_2$, and the inclination from the optical axis of the GRIN lens is at an angle of $\theta_1 - \theta_2$. The refracted light is incident on the first reflecting surface 228 at an angle $\theta_3$. In order for $\theta_3$ to be greater than the critical angle $\theta_{critical}$ such that the light incident on the first reflecting surface 228 at the angle $\theta_3$ is totally internally reflected, the refractive index of the support structure 224 and the refractive index of a thin layer 324 are selected, and the dimensions of the support structure 224 are determined. Compared to the case in which the end surface of the GRIN lens is not obliquely cut, the incidence angle $\theta_3$ with respect to the first reflecting surface 228 is greater by $\theta_1 - \theta_2$, so that the light is likely to be totally internally reflected. That is, this has the effect of allowing the use of a glass material having a refractive index that is lower than that of the support structure 224. As shown in FIG. 5(b), in the embodiment, the dispersive element 226 is a diffraction grating, and the thin layer 324 corresponds to a region of a member forming the diffraction grating that does not have a groove. The total internal reflection angle (critical angle) is calculated by using the above Formula (2).

The second reflecting surface 230 is coated so as to have a high reflectivity with respect to an incidence angle $\theta_4$ of the totally internally reflected light. After the totally internally reflected light has been reflected by the second reflecting surface 230, the light is incident again on the first reflecting surface at an angle $\theta_5$. In order for the angle $\theta_5$ to be smaller than the critical angle $\theta_{critical}$, the refractive index of the support structure 224 and the refractive index of the thin layer 334 are selected, and the dimensions of the support structure 224 are determined. As shown in FIG. 15(c), the light incident on the first reflecting surface 228 at the angle $\theta_5$ is refracted at an interface with the thin layer, and is transmitted at an angle $\theta_6$. The light incident on the diffraction grating 226 at the angle $\theta_6$ is diffracted at an angle $\theta_7$ that differs depending upon the wavelength thereof.

α and β denote the vertex angles of a glass prism of the support structure 224. γ denotes the inclination of the second reflecting surface 230 with respect to the optical axis of the GRIN lens.

In at least one embodiment, in order for total internal reflection to occur at the interface between the support structure 224 and the thin layer 334 while keeping the optical system compact, the refractive indices $n_1$ and $n_2$ thereof are selected preferably such that $$\frac{n_2}{n_1} < 0.8.$$

The reasons are as follows. When the diffraction grating 226 is directly formed on the first reflecting surface 228 of the support structure 224 by using, for example, replica resin, the refractive index of the thin layer 334 is $n_2$=1.3~1.6. On the other hand, in order for desired diffraction orders (in the embodiment, for the wavelength band for blue, a −6th order light is used; for the wavelength band for green, a −5th order light is used; and for the wavelength band for red, a −4th order light is used) to provide a sufficient diffraction efficiency for visible light, the incidence angle $\theta_6$ with respect to the diffraction grating in the thin layer 334 is 25 degrees ~40 degrees. When the vertex angles α and β of the glass prism are selected as appropriate, it is possible for $\theta_3$=about 40 degrees to about 55 degrees, which are suitable for the occurrence of total internal reflection. When $\theta_3$ is less than 40 degrees, even if a resin having a relatively low refractive index $n_2$ is selected for the thin layer 334, total internal reflection does not occur. In addition, the angle γ becomes too large, and the optical system loses its compactness. On the other hand, when $\theta_3$ is greater than 55 degrees, total internal reflection easily occurs, but the inclination of a light beam in the support structure 224 with respect to the optical axis of the GRIN lens becomes too large, as a result of which the optical system loses its compactness. Since $\theta_3$ must be made greater than the critical angle $\theta_{critical}$ by 1 to 2 degrees, on the basis of the condition of Formula (2), when $\theta_{critical}$<53°, considering the angle range of $\theta_3$ and the refractive index $n_2$ of the thin layer 334, for the refractive indices of the support structure 224 and the thin layer 334, it is preferable that $$\frac{n_2}{n_1} < 0.8,$$

and, more desirably $$\frac{n_2}{n_1} < 0.75.$$

In the embodiment, for the wavelength band for blue, a −6th order light is used; for the wavelength band for green, a −5th order light is used; and for the wavelength band for red, a −4th order light is used. When the diffraction angle is calculated from the incidence angle with respect to the dispersive element, the wavelengths of light that exist to a front surface of a probe and that illuminate the location Xj in FIG. 14 are 416 nm for blue, 498 nm for green, and 622 nm for red. On the other hand, when a half-viewing angle of the endoscope 100 is 27.5 degrees, the wavelengths of light that illuminate the location $X_N$ are 475 nm for blue, 569 nm for green, and 710 nm for red. That is, light detected by using the second waveguide 118 is spectrally dispersed into blue having a wavelength band of 416 nm~475 nm, green having a wavelength band of 498 nm~569 nm, and red having a wavelength band of 622 nm~710 nm, so that information about $X_1$~$X_N$ on the sample 116 is obtained.

Figure 16:
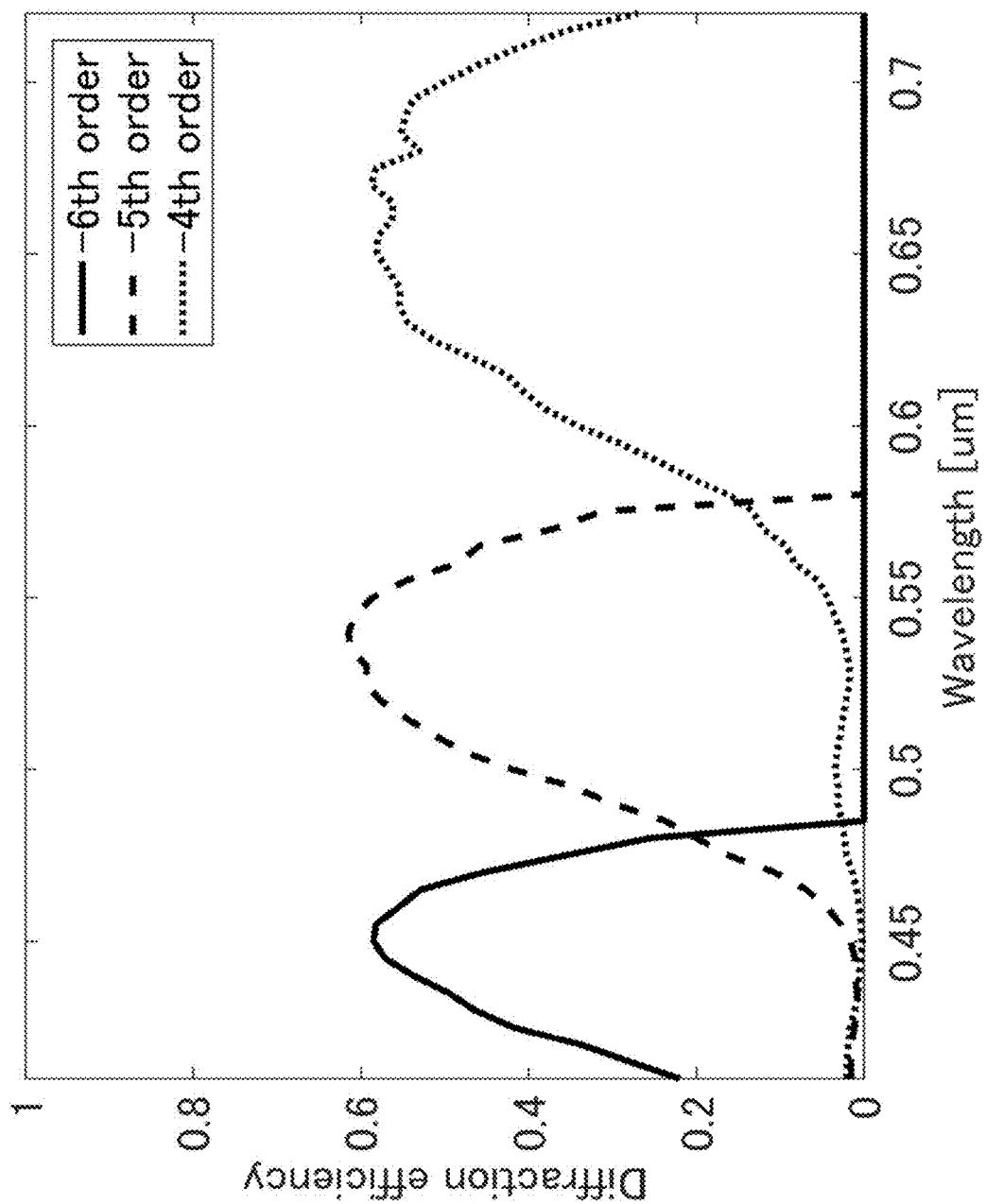
FIG. 16 shows the diffraction efficiency of a diffraction grating in at least the eleventh embodiment.

FIG. 16 shows the diffraction efficiency of the diffraction grating 226, designed so as to have a high diffraction efficiency in the aforementioned wavelength ranges, by using electromagnetic field analysis. The angle of propagation of a light beam in the diffraction grating is 36°, which corresponds to $\theta_6$ in Table 1. The diffraction efficiencies of the −6th order light, the −5th order light, and the −4th order light, which are used in at least the subject embodiment of the present disclosure, are high values in the aforementioned wavelength bands. The parameters of the diffraction grating 226 at this time are shown in Table 2. For example, the diffraction grating 226 is made of, for example, resin provided with grooves that are periodically formed in one direction. The duty ratio is a proportion of a region of the grooves (a region where the material forming the grating does not exist).

TABLE 2

| Parameters of Diffraction Grating 226 in one or more embodiments | |
| --- | --- |
| Pitch | 1.54 μm |
| Duty Ratio | 0.75 |
| Depth | 1.80 μm |
| Refractive Index | 1.50 |

Figure 17:
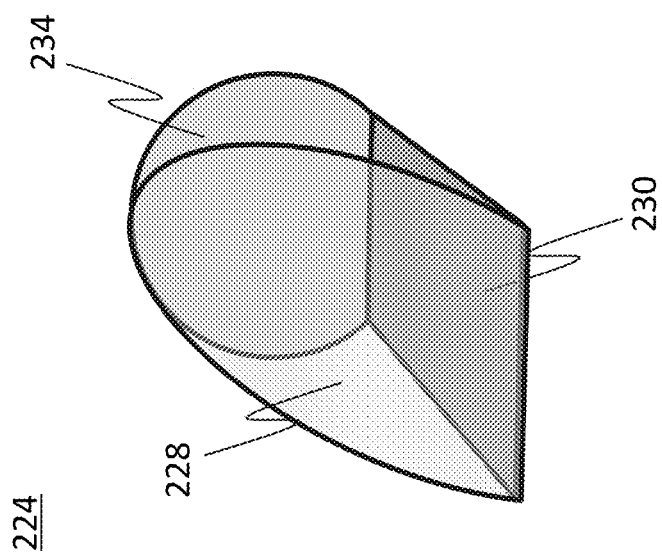
FIG. 17 shows a support structure in the eleventh embodiment.

FIG. 17 is a schematic view of the support structure 224 where the first reflecting surface 228, the second reflecting surface 230, and the lens-support structure joint surface are formed by cutting a column so as to form three planar surfaces.

Figure 18:
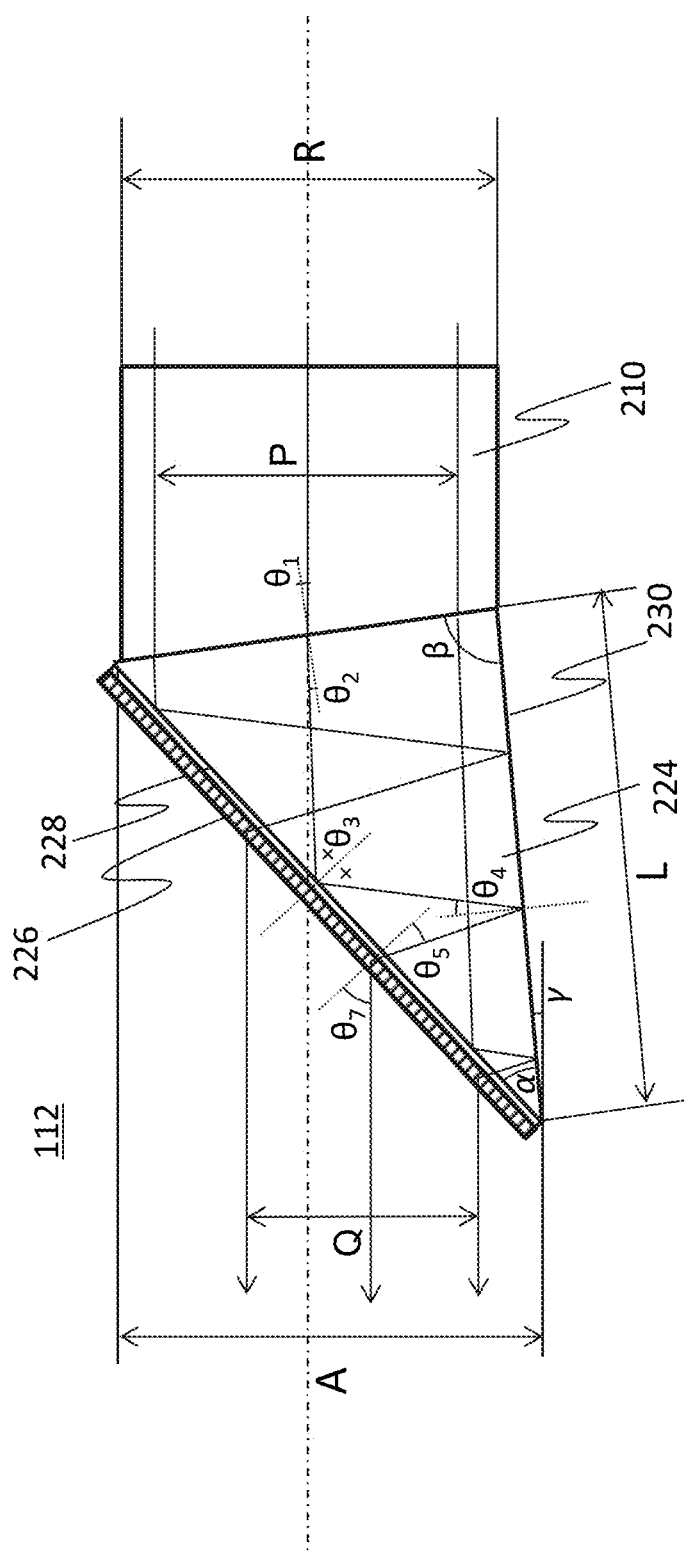
FIG. 18 shows the optical system of the eleventh embodiment.

Similarly to FIG. 15(a), FIG. 18 is a schematic view of the support structure 224 in FIG. 17 as seen in a cross section including the optical axis (direction of X in FIG. 14). $\theta_1$~$\theta_7$, α, β, and γ are the same as those in FIG. 15(a) and Table 1. When an effective light beam diameter in a spectral dispersion direction is P and an exiting light beam diameter from the diffraction grating is Q, the reduction ratio of a light beam diameter is expressed by Q/P.

Figure 19:
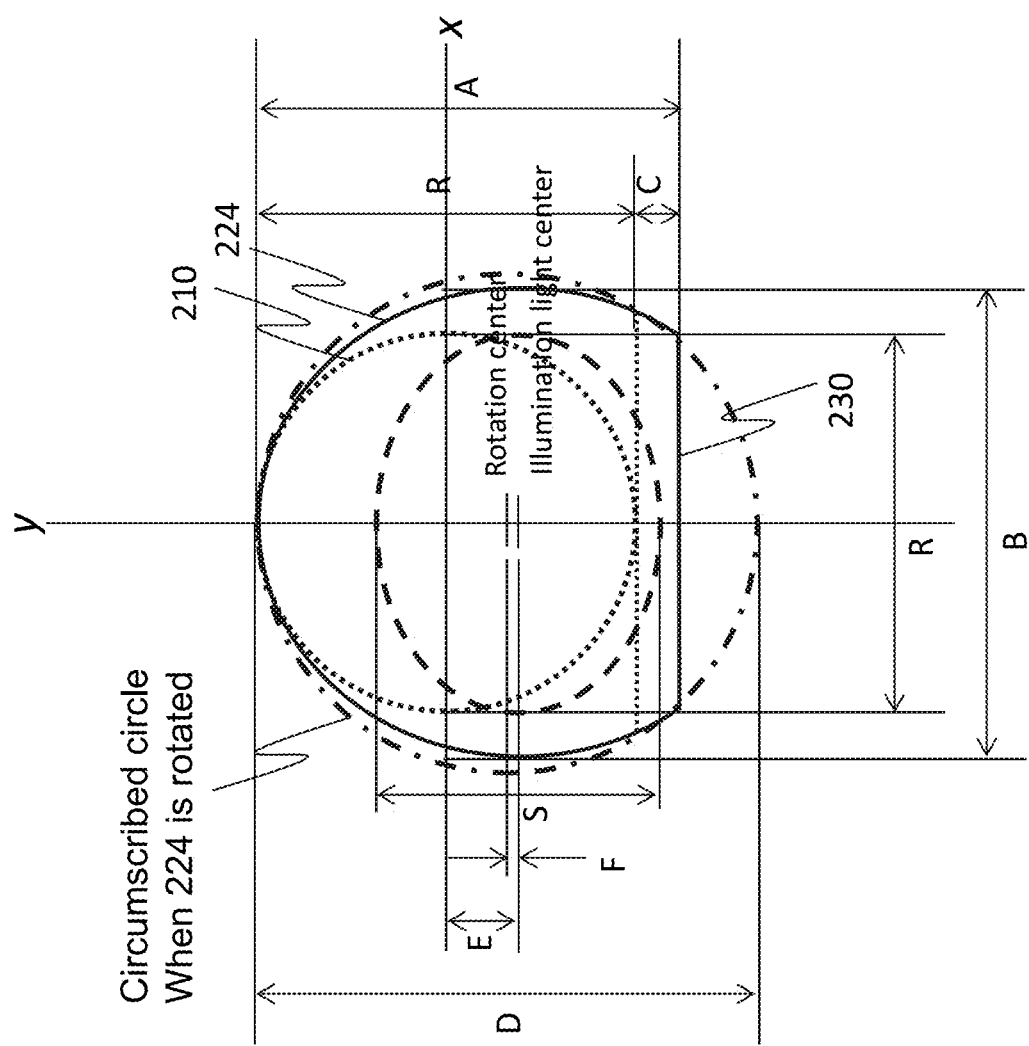
FIG. 19 shows the size of the support structure and the size of an exiting light beam in at least the eleventh embodiment.

In FIG. 19, in a schematic view in which the support structure 224 in FIG. 17 is seen from the optical axis (direction of Xj in FIG. 14), a y direction is a direction in which spectral dispersion occurs at the diffraction grating 226, and an x direction is a direction that is perpendicular to the plane of FIG. 14. In one or more embodiments, the circumscribed circle when the support structure 224 is rotated is an "envelope circle" which contacts the edge of the support structure, given that the support structure 224 is rotated.

Table 3 shows the dimensions of the support structure 224 and the size of the exiting light beam when a 250 μm GRIN lens is used.

TABLE 3

Size of Support Structure 224 and Size of Exiting Light Beam

| | Dimension (mm) | Remarks |
|---|---|---|
| A | 0.281 | element height (dimension in y-axis direction) |
| B | 0.314 | element width (dimension in x-axis direction) |
| C | 0.031 | |
| D | 0.330 | diameter of circumcircle when element has been rotated |
| E | 0.048 | center of exiting light beam |
| F | 0.008 | displacement between rotation center and center of exiting light beam |
| L | 0.341 | element length |
| R | 0.250 | diameter of GRIN lens, diameter of light beam in x-axis direction |
| S | 0.189 | light beam diameter in y-axis direction |

Reduction ratio (Q/P) of exiting light beam diameter: 0.755

One or more embodiments of the present disclosure use the first reflecting surface 228 as a total internal reflecting surface and a transmitting surface upon which light is incident again allows the size of the support structure 224 to be reduced to 0.33 mm, which does not differ much from the size of 0.25 mm of the GRIN lens. In addition, since an element length L is a small value of 0.341 mm, there are advantages in that an end of the probe is easily bent and the field of view of the endoscope is widened. Further, since γ is 5.20, which is small for design, the dimension of the support structure 224 is within approximately 0.28 mm, which is substantially equivalent to the diameter of the GRIN lens.

In one or more embodiments of the present disclosure, since the reduction ratio (Q/P) of the exiting light beam diameter in the spectral dispersion direction (y direction) is not considerably deteriorated, the spectral dispersion capability (size of a spot that is gathered on the sample 116) is not considerably deteriorated. In the embodiment, since the first reflecting surface 228 may be made wide, the manufacturing of the diffraction grating, such as replica molding, is facilitated.

A rotation center when the optical apparatus and/or system 112 is rotated to obtain a two dimensional image is the center of a circumcircle of 224 in the figure (see FIG. 19). A displacement F between the rotation center and the exiting light beam is to microns or less and is small. This decentering is such that Xj in FIG. 14 changes with each rotation angle, as a result of which a disturbance occurs in the two dimensional image. Ordinarily, in an image processor, this decentering needs to be corrected. However, in one or more embodiments of the present disclosure, since the decentering is small, it is not necessary to correct the decentering (in one or more other embodiments of the present disclosure, the decentering may be corrected by an image processor and/or computer, such as the computer 1300, 1300' discussed below). For those embodiments where the decentering may not be corrected, it is desirable that the displacement F between the rotation center and the exiting light beam be ¹/₁₀ or less of a diameter D of the circumcircle when the optical apparatus and/or system 112 has been rotated.

Figure 20:
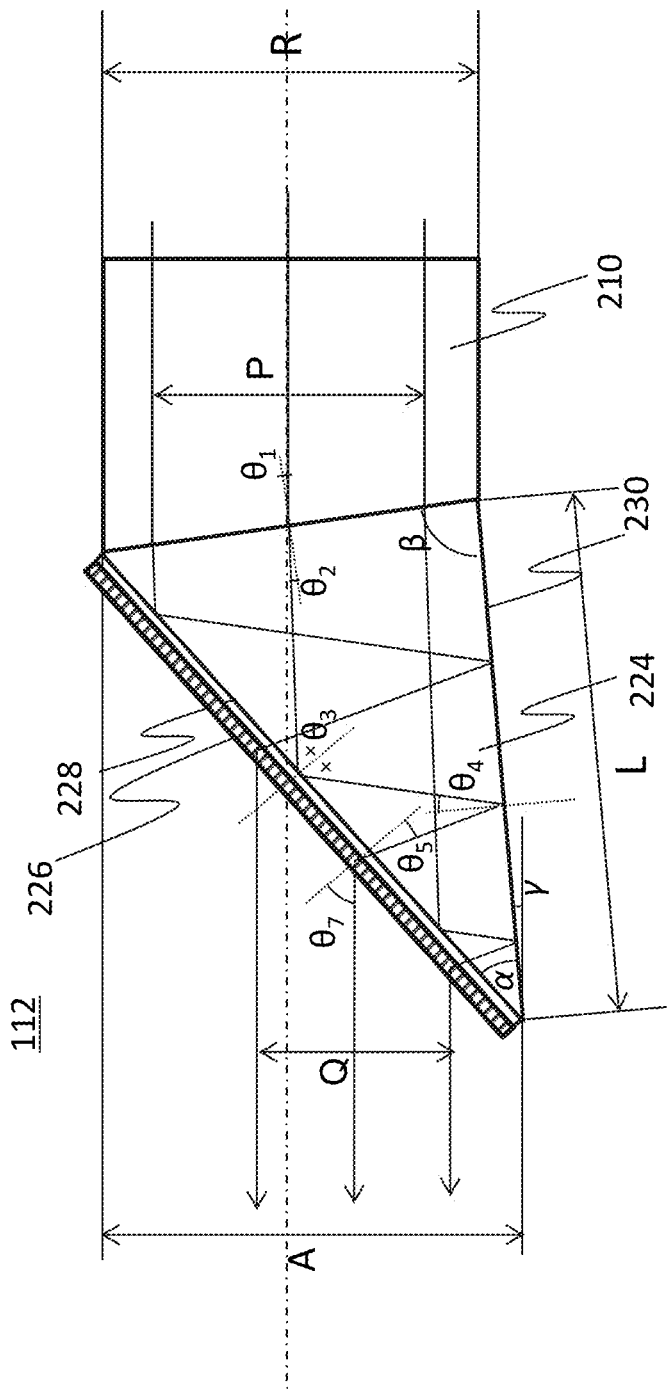
FIG. 20 shows an optical system of at least a twelfth embodiment.

A twelfth embodiment is described by using FIG. 20 and Tables 4 and 5. The description is confined to that of portions that differ from those according to at least the eleventh embodiment. The twelfth embodiment is an example of a design of a support structure 224 and a diffraction grating 226 when a glass material having a refractive index that is lower than that in at least the eleventh embodiment is used. The refractive index of the glass material is 2.0. An incidence angle $\theta_6$ with respect to the diffraction grating 226 is 33°, and is slightly smaller than that in the eleventh embodiment; and the diffraction grating is a 627-line/mm diffraction grating. FIG. 20 shows an optical system 112, which is a distinctive structure of the twelfth embodiment. The refractive index, the light beam angle, the angle of the support structure 224, and a grating constant of the diffraction grating are shown in Table 4.

TABLE 4

Example of Design in at least the Twelfth Embodiment

| | Refractive Index (nd) | Remarks |
|---|---|---|
| $n_0$ | 1.48 | GRIN lens |
| $n_1$ | 2.0010 | TAFD55, HOYA |
| $n_2$ | 1.5037 | UV cure resin |

| | Reflection/Refraction Angle | Remarks |
|---|---|---|
| $\theta_1$ | 8.0° | |
| $\theta_2$ | 5.91° | |
| $\theta_3$ | 50.01° | critical angle $\theta_{critical}$ = 48.75° |
| $\theta_4$ | 12.92° | |
| $\theta_5$ | 24.17° | |
| $\theta_6$ | 33.0° | |
| $\theta_7$ | 47.92° | |

| | Glass Vertex Angles, Etc. |
|---|---|
| α | 37.09° |
| β | 86.99° |
| γ | 4.99° |

Grating: 627 line/mm

Table 5 shows the dimensions of the support structure 224 and the size of an exiting light beam when a 250-micron GRIN lens is used. The items in Table 5 correspond to those in FIGS. 19 and 20. Compared to the eleventh embodiment in which a glass material having a higher refractive index is used, an incident light beam diameter with respect to the diffraction grating (beam shaping ratio) is slightly smaller, as a result of which imaging performance is slightly deteriorated.

TABLE 5

Size of Support Structure 224 and Size of Exiting Light Beam in at least Twelfth Embodiment

| | Dimension (mm) | Remarks |
|---|---|---|
| A | 0.280 | element height (dimension in y-axis direction) |
| B | 0.314 | element width (dimension in x-axis direction) |
| C | 0.030 | |
| D | 0.330 | diameter of circumcircle when element has been rotated |
| E | 0.050 | center of exiting light beam |
| F | 0.010 | displacement between rotation center and center of exiting light beam |
| L | 0.347 | element length |
| R | 0.250 | diameter of GRIN lens, diameter of light beam in x-axis direction |
| S | 0.185 | light beam diameter in y-axis direction |

Reduction ratio (Q/P) of exiting light beam diameter: 0.738

Figure 21:
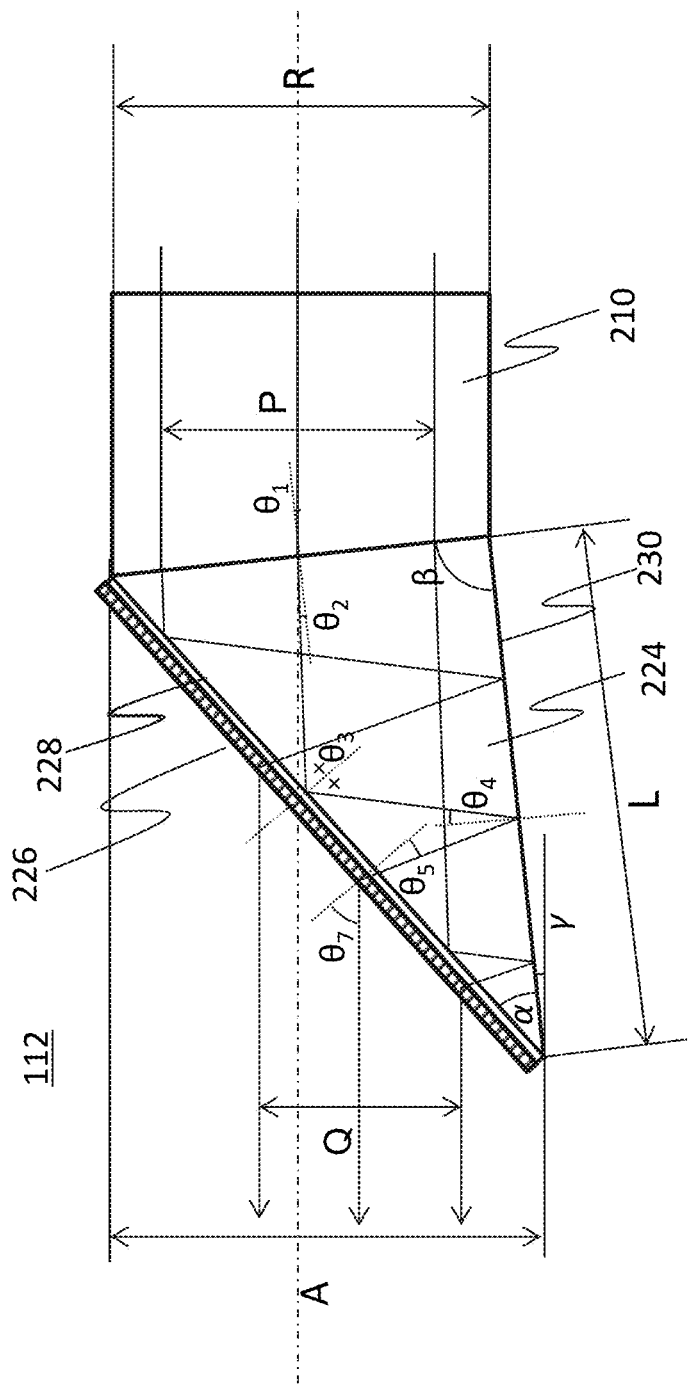
FIG. 21 shows an optical system of at least a thirteenth embodiment.

At least a thirteenth embodiment is described by using FIG. 21 and Tables 6 and 7. The description is confined to that of portions that differ from those according to the eleventh embodiment. In the thirteenth embodiment, a cut angle of an end surface of a GRIN lens is changed to 5.57° and an angle β of a spacer is a right angle, so that a structure that allows processing costs of the spacer to be reduced is provided. An incidence angle $\theta_6$ with respect to a diffraction grating 226 and line/mm of the diffraction grating are the same as those according to the twelfth embodiment. FIG. 21 shows an optical system 112, which is a distinctive structure of the thirteenth embodiment. Table 6 shows the refractive index, the light beam angle, the angle of a support structure 224, and a grating constant of the diffraction grating.

TABLE 6

Example of Design of Thirteenth Embodiment

| | Refractive Index (nd) | Remarks |
|---|---|---|
| $n_0$ | 1.48 | GRIN lens |
| $n_1$ | 2.0509 | TAFD65, HOYA |
| $n_2$ | 1.5037 | UV cure resin |

| | Reflection/Refraction Angle | Remarks |
|---|---|---|
| $\theta_1$ | 5.57° | |
| $\theta_2$ | 4.02° | |
| $\theta_3$ | 49.47° | critical angle $\theta_{critical}$ = 47.18° |
| $\theta_4$ | 12.96° | |
| $\theta_5$ | 23.55° | |
| $\theta_6$ | 33.0° | |
| $\theta_7$ | 47.92° | |

| Glass Vertex Angles, Etc. | |
|---|---|
| α | 36.51° |
| β | 90.0° |
| γ | 5.57° |

Grating: 627 line/mm

Table 7 shows the dimensions of the support structure 224 and the size of an exiting light beam when a 250-micron GRIN lens is used. The items in Table 7 correspond to those in FIGS. 19 and 21.

TABLE 7

Size of Support Structure 224 and Size of Exiting Light Beam in Thirteenth Embodiment

| | Dimension (mm) | Remarks |
|---|---|---|
| A | 0.283 | element height (dimension in y-axis direction) |
| B | 0.313 | element width (dimension in x-axis direction) |
| C | 0.033 | |
| D | 0.330 | diameter of circumcircle when element has been rotated |
| E | 0.049 | center of exiting light beam |
| F | 0.009 | displacement between rotation center and center of exiting light beam |
| L | 0.339 | element length |
| R | 0.250 | diameter of GRIN lens, diameter of light beam in x-axis direction |
| S | 0.183 | light beam diameter in y-axis direction |

Reduction ratio (Q/P) of exiting light beam diameter: 0.733

Figure 22:
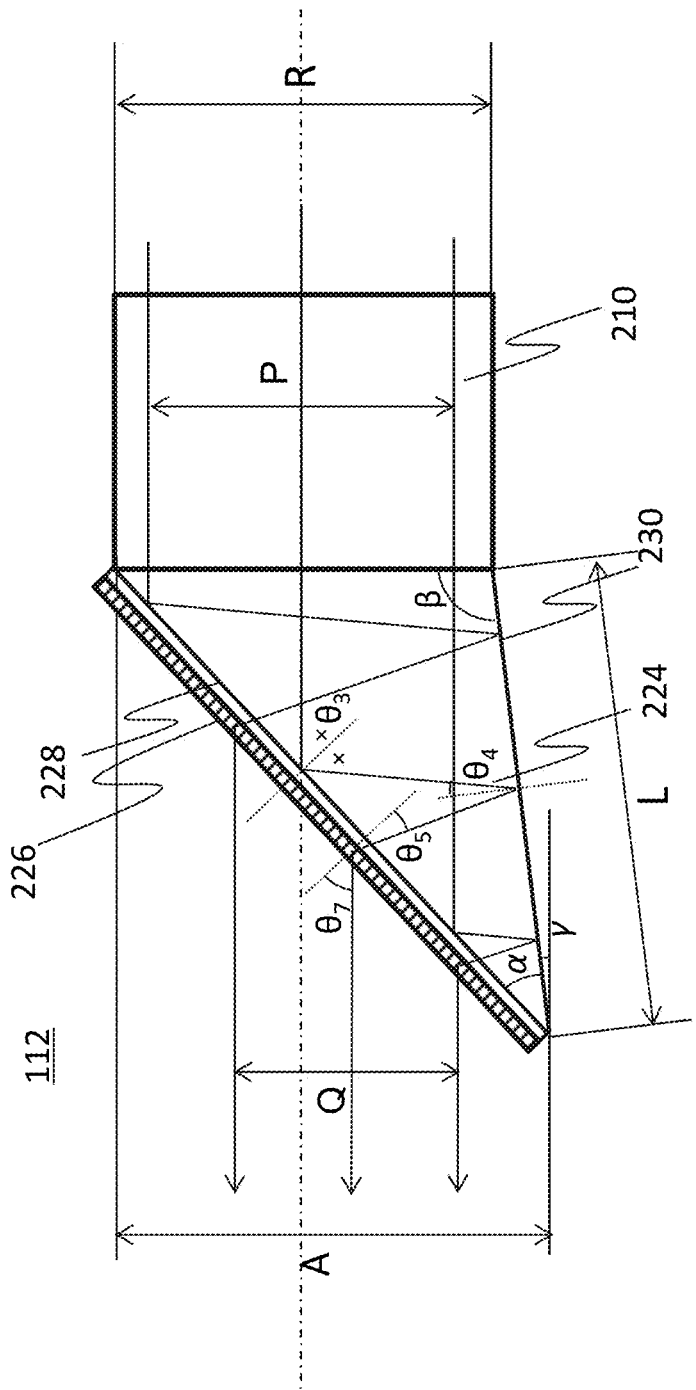
FIG. 22 shows an optical system of at least a fourteenth embodiment.

A fourteenth embodiment is described by using FIG. 22 and Tables 8 and 9. The description is confined to that of portions that differ from those according to the eleventh embodiment. The fourteenth embodiment is an example of a design of a support structure 224 and a diffraction grating 226 when a glass material having a refractive index that is higher than that in the eleventh embodiment is used. The refractive index of the glass material is 2.1. Further, there is no cut in an end surface of a GRIN lens (0°), and the number of processing steps of the GRIN lens is reduced. Due to the influence of the glass material having a high refractive index, the transmissivity of a spacer at a short wavelength end is slightly lower. FIG. 22 shows an optical system 112, which is a distinctive structure of the fourteenth embodiment. Table 8 shows the refractive index, the light beam angle, the angle of the support structure 224, and a grating constant of the diffraction grating.

TABLE 8

Example of Design of Fourteenth Embodiment

| | Refractive Index (nd) | Remarks |
|---|---|---|
| $n_0$ | 1.48 | GRIN lens |
| $n_1$ | 2.10195 | LBBH1, OHARA |
| $n_2$ | 1.5037 | UV cure resin |

| | Reflection/Refraction Angle | Remarks |
|---|---|---|
| $\theta_1$ | 0.0° | |
| $\theta_2$ | 0.0° | |
| $\theta_3$ | 47.28° | critical angle $\theta_{critical}$ = 45.73° |
| $\theta_4$ | 11.2° | |
| $\theta_5$ | 24.89° | |
| $\theta_6$ | 36.0° | |
| $\theta_7$ | 47.28° | |

| Glass Vertex Angles, Etc. | |
|---|---|
| α | 36.09° |
| β | 96.64° |
| γ | 6.64° |

Grating: 650 line/mm

Table 9 shows the dimensions of the support structure 224 and the size of an exiting light beam when a ϕ250-micron GRIN lens is used. The items in Table 9 correspond to those in FIG. 18. An element length L is smaller than those in the previous embodiments, and a structure that allows an end portion of a probe to be more easily bent is provided.

TABLE 9

Size of Support Structure 224 and Size of Exiting Light Beam in Fourteenth Embodiment

| | Dimension (mm) | Remarks |
|---|---|---|
| A | 0.286 | element height (dimension in y-axis direction) |
| B | 0.312 | element width (dimension in x-axis direction) |
| C | 0.036 | |
| D | 0.335 | diameter of circumcircle when element has been rotated |
| E | 0.041 | center of exiting light beam |
| F | 0.002 | displacement between rotation center and center of exiting light beam |
| L | 0.312 | element length |
| R | 0.250 | diameter of GRIN lens, diameter of light beam in x-axis direction |
| S | 0.187 | light beam diameter in y-axis direction |

Reduction ratio (Q/P) of exiting light beam diameter: 0.748

Figure 23:
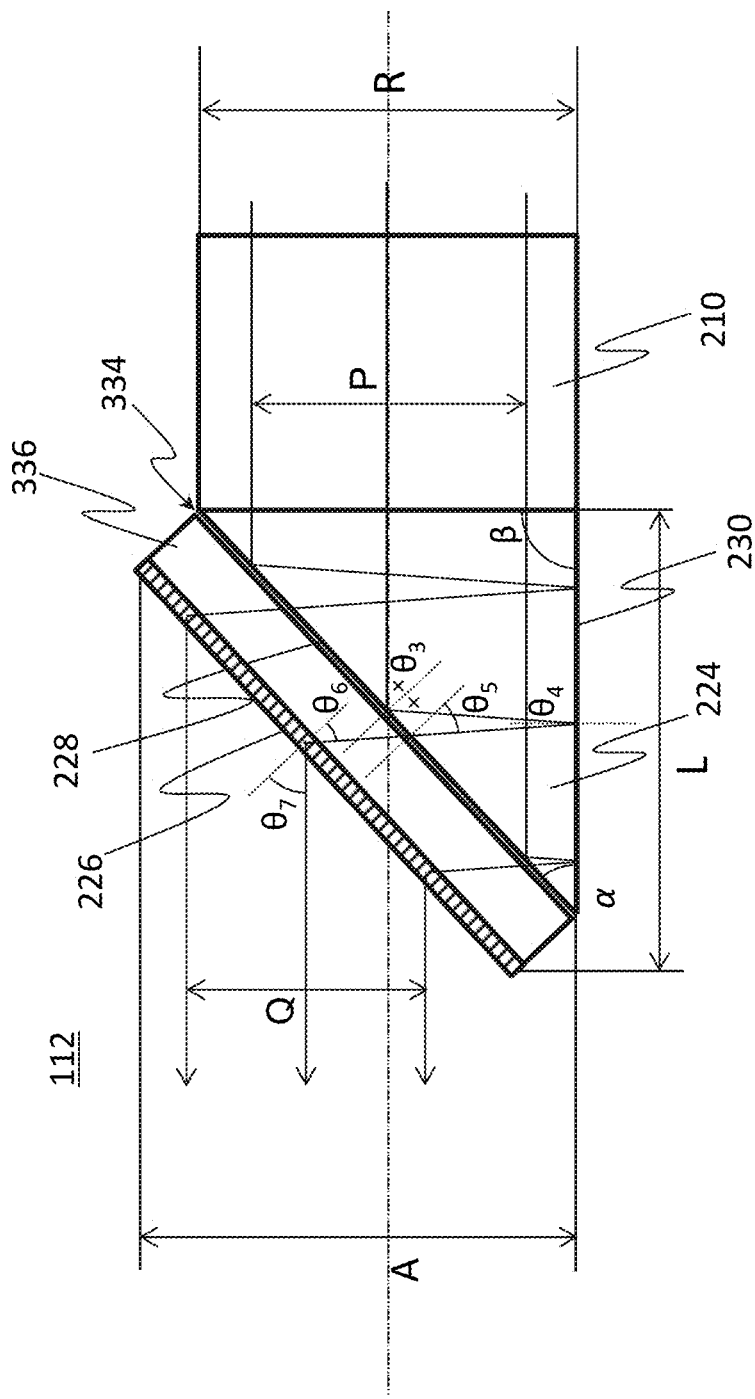
FIG. 23 shows an optical system of at least an fifteenth embodiment.
Figure 25:
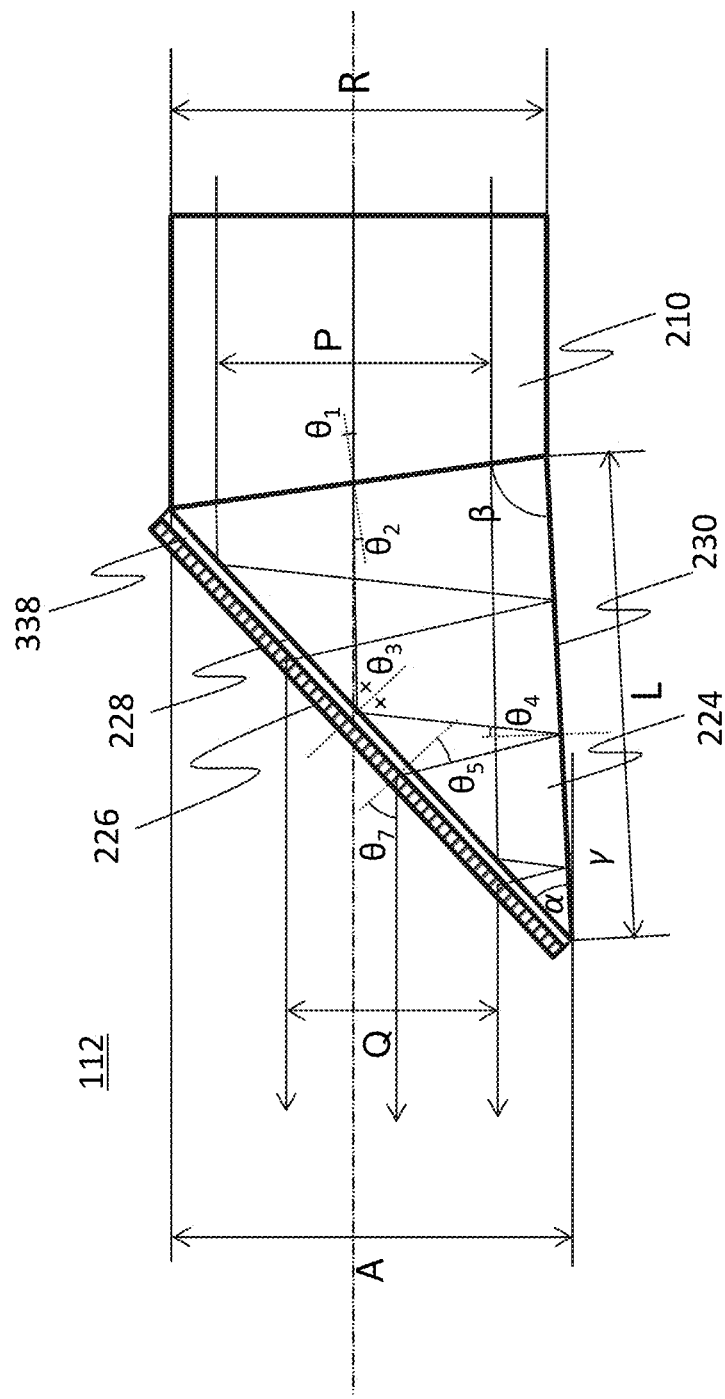
FIG. 25 shows an optical system of at least a sixteenth embodiment.

A fifteenth embodiment is described by using FIG. 23 and Tables 10 and 11. The description is confined to that of portions that differ from those of at least the eleventh embodiment. In the fifteenth embodiment, an air gap is used as a thin layer 334 next to the support material 224 in order to, in one or more embodiments, use quartz for glass material of a support structure 224 (rather than a high refractive index glass) and still have a total internal reflection upon the first incidence to the surface 228. In one or more embodiments, the air gap 334 may be formed and maintained by spacers or protrusions on the support material positioned at the periphery of the cover glass, or a ring or oval spacer at the periphery of the optics (not shown). Alternatively, the mount for the distal optics may be made with steps or ridges inside so as to maintain the space for the air gap 334 upon mounting. In addition, in the embodiment, in order to support a diffraction grating 226, a cover glass 336 (made of quartz) having a thickness of 50 microns is used. There is a thin layer of air gap 334 in between the cover glass 336 and the support structure 224. In order to prevent the effect of repeated interference from occurring, and suppress the height of an element, the air gap has a size that is a few times to a few tens of times the wavelength of illumination light. More specifically, it is preferably approximately 5 μm to 20 μm. Further, there is no additional angled polishing on the end surface of a GRIN lens 210 (0°), and the number of processing steps of the GRIN lens is reduced. Further, the support structure 224 can be a right-angle prism, and is suitable for low-cost production. An incidence angle θ6 with respect to the diffraction grating 226 is 37°, and is slightly larger than that in the eleventh embodiment; and the diffraction grating is a 658-line/mm diffraction grating. FIG. 23 shows an optical system 112, which is a distinctive structure of the fifteenth embodiment. Table 10 shows the refractive index, the light beam angle, the angle of the support structure 224, and a grating constant of the diffraction grating. In one or more embodiments, grating 226 (e.g., as shown in FIG. 23, FIG. 25 discussed below, etc.) either may be just the groove layer or the grating 226 may be a grating and the underlying layer of the same material, in addition to the air gap, glass cover, and/or thin layer.

Even if $n_2=1.0\sim1.3$ for the refractive index of the thin layer 334, in order for total internal reflection to occur at an interface between the support structure 224 and the thin layer 334 while keeping the optical system compact, the respective refractive indices $n_1$ and $n_2$ are selected such that $$\frac{n_2}{n_1} < 0.8,$$

and, more desirably, such that $$\frac{n_2}{n_1} < 0.75.$$

In one or more embodiments, the thin layer 334 may include more structure than the air gap only.

TABLE 10

Example of Design of Fifteenth Embodiment

| | Refractive Index (nd) | Remarks |
|---|---|---|
| $n_0$ | 1.48 | GRIN lens |
| $n_1$ | 1.458 | Quartz (spacer, cover G) |
| $n_2$ | 1.00 | Air |
| $n_3$ | 1.5037 | UV cure resin |

| | Reflection/Refraction Angle | Remarks |
|---|---|---|
| $\theta_1$ | 0.0° | |
| $\theta_2$ | 0.0° | |
| $\theta_3$ | 47.27° | critical angle $\theta_{critical} = 43.3°$ |
| $\theta_4$ | 4.45° | |
| $\theta_5$ | 38.37° | |
| $\theta_6$ | 37.0° | |
| $\theta_7$ | 47.18° | |

| | Glass Vertex Angles, Etc. | |
|---|---|---|
| α | 42.82° | |
| β | 90.0° | |
| γ | 0.0° | |

Grating: 658 line/mm

Figure 24:
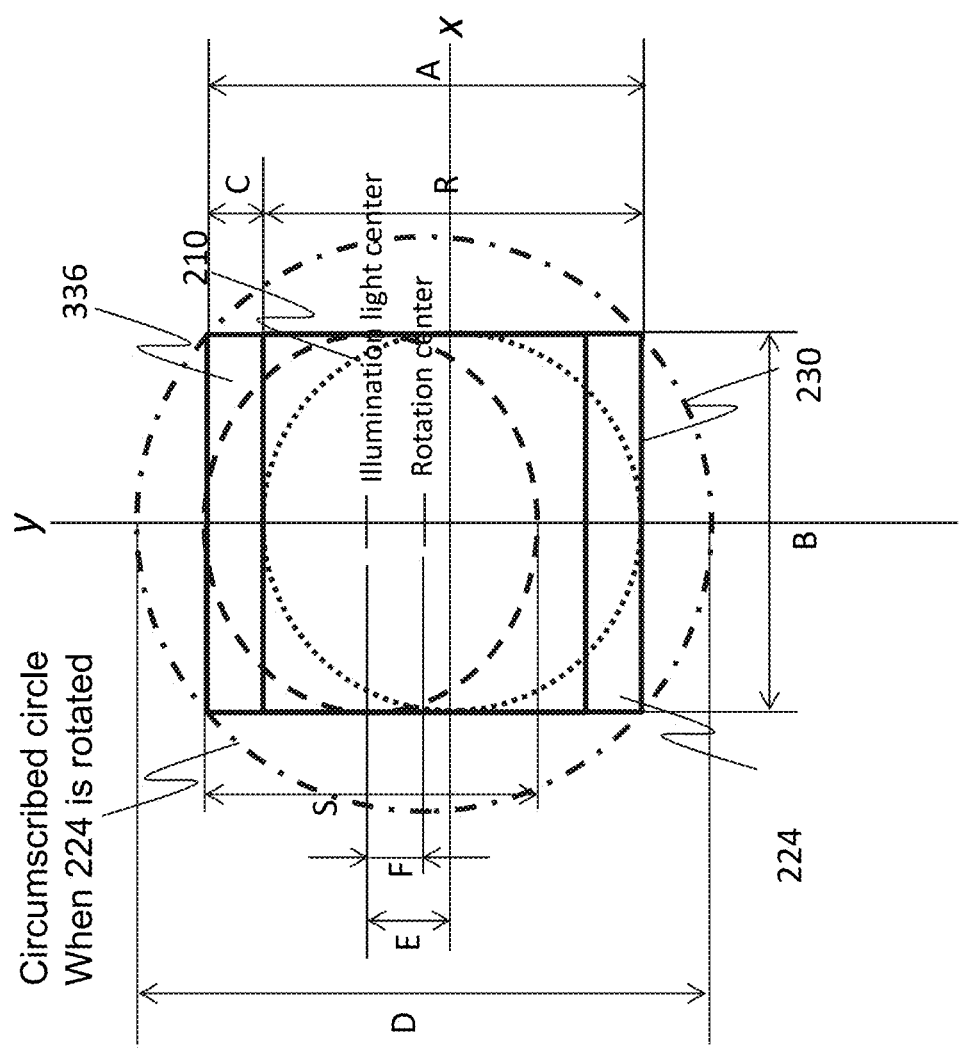
FIG. 24 shows the size of a support structure and the size of an exiting light beam in at least the fifteenth embodiment.

In FIG. 24, in a schematic view in which the support structure 224 in FIG. 22 is seen from the optical axis (direction of X in FIG. 14), a y direction in the figure is a direction in which spectral dispersion occurs at the diffraction grating 226, and an x direction in the figure is a direction that is perpendicular to the plane of FIG. 14. The table shows the dimensions of the support structure 224 and the size of an exiting light beam when a 250 μm GRIN lens is used. In one or more embodiments, the circumscribed circle when the support structure 224 is rotated is an "envelope circle" which contacts the edge of the support structure, given that the support structure 224 is rotated (see FIG. 24).

Table 11 shows the dimensions of the support structure 224 and the size of the exiting light beam when the 25o-micron GRIN lens is used. The items in Table 11 correspond to those in FIGS. 23 and 24. Whereas an element length L is 305 microns and the element is compact, a cover glass is required. Therefore, an element height D is increased, and an outside diameter D of the support structure becomes approximately 380 μm. By chamfering four corners, it is possible to slightly reduce the outside diameter. In the embodiment, since a reduction ratio (Q/P) of an exiting light beam diameter in the spectral dispersion direction (y direction) is approximately 0.87 and large, it is possible to minimize the deterioration in spectral dispersion capability (size of a spot that is gathered on a sample 116).

TABLE 11

Size of Support Structure 224 and Size of Exiting Light Beam in Fifteenth Embodiment

| | Dimension (mm) | Remarks |
|---|---|---|
| A | 0.290 | element height (dimension in y-axis direction) |
| B | 0.250 | element width (dimension in x-axis direction) |
| C | 0.036 | |
| D | 0.380 | diameter of circumcircle when element has been rotated |
| E | 0.054 | center of exiting light beam |
| F | 0.038 | displacement between rotation center and center of exiting light beam |
| L | 0.305 | element length |
| R | 0.250 | diameter of GRIN lens, diameter of light beam in x-axis direction |
| S | 0.217 | light beam diameter in y-axis direction |

Reduction ratio (Q/P) of exiting light beam diameter: 0.867

Figure 26:
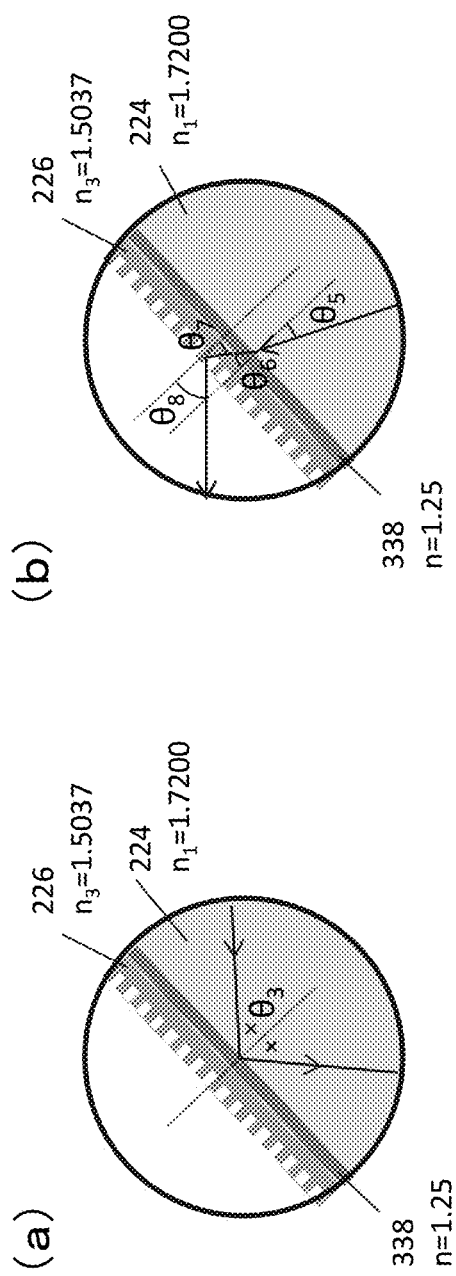
FIG. 26(a) shows total internal reflection of light in the optical system of at least the sixteenth embodiment.
FIG. 26(b) shows refraction and diffraction of light in the optical system of at least the sixteenth embodiment.

A sixteenth embodiment is described by using FIGS. 25 and 26(a)-(b) and Tables 12 and 13. The description is confined to that of portions that differ from those according to the eleventh embodiment. In the sixteenth embodiment, by using a material containing silica-based hollow fine particles (described in, for example, U.S. Pat. No. 5,686,604) as a thin layer 338, a glass material of a support structure 224 is a glass material having a refractive index of 1.72. In this case, since a diffraction grating 226 can be formed on the thin layer 338, a cover glass as that in the fifteenth embodiment is not required. FIG. 25 shows an optical system 112, which is a distinctive structure of the sixteenth embodiment. As aforementioned, in one or more embodiments, grating 226 (e.g., as shown in FIG. 23, FIG. 25, etc.) either may be just the groove layer or the grating 226 may be a grating and the underlying layer of the same material, in addition to the air gap, glass cover, and/or thin layer. FIGS. 26(a)-(b) are enlarged views of a low-refractive-index layer containing silica-based hollow fine particles (thin layer 338). The thickness of the low-refractive-index layer containing silica-based hollow fine particles needs to be approximately 5 μm, which is sufficiently larger than the wavelength. FIG. 26(a) shows, at a first reflecting surface 228, a total internal reflection of light emitted from a lens 210. FIG. 26(b) shows refraction/transmission of light incident again upon the first reflecting surface 228 via a second reflecting surface 230o. Table 12 shows the refractive index, the light beam angle, the angle of the support structure 224, and a grating constant of the diffraction grating.

TABLE 12

Example of Design of Sixteenth Embodiment

| | Refractive Index (nd) | Remarks |
|---|---|---|
| $n_0$ | 1.48 | GRIN lens |
| $n_1$ | 1.7200 | S-LAM52, OHARA |
| $n_2$ | 1.25 | Silica-based hollow fine particle thin Layer, JGC CATALYSTS AND CHEMICALS CO., LTD. |
| $n_3$ | 1.5037 | UV cure resin |

| | Reflection/Refraction Angle | Remarks |
|---|---|---|
| $\theta_1$ | 8.0° | |
| $\theta_2$ | 6.88° | |
| $\theta_3$ | 48.40° | critical angle $\theta_{critical}$ = 46.61° |
| $\theta_4$ | 8.74° | |
| $\theta_5$ | 30.92° | |
| $\theta_6$ | 44.99° | |
| $\theta_7$ | 36.0° | |
| $\theta_8$ | 47.28° | |

| Glass Vertex Angles, Etc. | |
|---|---|
| α | 39.66° |
| β | 85.06° |
| γ | 3.06° |

Grating: 650 line/mm

Table 13 shows the dimensions of the support structure 224 and the size of an exiting light beam when a φ250-micron GRIN lens is used. The items in Table 13 correspond to those in FIGS. 19 and 25. In the embodiment, the support structure has an outside diameter D of approximately 320 microns, and is very compact, so that the support structure is suitable for use as an endoscope having a small diameter.

TABLE 13

Size of Support Structure 224 and Size of Exiting Light Beam in Sixteenth Embodiment

| | Dimension (mm) | Remarks |
|---|---|---|
| A | 0.267 | element height (dimension in y-axis direction) |
| B | 0.313 | element width (dimension in x-axis direction) |
| C | 0.017 | |
| D | 0.320 | diameter of circumcircle when element has been rotated |
| E | 0.035 | center of exiting light beam |
| F | 0.001 | displacement between rotation center and center of exiting light beam |
| L | 0.325 | element length |
| R | 0.250 | diameter of GRIN lens, diameter of light beam in x-axis direction |
| S | 0.198 | light beam diameter in y-axis direction |

Reduction ratio (Q/P) of exiting light beam diameter: 0.793

Figure 27:
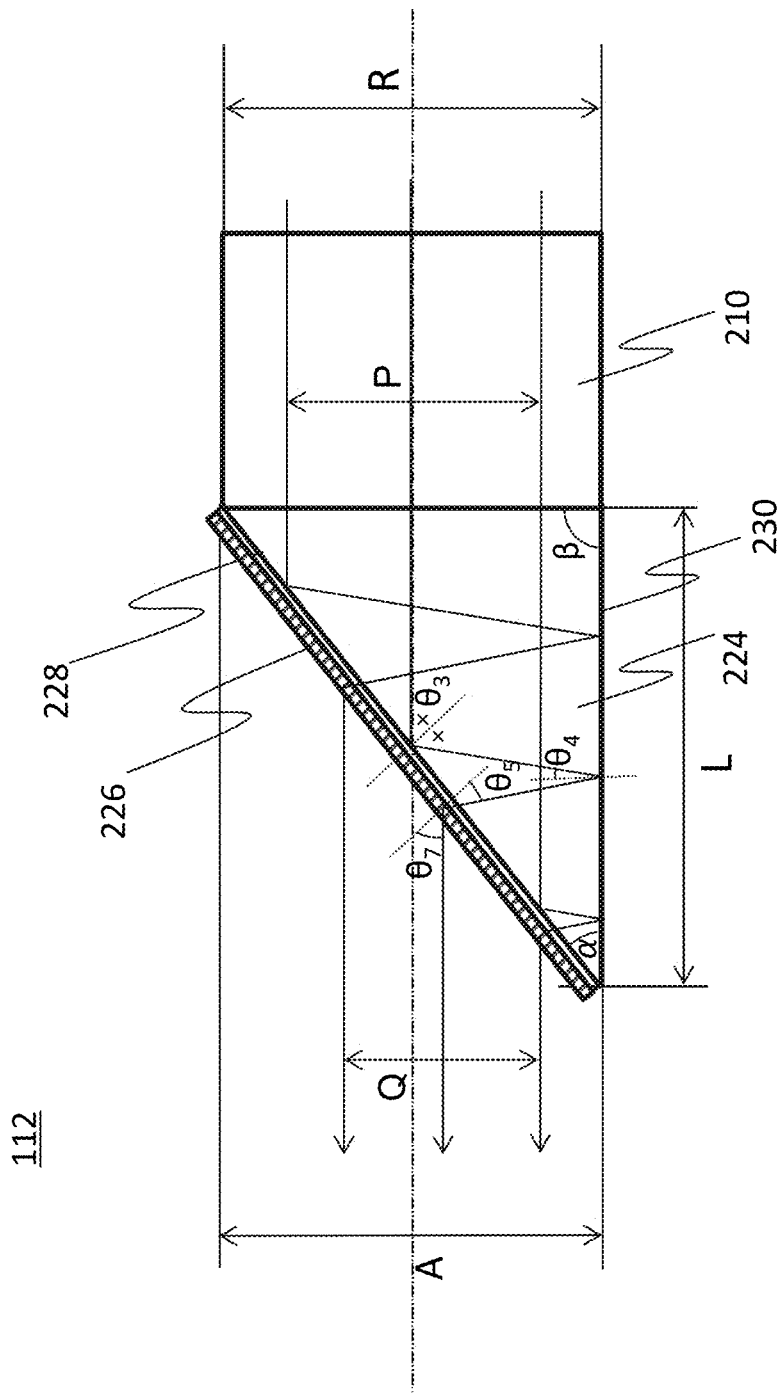
FIG. 27 shows an optical system of at least a seventeenth embodiment.
Figure 28:
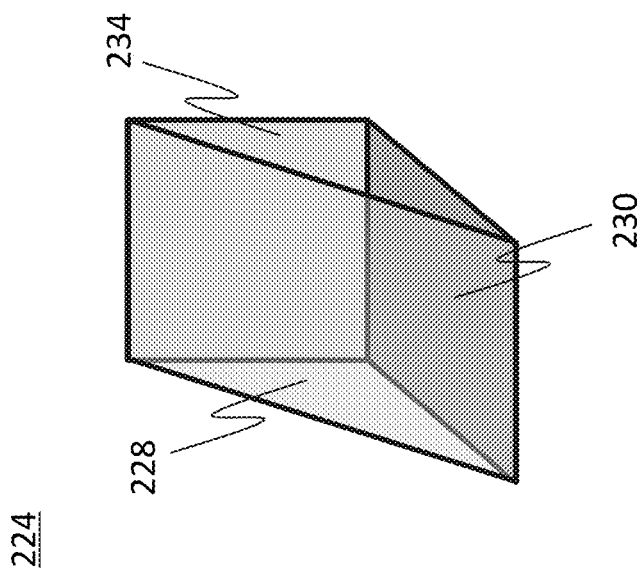
FIG. 28 shows a support structure in at least the seventeenth embodiment.

A seventeenth embodiment is described by using FIGS. 27 and 28 and Tables 14 and 15. The description is confined to that of portions that differ from those according to the eleventh embodiment. In the seventeenth embodiment, a cut angle of an end surface of a GRIN lens is 0° and an angle β of a spacer is a right angle. Further, as shown in FIG. 28, a support structure 224 has a form in which a rectangular parallelepiped is cut in two at a first reflecting surface 228, and further, in the embodiment, a support structure joint surface 234 has a square shape. In this way, by forming the support structure 224 with a simple form, it is possible to not only reduce processing costs but also reduce manufacturing errors and provide stable quality (diffraction efficiency and wavelength band used).

Figure 29:
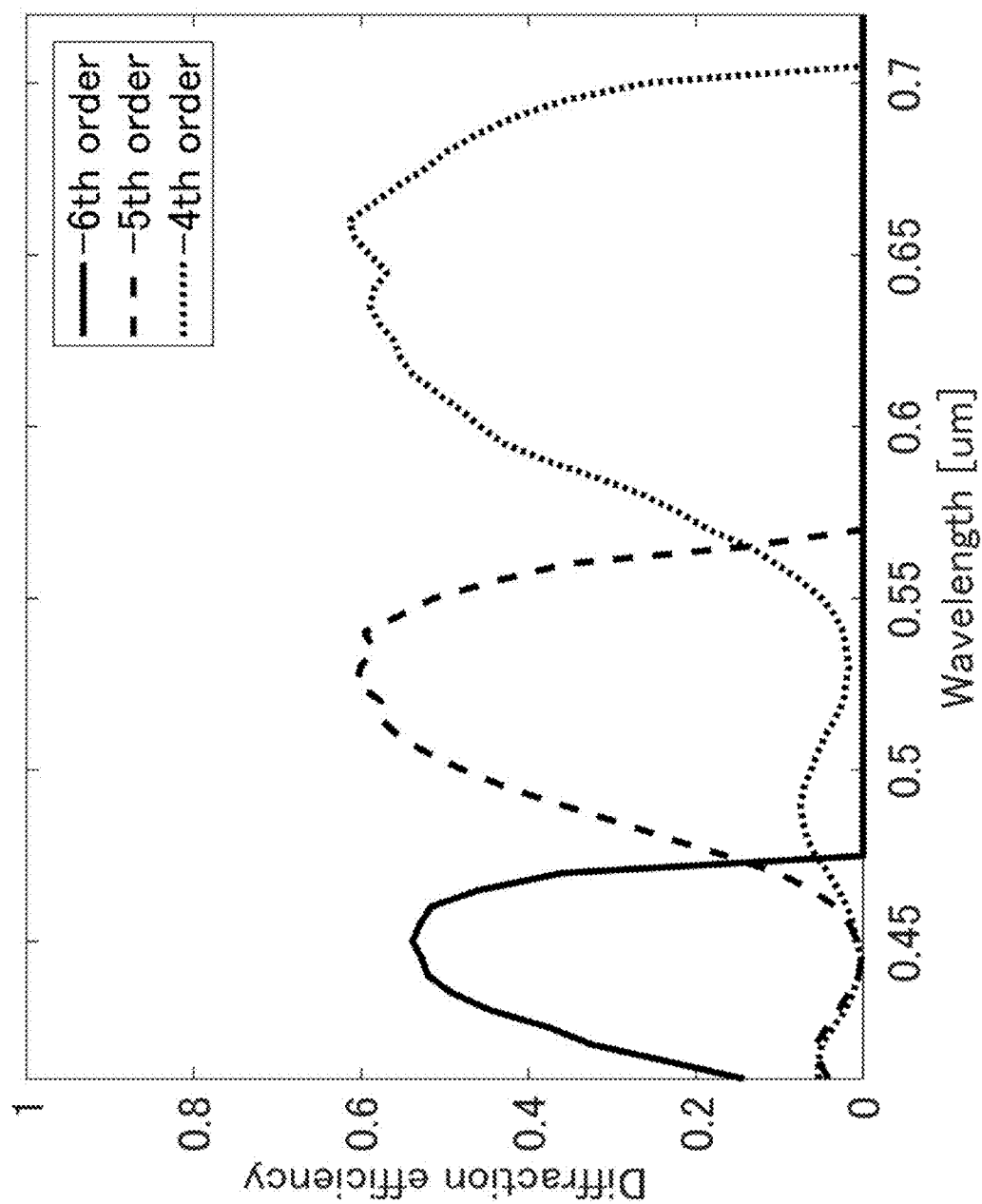
FIG. 29 shows the diffraction efficiency of a diffraction grating in at least the seventeenth embodiment.

FIG. 27 shows an optical system 112, which is a distinctive structure of the seventeenth embodiment. Table 14 shows the refractive index, the light beam angle, the angle of the support structure 224, and a grating constant of the diffraction grating. In the embodiment, unlike in the previous embodiments, the wavelength bands that are used are 422.6~470.1 nm for a −6th order light, 502.4~560.5 nm for a −5th order light, and 623.5~697.2 nm for a −4th order light. By using a diffraction grating having the structure shown in FIG. 27 and the parameters shown in Table 2, the diffraction efficiency of the aforementioned wavelength bands becomes 20% or greater. Further, by making side walls of the diffraction grating angular by a few degrees, the diffraction efficiency of the aforementioned wavelength bands becomes 30% or greater. FIG. 29 shows the results in which the diffraction efficiency when the side walls of the diffraction grating are made angular is obtained by using electromagnetic field analysis.

TABLE 14

Example of Design of Seventeenth Embodiment

| | Refractive Index (nd) | Remarks |
|---|---|---|
| $n_0$ | 1.48 | GRIN lens |
| $n_1$ | 2.0509 | TAFD65, HOYA |
| $n_2$ | 1.5037 | UV cure resin |

| | Reflection/Refraction Angle | Remarks |
|---|---|---|
| $\theta_1$ | 0° | |
| $\theta_2$ | 0° | |
| $\theta_3$ | 52.0° | critical angle $\theta_{critical}$ = 47.15° |
| $\theta_4$ | 14.0° | |
| $\theta_5$ | 24.0° | |
| $\theta_6$ | 33.69° | |
| $\theta_7$ | 52.0° | |

| Glass Vertex Angles, Etc. | |
|---|---|
| α | 38.0° |
| β | 90.0° |
| γ | 0.0° |

Grating: 650 line/mm

Table 15 shows the dimensions of the support structure 224 and the size of an exiting light beam when a φ250-micron GRIN lens is used. The items in Table 15 correspond to those in FIGS. 24 and 27. Item C related to the thickness of a cover glass is zero because it corresponds to the thickness of the diffraction grating in the embodiment.

In the embodiment, the size of the GRIN lens and the size of the support structure are the same, and a rotation center of the optical system 112 is the center of the GRIN lens and the support structure. Therefore, in the embodiment, the structure of the optical system 102 has a structure that is easy to assemble. Although, a displacement (item F) between the rotation center and the center of the exiting light beam is larger in this embodiment than in the other embodiments, depending upon the distance to a subject and the resolution of an image, it is an allowable amount. Although there is a disadvantage in that the outside diameter of the optical system 112 becomes large, when the rotation center of the optical system 102 is made to coincide with the center of the exiting light beam instead of the center of the support structure, this displacement between the centers can be cancelled.

TABLE 15

Size of Support Structure 224 and Size of Exiting Light Beam in Seventeenth Embodiment

| | Dimension (mm) | Remarks |
|---|---|---|
| A | 0.250 | element height (dimension in y-axis direction) |
| B | 0.250 | element width (dimension in x-axis direction) |
| C | 0 | |
| D | 0.354 | diameter of circumcircle when element has been rotated |
| E | 0.041 | center of exiting light beam |
| F | 0.041 | displacement between rotation center and center of exiting light beam |
| L | 0.320 | element length |
| R | 0.250 | diameter of GRIN lens, diameter of light beam in x-axis direction |
| S | 0.168 | light beam diameter in y-axis direction |

Reduction ratio (Q/P) of exiting light beam diameter: 0.674

Although preferred embodiments of the present invention are described above, the present invention is not limited to these embodiments, so that various modifications and changes can be made within the scope of the gist thereof.

Figure 30:
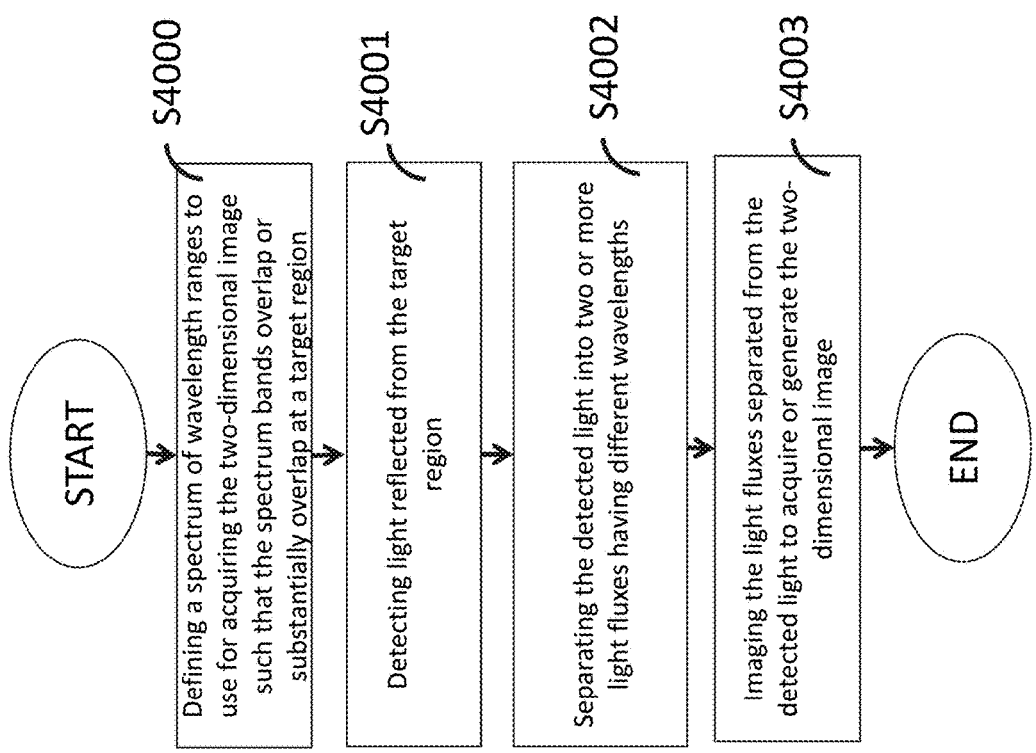
FIG. 30 is a flow diagram showing a method of performing an imaging technique in accordance with one or more aspects of the present disclosure.

In accordance with one or more aspects of the present disclosure, one or more methods for performing imaging are provided herein. FIG. 30 illustrates a flow chart of at least one embodiment of a method for performing imaging. Preferably, the method(s) may include one or more of the following: (i) defining a spectrum of wavelength ranges to use for acquiring the image such that the spectrum bands overlap or substantially overlap on a sample or target (see step S4000 in FIG. 30); (ii) detecting light reflected from the target region (see step S4000 in FIG. 30); (iii) separating the detected light into two or more light fluxes having different wavelengths (see step S4002 in FIG. 30); and imaging the light fluxes separated from the detected light to acquire or generate the black and white and/or color image (see step S4003 in FIG. 30). One or more methods may further include at least one of: using a probe grating to generate the spectrum bands that overlap or substantially overlap on the target region; and optimizing the probe grating so that a diffraction efficiency is high within the wavelength ranges. In one or more embodiments, a SEE probe may be connected to one or more systems (e.g., the system 100, the system 100', the system 100", etc.) with a connection member or interface module. For example, when the connection member or interface module is a rotary junction for a SEE probe, the rotary junction may be at least one of: a contact rotary junction, a lenseless rotary junction, a lens-based rotary junction, or other rotary junction known to those skilled in the art. The rotary junction may be a one channel rotary junction or a two channel rotary junction. In one or more embodiments, the illumination portion of the SEE probe may be separate from the detection portion of the SEE probe. For example, in one or more applications, a probe may refer to the illumination assembly, which includes the illumination fiber 108 (e.g., single mode fiber, a GRIN lens, a spacer and the grating on the polished surface of the spacer, etc.). In one or more embodiments, a scope may refer to the illumination portion which, for example, may be enclosed and protected by a drive cable, a sheath, and detection fibers (e.g., multimode fibers (MMFs)) around the sheath. Grating coverage is optional on the detection fibers (e.g., MMFs) for one or more applications. The illumination portion may be connected to a rotary joint and may be rotating continuously at video rate. In one or more embodiments, the detection portion may include one or more of: the detection fiber 118, the spectrometer 120, the computer 1300, the computer 1300', the image processor 122, etc. The detection fibers, such as the detection fiber(s) 118, may surround the illumination fiber, such as the IF 108, and the detection fibers may or may not be covered by the grating, such as the grating 107.

Unless otherwise discussed herein, like numerals indicate like elements. For example, while variations or differences exist between the systems, such as, but not limited to, the system 100, the system 100', the system 100", etc., one or more features thereof may be the same or similar to each other, such as, but not limited to, the light source 102 or other component(s) thereof (e.g., the console 1300, the console 1300', the RJ 106, etc.). Those skilled in the art will appreciate that the light source 102, the RJ 106, the MCU 140, the spectrometer 120 (one or more components thereof) and/or one or more other elements of the system 100, may operate in the same or similar fashion to those like-numbered elements of one or more other systems, such as, but not limited to, the system 100', the system 100", etc. as discussed herein. Those skilled in the art will appreciate that alternative embodiments of the system 100, the system 100', the system 100", etc., and/or one or more like-numbered elements of one of such systems, while having other variations as discussed herein, may operate in the same or similar fashion to the like-numbered elements of any of the other systems (or components thereof) discussed herein. Indeed, while certain differences exist between the system 100, the system 100', the system 100", and the other system(s) as discussed herein, there are similarities. Likewise, while the console or computer 1300 may be used in one or more systems (e.g., the system 100, the system 100', the system 100", etc.), one or more other consoles or computers, such as the console or computer 1300', the image processor 122, etc., may be used additionally or alternatively.

Light emitted by a white light source may be transmitted by an illumination light transmission fiber and may be incident on a probe portion via the RJ 106. Additionally or alternatively, the light emitted by the white light source may be transmitted by the illumination light transmission fiber and may be incident on the probe portion (e.g., the optical apparatus and/or system 112) via a deflecting or deflected section 117 and via the RJ 106. Reflected light from the spectral sequence (e.g., light from the spectral sequence that is formed on, and is reflected by, the subject or sample; light that is reflected by the subject or sample; etc.) is taken in by a detection fiber or cable, such as the cable or fiber 118. Although one detection fiber may be used in one or more embodiments, a plurality of detection fibers may be used additionally or alternatively. In one or more embodiments, the detection fiber may extend to and/or near the end of the probe section. For example, the detection fiber 118 may have a detection fiber portion (e.g., a fiber extending through the probe portion) that extends from or through the RJ 106 through, and to and/or near (e.g., adjacent to the end of the probe section, about the end of the probe portion, near the end of the probe portion closest to the sample, etc.) the end of, the probe section (e.g., the optical apparatus and/or system 112). The light taken in by the detection fiber 118 is separated into spectral components and detected by at least one detector, such as, but not limited to, a spectrometer 120 (and/or one or more components thereof as discussed herein), provided at the exit side of the detection fiber 118. In one or more embodiments, the end of the detection fiber 118 that takes in the reflected light may be disposed on or located near at least one of: the diffraction grating 107, the end of the spacer 111, the end of the probe portion 112, etc. Additionally or alternatively, the reflected light may be passed at least one of: through the probe portion, through the GRIN lens, through the rotary junction, etc., and the reflected light may be passed, via a deflecting or deflected section 117 (discussed below), to the spectrometer 120. As the portion extending from the RJ 106 to the probe portion 112 is rotated about the rotational axis extending in the longitudinal direction of the probe portion 112, the spectral sequence moves in a direction orthogonal to the spectral sequence, and reflectance information in two-dimensional directions may be obtained. Arraying these pieces (e.g., the reflectance information in two-dimensional directions) of information makes it possible to obtain a two-dimensional image.

Preferably, in one or more embodiments including the deflecting or deflected section 117, the deflected section 117 operates to deflect the light from the light source 102 to the probe portion (e.g., element 112), and then send light received from the probe portion towards at least one detector (e.g., the spectrometer 120, one or more components of the spectrometer 120, etc.). In one or more embodiments, the deflected section 117 may include or may comprise one or more interferometers or optical interference systems that operate as described herein, including, but not limited to, a circulator, a beam splitter, an isolator, a coupler (e.g., fusion fiber coupler), a partially severed mirror with holes therein, a partially severed mirror with a tap, etc. In one or more embodiments, the interferometer or the optical interference system may include one or more components of the system or of the system, such as, but not limited to, one or more of the light source 102, the deflected section 117, the rotary junction 106, and/or the probe portion (e.g., element 112) (and/or one or more components thereof).

The rotary junction 106 may be a one channel rotary junction or a two channel rotary junction. In one or more embodiments, the illumination portion of the probe may be separate from the detection portion of the probe. For example, in one or more applications, a probe may refer to the illumination assembly, which includes an illumination fiber (e.g., single mode fiber, a GRIN lens, a spacer and the grating on the polished surface of the spacer, etc.). In one or more embodiments, a scope may refer to the illumination portion which, for example, may be enclosed and protected by a drive cable, a sheath, and detection fibers (e.g., multimode fibers (MMFs)) around the sheath. Grating coverage is optional on the detection fibers (e.g., MMFs) for one or more applications. The illumination portion may be connected to a rotary joint and may be rotating continuously at video rate. In one or more embodiments, the detection portion operating to obtain the image data may include one or more of: the detection fiber 118, the spectrometer 120, a computer 1300, the computer 1300' (as discussed further below), etc.

There are many ways to compute intensity, viscosity, resolution (including increasing resolution of one or more images), creation of color images or any other measurement discussed herein, digital as well as analog. In at least one embodiment, a computer, such as the console or computer 1300, 1300', may be dedicated to control and monitor the SEE devices, systems, methods and/or storage mediums described herein.

The electric signals used for imaging may be sent to one or more processors, such as, but not limited to, an image processor 122 as discussed above (see e.g., FIGS. 1A and 12), a computer 1300 (see e.g., FIGS. 1B-1C and 31), a computer 1300' (see e.g., FIG. 32), etc. as discussed further below, via cable(s) or wire(s), such as, but not limited to, the cable(s) or wire(s) 113 (see FIG. 31).

Figure 31:
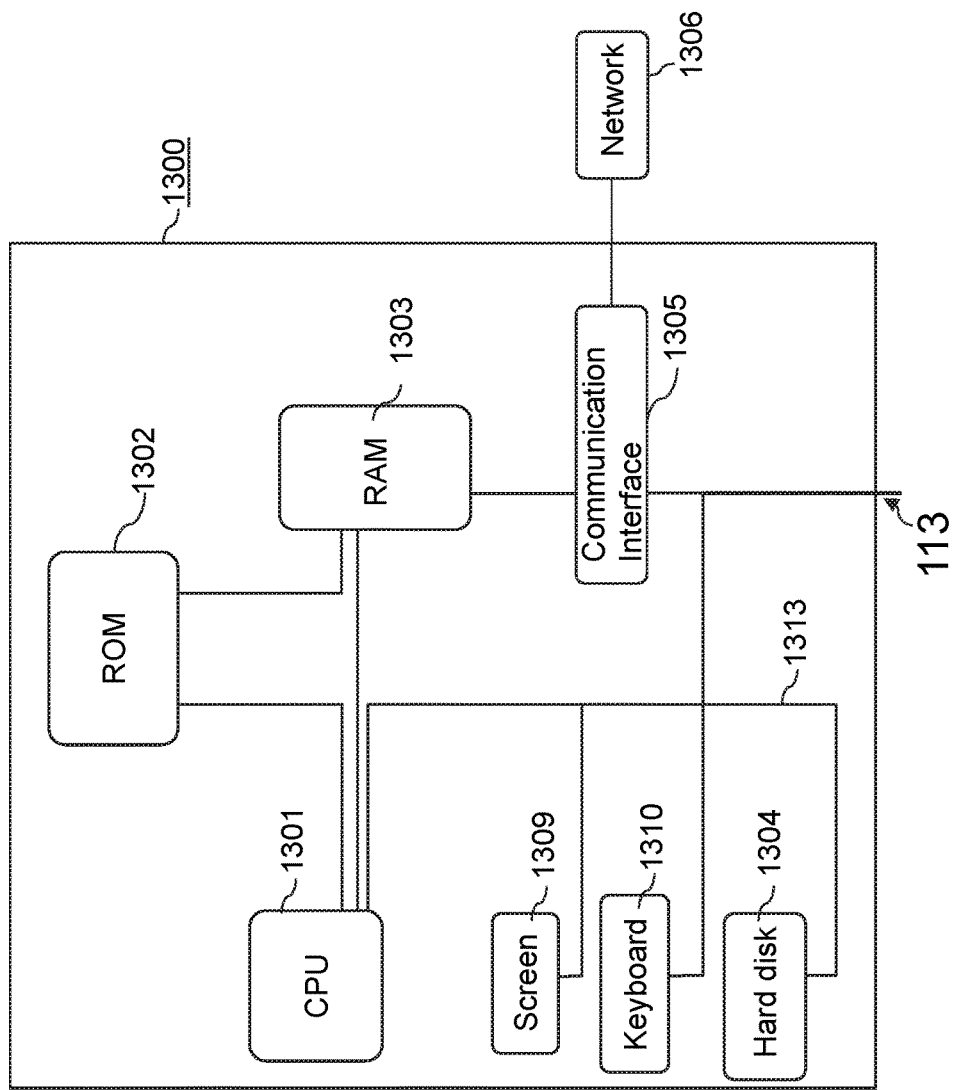
FIG. 31 shows a schematic diagram of an embodiment of a computer that may be used with one or more embodiments of a SEE apparatus or system or an imaging system or one or more methods discussed herein in accordance with one or more aspects of the present disclosure.

Various components of a computer system 1300 (see e.g., the console or computer 1300 as shown in FIGS. 1B-1C) are provided in FIG. 31. A computer system 1300 may include a central processing unit ("CPU") 1301, a ROM 1302, a RAM 1303, a communication interface 1305, a hard disk (and/or other storage device) 1304, a screen (or monitor interface) 1309, a keyboard (or input interface; may also include a mouse or other input device in addition to the keyboard) 1310 and a BUS or other connection lines (e.g., connection line 1313) between one or more of the aforementioned components (e.g., including but not limited to, being connected to the console, the probe, any motor discussed herein, a light source, etc.). In addition, the computer system 1300 may comprise one or more of the aforementioned components. For example, a computer system 1300 may include a CPU 1301, a RAM 1303, an input/output (I/O) interface (such as the communication interface 1305) and a bus (which may include one or more lines 1313 as a communication system between components of the computer system 1300; in one or more embodiments, the computer system 1300 and at least the CPU 1301 thereof may communicate with the one or more aforementioned components of a device or system, such as, but not limited to, a system using a motor, a rotary junction, etc.), and one or more other computer systems 1300 may include one or more combinations of the other aforementioned components (e.g., the one or more lines 1313 of the computer 1300 may connect to other components via line 113). The CPU 1301 is configured to read and perform computer-executable instructions stored in a storage medium. The computer-executable instructions may include those for the performance of the methods and/or calculations described herein. The system 1300 may include one or more additional processors in addition to CPU 13o1, and such processors, including the CPU 1301, may be used for tissue or sample characterization, diagnosis, evaluation and/or imaging. The system 1300 may further include one or more processors connected via a network connection (e.g., via network 1306). The CPU 1301 and any additional processor being used by the system 1300 may be located in the same telecom network or in different telecom networks (e.g., performing technique(s) discussed herein may be controlled remotely).

Figure 32:
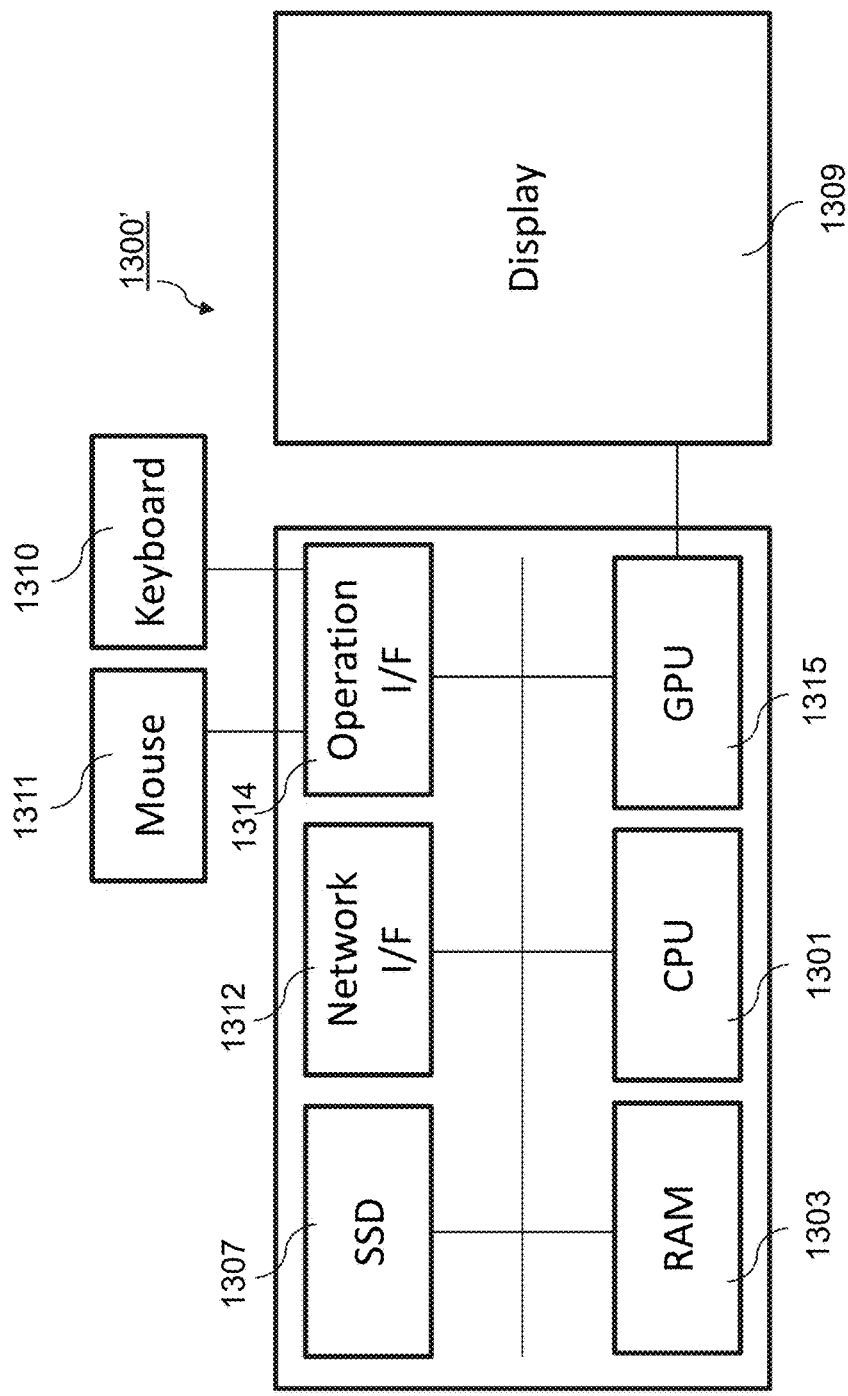
FIG. 32 shows a schematic diagram of another embodiment of a computer that may be used with one or more embodiments of a SEE apparatus or system or an imaging system or methods discussed herein in accordance with one or more aspects of the present disclosure.

The I/O or communication interface 1305 provides communication interfaces to input and output devices, which may include a light source, a spectrometer, the communication interface of the computer 1300 may connect to other components discussed herein via line 113 (as diagrammatically shown in FIG. 31), a microphone, a communication cable and a network (either wired or wireless), a keyboard 1310, a mouse (see e.g., the mouse 1311 as shown in FIG. 32), a touch screen or screen 1309, a light pen and so on. The Monitor interface or screen 1309 provides communication interfaces thereto.

Any methods and/or data of the present disclosure, such as the methods for performing tissue or sample characterization, diagnosis, examination and/or imaging (including, but not limited to, increasing image resolution) as discussed herein, may be stored on a computer-readable storage medium. A computer-readable and/or writable storage medium used commonly, such as, but not limited to, one or more of a hard disk (e.g., the hard disk 1304, a magnetic disk, etc.), a flash memory, a CD, an optical disc (e.g., a compact disc ("CD") a digital versatile disc ("DVD"), a Blu-Ray™ disc, etc.), a magneto-optical disk, a random-access memory ("RAM") (such as the RAM 1303), a DRAM, a read only memory ("ROM"), a storage of distributed computing systems, a memory card, or the like (e.g., other semiconductor memory, such as, but not limited to, a non-volatile memory card, a solid state drive (SSD) (see SSD 1307 in FIG. 32), SRAM, etc.), an optional combination thereof, a server/database, etc. may be used to cause a processor, such as, the processor or CPU 1301 of the aforementioned computer system 1300 to perform the steps of the methods disclosed herein. The computer-readable storage medium may be a non-transitory computer-readable medium, and/or the computer-readable medium may comprise all computer-readable media, with the sole exception being a transitory, propagating signal in one or more embodiments. The computer-readable storage medium may include media that store information for predetermined or limited or short period(s) of time and/or only in the presence of power, such as, but not limited to Random Access Memory (RAM), register memory, processor cache(s), etc. Embodiment(s) of the present disclosure may also be realized by a computer of a system or apparatus that reads out and executes computer executable instructions (e.g., one or more programs) recorded on a storage medium (which may also be referred to more fully as a "non-transitory computer-readable storage medium") to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s).

In accordance with at least one aspect of the present disclosure, the methods, systems, and computer-readable storage mediums related to the processors, such as, but not limited to, the processor of the aforementioned computer 1300, etc., as described above may be achieved utilizing suitable hardware, such as that illustrated in the figures. Functionality of one or more aspects of the present disclosure may be achieved utilizing suitable hardware, such as that illustrated in FIG. 31. Such hardware may be implemented utilizing any of the known technologies, such as standard digital circuitry, any of the known processors that are operable to execute software and/or firmware programs, one or more programmable digital devices or systems, such as programmable read only memories (PROMs), programmable array logic devices (PALs), etc. The CPU 1301 (as shown in FIG. 31) may also include and/or be made of one or more microprocessors, nanoprocessors, one or more graphics processing units ("GPUs"; also called a visual processing unit ("VPU")), one or more Field Programmable Gate Arrays ("FPGAs"), or other types of processing components (e.g., application specific integrated circuit(s) (ASIC)). Still further, the various aspects of the present disclosure may be implemented by way of software and/or firmware program(s) that may be stored on suitable storage medium (e.g., computer-readable storage medium, hard drive, etc.) or media (such as floppy disk(s), memory chip(s), etc.) for transportability and/or distribution. The computer may include a network of separate computers or separate processors to read out and execute the computer executable instructions. The computer executable instructions may be provided to the computer, for example, from a network or the storage medium.

As aforementioned, hardware structure of an alternative embodiment of a computer or console 1300' is shown in FIG. 32. The computer 1300' includes a central processing unit (CPU) 1301, a graphical processing unit (GPU) 1315, a random access memory (RAM) 1303, a network interface device 1312, an operation interface 1314 such as a universal serial bus (USB) and a memory such as a hard disk drive or a solid state drive (SSD) 1307. Preferably, the computer or console 1300' includes a display 1309. The computer 1300' may connect with a motor, a console, and/or any other component of the device(s) or system(s) discussed herein via the operation interface 1314 or the network interface 1312 (e.g., via a cable or fiber, such as the cable or fiber 113 as similarly shown in FIG. 31). A computer, such as the computer 1300', may include a motor or motion control unit (MCU) in one or more embodiments. The operation interface 1314 is connected with an operation unit such as a mouse device 1311, a keyboard 1310 or a touch panel device. The computer 1300' may include two or more of each component.

At least one computer program is stored in the SSD 1307, and the CPU 1301 loads the at least one program onto the RAM 1303, and executes the instructions in the at least one program to perform one or more processes described herein, as well as the basic input, output, calculation, memory writing and memory reading processes.

The computer, such as the computer 1300, 1300', may communicate with an MCU, a rotary junction, etc. to perform imaging, and reconstructs an image from the acquired intensity data. The monitor or display 1309 displays the reconstructed image, and may display other information about the imaging condition or about an object to be imaged. The monitor 1309 also provides a graphical user interface for a user to operate any system discussed herein. An operation signal is input from the operation unit (e.g., such as, but not limited to, a mouse device 1311, a keyboard 1310, a touch panel device, etc.) into the operation interface 1314 in the computer 1300', and corresponding to the operation signal the computer 1300' instructs any system discussed herein to set or change the imaging condition (e.g., improving resolution of an image or images), and to start or end the imaging. A light or laser source and a spectrometer and/or detector may have interfaces to communicate with the computers 1300, 1300' to send and receive the status information and the control signals.

The present disclosure and/or one or more components of devices, systems and storage mediums, and/or methods, thereof also may be used in conjunction with any suitable optical assembly including, but not limited to, SEE probe technology, such as in U.S. Pat. Nos. 6,341,036; 7,447,408; 7,551,293; 7,796,270; 7,859,679; 8,045,177; 8,145,018; 8,838,213; 9,254,089; 9,295,391; 9,415,550; and 9,557,154 and arrangements and methods of facilitating photoluminescence imaging, such as those disclosed in U.S. Pat. No. 7,889,348 to Tearney et al. Other exemplary SEE systems are described, for example, in U.S. Pat. Pubs. 2016/0341951; 2016/0349417; US2017/0035281; 2017/167861; 2017/0168232; 2017/0176736; 2017/0290492; 2017/0322079, 2012/0101374; and WO2015/116951; WO2015/116939; WO2017/117203; WO2017/024145; WO2017/165511; WO2017/139657 and U.S. Non-Provisional patent application Ser. No. 15/418,329 filed Jan. 27, 2017 and published as U.S. Pat. Pub. No. 2018/0017778, each of which patents, patent publications and patent application(s) are incorporated by reference herein in their entireties.

Although the disclosure herein has been described with reference to particular embodiments, it is to be understood that these embodiments are merely illustrative of the principles and applications of the present disclosure (and are not limited thereto), and the invention is not limited to the disclosed embodiments. It is therefore to be understood that numerous modifications may be made to the illustrative embodiments and that other arrangements may be devised without departing from the spirit and scope of the present disclosure. The scope of the following claims is to be accorded the broadest interpretation so as to encompass all such modifications and equivalent structures and functions.

INDUSTRIAL APPLICABILITY

The present invention is applicable, but not limited, to acquiring an image(s), such as, but not limited to, black and white images and/or color images, by using an optical system at an end of a miniaturized probe in Spectrally encoded endoscopy (SEE).

What is claimed is:

1. An endoscope comprising:
a first waveguide for guiding light from a light source to an output port of the first waveguide;
an optical system comprising at least a first reflecting surface and a second reflecting surface; and
a diffraction grating;
wherein the first reflecting surface is arranged to reflect light from the output port of the first waveguide to the second reflecting surface;
wherein the second reflecting surface is arranged to reflect light from the first reflecting surface back through the first reflecting surface to the diffraction grating; and
wherein the diffraction grating diffracts light from the second reflecting surface in a non-zero diffraction order in a first direction.

2. The endoscope according to claim 1, wherein the first reflecting surface is a total internal reflecting surface for at least a portion of light that the first reflecting surface receives from the output port of the first waveguide.

3. The endoscope according to claim 1, wherein the first reflecting surface and a portion of the diffraction grating component are on the same plane and are both on a single support structure.

4. The endoscope according to claim 1, wherein the second reflecting surface is a curved surface.

5. The endoscope according to claim 1, wherein the optical system further comprises a spacer located between the output port of the first waveguide and the first reflecting surface.

6. The endoscope according to claim 5, wherein the spacer includes a GRIN lens.

7. The endoscope according to claim 6, wherein an optical axis of the first waveguide is co-linear with an optical axis of the GRIN lens.

8. The endoscope according to claim 1, wherein:
an end portion of the endoscope is between the output port of the first waveguide and an illumination surface;
the illumination surface is a final surface of the endoscope out of which illumination light exits the endoscope; and
a diameter of an end portion of the endoscope is less than 350 pm.

9. The endoscope according to claim 1, wherein the endoscope has a plurality of propagation modes, wherein:
in a first propagation mode among the plurality of propagation modes, light from the output port of the first waveguide is reflected by the first reflecting surface, then reflected by the second reflecting surface, and is then diffracted by the diffraction grating; and
in a second propagation mode among the plurality of propagation modes, light from the output port of the first waveguide is diffracted by the diffraction grating and is not reflected by the first reflecting surface or the second reflecting surface.

10. The endoscope according to claim 9, further comprising a detector and a switch.

11. The endoscope according to claim 1, wherein:
the first reflecting surface is configured to receive light from the output port at a first angle with respect to a normal of the first reflecting surface; and
the first angle is greater than a critical angle for total internal reflection.

12. The endoscope according to claim 1, wherein the first reflecting surface and the diffraction grating component are on substantially parallel planes.

13. The endoscope according to claim 12, wherein the first reflecting surface is an interface between a single support structure and a thin film or layer and the diffraction grating is on the thin film or layer.

14. The endoscope according to claim 1, wherein the second reflecting surface is a surface of a ball lens.

15. The endoscope according to claim 1, wherein:
the endoscope is a color endoscope; and
the diffraction grating diffracts light from the second reflecting surface in blue, green and red wavelength lights of non-zero diffraction orders, which are mutually different in the diffraction order, in the first direction.

16. The endoscope according to claim 15, wherein the optical system further comprises a spacer including a GRIN lens, the spacer being located between the output port of the first waveguide and the first reflecting surface, and a light exiting end of the GRIN lens is inclined in a predetermined direction so that the first reflecting surface is a total internal reflecting surface.

17. The endoscope according to claim 15, wherein a gap between a rotation center of an end portion of the endoscope and a center of the light beam exiting from the diffraction grating is less than 1/10 of the diameter of the circle circumscribing the end portion of the endoscope.

18. The endoscope according to claim 15, wherein the first reflecting surface is an interface between a single support structure and a thin layer and the diffraction grating is on the thin layer, and the refractive index N1 of the support structure and the refractive index N2 of the thin layer satisfy N2/N1<0.8.

19. The endoscope according to claim 18, wherein the thin layer is an air gap and the refractive index N2 of the thin layer satisfies N2=1.

20. The endoscope according to claim 19, wherein the diffraction grating is supported by a cover glass.

21. The endoscope according to claim 18, wherein a forming member of the diffraction grating also serves as the thin layer.

22. An imaging apparatus comprising:
a light source;
a detector;
a first waveguide for guiding light from the light source to an output port of the first waveguide;
an optical system comprising at least a first reflecting surface and a second reflecting surface;

a diffraction grating;
  wherein the first reflecting surface is arranged to reflect light from the output port of the first waveguide to the second reflecting surface;
  wherein the second reflecting surface is arranged to reflect light from the first reflecting surface back through the first reflecting surface to the diffraction grating;
  wherein the diffraction grating diffracts light from the second reflecting surface in a non-zero diffraction order in a first direction; and
a second waveguide for gathering light and sending the gathered light to the detector.

23. A probe comprising:
a first waveguide; and
an optical system comprising at least:
  a first reflecting surface;
  a second reflecting surface; and
  a diffraction grating;
wherein the diffraction grating receives light and is arranged to diffract the received light through the first reflecting surface;
wherein the second reflecting surface is arranged to receive diffracted light which passed through the first reflecting surface that was diffracted by the diffraction grating and reflect the diffracted light back towards the first reflecting surface;
wherein the first reflected surface is arranged to reflect the diffracted light from the second reflecting surface towards the first waveguide; and
wherein the first waveguide is arranged to receive the diffracted light that the first reflecting surface reflects from the second reflecting surface.

24. The probe according to claim 23, wherein:
the first reflecting surface is configured to receive light from the second reflecting surface at a first angle with respect to a normal of the first reflecting surface; and
the first angle is greater than a critical angle for total internal reflection.

25. The probe according to claim 23, wherein the first reflecting surface and the diffraction grating component are on substantially parallel planes.

26. The endoscope according to claim 1, wherein the diffraction grating defines a first diffraction grating and the endoscope further includes a second diffraction grating, or the diffraction grating comprises the first diffraction grating and the second diffraction grating:
  wherein the second reflecting surface is arranged to reflect a first portion of light from the first reflecting surface towards the first diffraction grating;
  wherein the second reflecting surface is arranged to transmit a second portion of the light from the first reflecting surface through the second diffraction grating;
  wherein the first diffraction grating diffracts light reflected from the second reflecting surface in a non-zero diffraction order in a first direction; and
  wherein the second diffraction grating diffracts light transmitted through the second reflecting surface in a non-zero diffraction order in a second direction different from the first direction.

* * * * *